US010813988B2

(12) United States Patent
Super et al.

(10) Patent No.: US 10,813,988 B2
(45) Date of Patent: Oct. 27, 2020

(54) PATHOGEN VACCINES AND METHODS OF PRODUCING AND USING THE SAME

(71) Applicant: President and Fellows of Harvard College, Cambridge, MA (US)

(72) Inventors: Michael Super, Lexington, MA (US); Edward J. Doherty, Mansfield, MA (US); Mark Cartwright, West Newton, MA (US); Des White, Boston, MA (US); Alexander G. Stafford, Revere, MA (US); Omar Abdel-Rahman Ali, Cambridge, MA (US); Amanda Graveline, Boston, MA (US); Donald E. Ingber, Boston, MA (US); David J. Mooney, Sudbury, MA (US); Benjamin Seiler, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/434,781

(22) Filed: Feb. 16, 2017

(65) Prior Publication Data

US 2017/0246281 A1    Aug. 31, 2017

Related U.S. Application Data

(60) Provisional application No. 62/343,448, filed on May 31, 2016, provisional application No. 62/295,711, filed on Feb. 16, 2016.

(51) Int. Cl.
*A61K 39/108* (2006.01)
*A61K 39/02* (2006.01)
*A61K 39/00* (2006.01)

(52) U.S. Cl.
CPC ........ *A61K 39/0258* (2013.01); *A61K 39/025* (2013.01); *A61K 2039/55522* (2013.01); *A61K 2039/55561* (2013.01); *A61K 2039/58* (2013.01); *A61K 2039/6031* (2013.01); *A61K 2039/6093* (2013.01); *Y02A 50/474* (2018.01)

(58) Field of Classification Search
None
See application file for complete search history.

(56) References Cited

U.S. PATENT DOCUMENTS

| 5,951,976 A | 9/1999 | Segal | |
| 7,410,953 B2* | 8/2008 | Kawasaki | A61K 38/1709 514/44 R |
| 8,535,719 B2* | 9/2013 | Badylak | A61L 27/3633 424/426 |
| 8,728,456 B2* | 5/2014 | Sands | A61K 39/35 424/85.2 |
| 9,150,631 B2* | 10/2015 | Super | C07K 14/4726 |
| 9,381,235 B2* | 7/2016 | Sands | A61K 39/35 |
| 9,591,360 B2* | 3/2017 | Jennings | H04N 7/165 |
| 9,821,045 B2* | 11/2017 | Ali | A61K 39/39 |
| 10,045,947 B2* | 8/2018 | Bencherif | A61L 27/52 |
| 10,137,184 B2* | 11/2018 | Mooney | A61L 27/56 |
| 10,149,897 B2* | 12/2018 | Mooney | A61L 27/58 |
| 2004/0043034 A1* | 3/2004 | Jensenius | A61K 39/39 424/185.1 |
| 2008/0268019 A1* | 10/2008 | Badylak | A61L 27/3633 424/426 |
| 2012/0100182 A1 | 4/2012 | Mooney et al. | |
| 2012/0121539 A1* | 5/2012 | Sands | A61K 39/35 424/85.2 |
| 2013/0035283 A1* | 2/2013 | Super | C07K 14/4726 514/2.3 |
| 2014/0227723 A1* | 8/2014 | Ingber | G01N 33/54353 435/7.92 |
| 2014/0234423 A1* | 8/2014 | Sands | A61K 39/35 424/489 |
| 2017/0246281 A1* | 8/2017 | Super | A61K 39/025 |
| 2017/0362307 A1* | 12/2017 | Ingber | G01N 33/54353 |

(Continued)

FOREIGN PATENT DOCUMENTS

| WO | WO-2008008266 A2 * | 1/2008 | ......... A61L 27/3633 |
| WO | WO-2011014871 A1 * | 2/2011 | ............. A61K 39/35 |

(Continued)

OTHER PUBLICATIONS

Mehta et al, Cancer Immunology Research, 2015, 6/8:836-843. Published Online First: Jul. 8, 2015 (Year: 2015).*
Ali et al, J. Controlled Release, 2011, 154:249-257. Available online, Jun. 16, 2011 (Year: 2011).*
Alli et al, Journal Controlled Release, 2008, 132:273-278. Available online: Jul. 10, 2008 (Year: 2008).*
Bojarova et al, Biomater. Sci., 2016, 4:1142-1160 (Year: 2016).*
Kratz, Journal of Controlled Release, 2008, 132:171-183. (Year: 2008).*
Mu et al, Fish and Shellfish Immunology, 2017, 67:244-253. available online: Jun. 7, 2017 (Year: 2017).*
Casanova et al, J. Exp. Med., May 17, 2004, 199/10:1295-1299. (Year: 2004).*

(Continued)

*Primary Examiner* — Nita M. Minnifield
(74) *Attorney, Agent, or Firm* — McCarter & English, LLP; Maria Laccotripe Zacharakis; Deborah L. Nagle

(57) ABSTRACT

The present invention provides vaccine compositions and methods of producing such compositions. Other embodiments of the invention include methods of treating a pathogen infection, methods of vaccinating a subject against a pathogen infection, and methods for treating an antibiotic-resistance bacterial infection in a subject in need thereof. In further embodiments, the invention includes methods of decreasing the level of a pathogen in a subject having a pathogen infection, methods of increasing the surviving rate of a subject having a pathogen infection, methods of reducing the level of pain associated with a pathogen infection, and methods of reducing the level of distress associated with a pathogen infection in a subject in need thereof. Novel scaffold compositions and opsonin-bound or lectin-bound pathogen compositions, and uses thereof, are also provided herein.

79 Claims, 26 Drawing Sheets

Specification includes a Sequence Listing.

(56) References Cited

U.S. PATENT DOCUMENTS

| | | | | |
|---|---|---|---|---|
| 2018/0320157 A1* | 11/2018 | Super | | A61K 38/00 |
| 2018/0371058 A1* | 12/2018 | Watters | | C07K 14/00 |
| 2019/0292517 A1* | 9/2019 | Cheung | | A61K 39/395 |

FOREIGN PATENT DOCUMENTS

| | | | | |
|---|---|---|---|---|
| WO | WO-2011043834 A1 * | 4/2011 | ......... | C07K 14/4726 |
| WO | WO-2011043835 A1 * | 4/2011 | ......... | C07K 14/4726 |
| WO | WO-2013012924 A2 * | 1/2013 | ....... | G01N 33/54353 |
| WO | WO-2015168379 A2 * | 11/2015 | ......... | A61K 39/0011 |
| WO | WO-2017143024 A2 * | 8/2017 | ........... | A61K 39/025 |
| WO | WO-2018013797 A1 * | 1/2018 | .............. | A61P 35/00 |
| WO | WO-2018026884 A1 * | 2/2018 | ........... | A61K 9/0019 |

OTHER PUBLICATIONS

Ali et al, Journal of Controlled Release, 2011, 154:249-257. available online: Jun. 16, 2011 (Year: 2011).*

Mehta et al Cancer Immunology Research, 2015, 3/8:836-843. published online first:Jul. 8, 2015 (Year: 2015).*

Li et al, Regenerative Biomaterials, 2016, pp. 99105. advance access publication date: Mar. 5, 2016 (Year: 2016).*

Ali et al Biomatter, Jul./Aug./Sep. 2011, 1/1:66-75 (Year: 2011).*

Ali, et al. "Identification of immune factors regulating antitumor immunity using polymeric vaccines with multiple adjuvants." Cancer Res. 74(6):1670-1681 (2014).

McConnell, et al., "Vaccination with Outer Membrane Complexes Elicits Rapid Protective Immunity to Multidrug-Resistant Acinetobacter baumannii." Infect Immun. 79(1):518-526 (2011).

Irvine et al, "Engineering synthetic vaccines using cues from natural immunity." Naure Materials 12:978-990 (2013).

Ali et al. "The efficacy of intracranial PLG-based vaccines is dependent on direct implantation into brain tissue." J Control Release 154(3):249-257 (2011).

Zizzari et al., "The Macrophage Galactose-Type C-Type Lectin (MGL) Modulates Regulatory T Cell Functions" PLoS ONE 10(7):e132617 2015.

International Search Report and Written Opinion from PCT/US2017/018114 dated Aug. 15, 2017.

U.S. Appl. No. 15/564,905, filed Oct. 6, 2017, 2018-0164298, Published.

U.S. Appl. No. 16/316,778, filed Jan. 10, 2019, Pending.

U.S. Appl. No. 11/638,796, filed Dec. 13, 2006, now U.S. Pat. No. 8,067,237, Issued.

U.S. Appl. No. 13/305,088, filed Nov. 28, 2011, now U.S. Pat. No. 8,932,583, Issued.

U.S. Appl. No. 14/223,759, filed Mar. 24, 2014, now U.S. Pat. No. 9,132,210, Issued.

U.S. Appl. No. 14/750,423, filed Jun. 25, 2015, now U.S. Pat. No. 9,446,107, Issued.

U.S. Appl. No. 15/085,858, filed Mar. 30, 2016, 2016-0271298, Abandoned.

U.S. Appl. No. 15/135,207, filed Apr. 21, 2016, now U.S. Pat. No. 10,149,897, Issued.

U.S. Appl. No. 15/135,213, filed Apr. 21, 2016, now U.S. Pat. No. 10,137,184, Issued.

U.S. Appl. No. 16/170,313, filed Oct. 25, 2018, 2019-0125849, Published.

U.S. Appl. No. 13/877,572, filed Nov. 19, 2013, 2014-0079752, Published.

U.S. Appl. No. 14/112,096, filed Dec. 27, 2013, now U.S. Pat. No. 10,045,947, Issued.

U.S. Appl. No. 14/166,689, filed Jan. 28, 2014, now U.S. Pat. No. 9,675,561, Issued.

U.S. Appl. No. 15/617,837, filed Jun. 8, 2017, 2018-0243231, Published.

U.S. Appl. No. 16/033,025, filed Jul. 11, 2018, 2019-0076373, Published.

U.S. Appl. No. 14/394,552, filed Oct. 15, 2014, now U.S. Pat. No. 9,937,249, Issued.

U.S. Appl. No. 15/935,392, filed Mar. 26, 2018, 2018-0344821, Published.

U.S. Appl. No. 15/303,985, filed Oct. 13, 2016, 2017-0042995, Published.

U.S. Appl. No. 16/263,098, filed Jan. 31, 2019, 2019-0216910, Published.

* cited by examiner

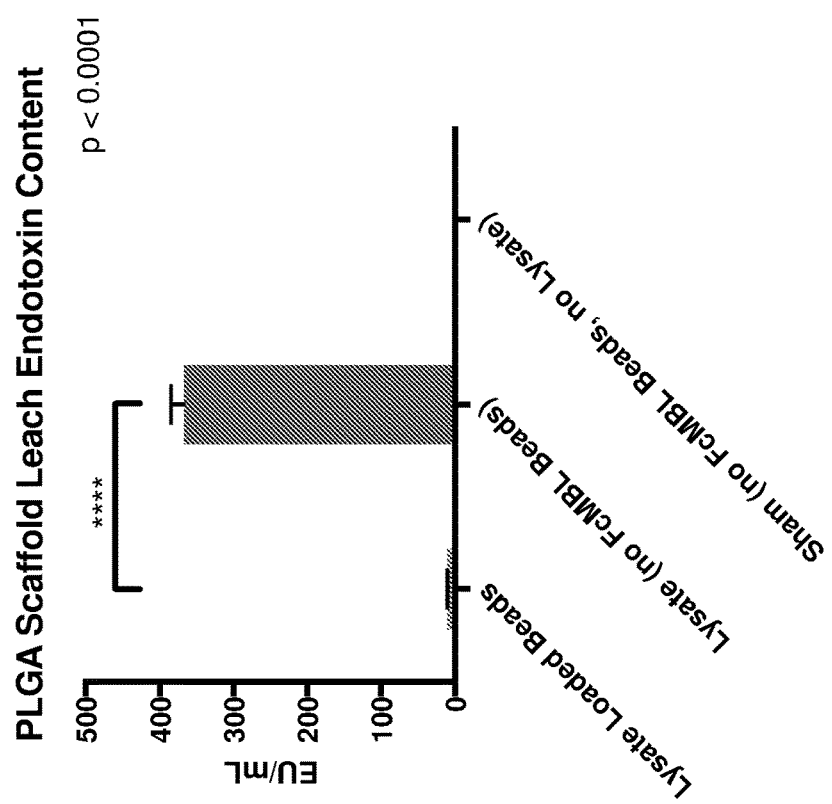

RS218 lysate
(PLG scaffold & GMCSF/CpG)

RS218 + FcMBL Bead
(PLG scaffold & GMCSF/CpG)

Sham
(PLG scaffold & GMCSF/CpG)

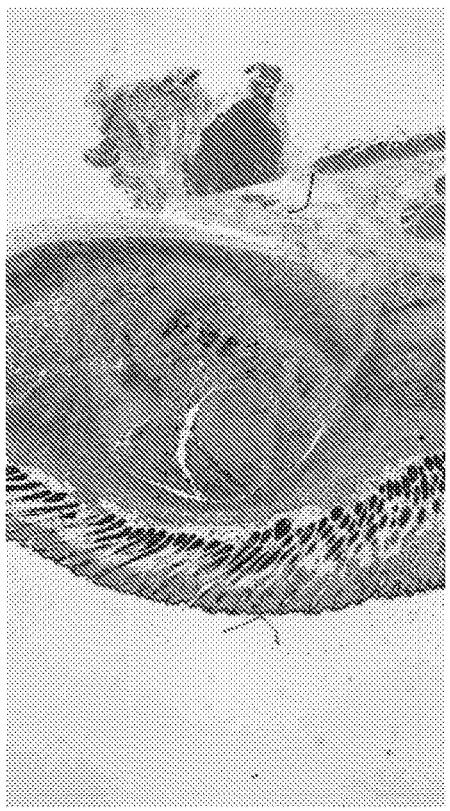
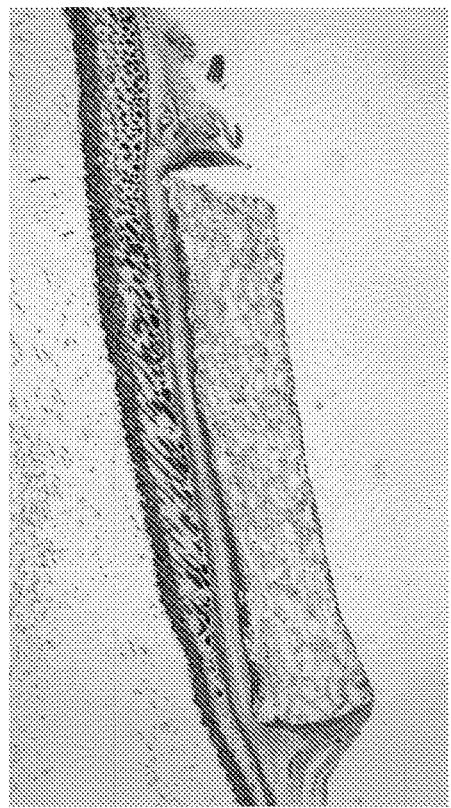
FIG. 16

SEQUENCE LISTING

```
<160> NUMBER OF SEQ ID NOS: 1

<210> SEQ ID NO 1
<211> LENGTH: 148
<212> TYPE: PRT
<213> ORGANISM: Homo sapiens

<400> SEQUENCE: 1

Pro Asp Gly Asp Ser Ser Leu Ala Ala Ser Glu Arg Lys Ala Leu Gln
1               5                   10                  15

Thr Glu Met Ala Arg Ile Lys Lys Trp Leu Thr Phe Ser Leu Gly Lys
            20                  25                  30

Gln Val Gly Asn Lys Phe Phe Leu Thr Asn Gly Glu Ile Met Thr Phe
        35                  40                  45
```

```
Glu Lys Val Lys Ala Leu Cys Val Lys Phe Gln Ala Ser Val Ala Thr
 50                  55                  60

Pro Arg Asn Ala Ala Glu Asn Gly Ala Ile Gln Asn Leu Ile Lys Glu
 65                  70                  75                  80

Glu Ala Phe Leu Gly Ile Thr Asp Glu Lys Thr Glu Gly Gln Phe Val
                 85                  90                  95

Asp Leu Thr Gly Asn Arg Leu Thr Tyr Thr Asn Trp Asn Glu Gly Glu
                100                 105                 110

Pro Asn Asn Ala Gly Ser Asp Glu Asp Cys Val Leu Leu Leu Lys Asn
            115                 120                 125

Gly Gln Trp Asn Asp Val Pro Cys Ser Thr Ser His Leu Ala Val Cys
        130                 135                 140

Glu Phe Pro Ile
145
```

PATHOGEN VACCINES AND METHODS OF PRODUCING AND USING THE SAME

RELATED APPLICATIONS

This application claims the benefit of priority to U.S. Provisional Application No. 62/343,448, filed on May 31, 2016, and U.S. Provisional Application No. 62/295,711, filed on Feb. 16, 2016. The entire contents of each of the foregoing applications are incorporated herein by reference.

GOVERNMENT SUPPORT

The invention was made with government support under DARPA N66001-11-1-4180. The government has certain rights in the invention.

SEQUENCE LISTING

The instant application contains a Sequence Listing which has been submitted electronically in ASCII format and is hereby incorporated by reference in its entirety. Said ASCII copy, created on Sep. 28, 2018, is named 117823_12203_SeqList.TXT and is 1,681 bytes in size.

BACKGROUND OF THE INVENTION

Infectious diseases are caused by a pathogenic microorganism, like a virus, bacterium, fungus, or the like which enters and propagates in a living body. Common strategies to treat infectious diseases include the administration of antimicrobial drugs such as antivirals or antibiotics, or the use of immunotherapy such as vaccination, to patients suffering from or prone to suffering such infections.

However, in some cases, the pathogenic microorganisms can not be easily eradicated by the use of existing antimicrobial drugs as these microorganisms may acquire resistance to drugs, or the drugs may pose undesirable side effects to varying degrees to patients. As a result, known antibiotics and antivirals have not been entirely satisfactory in terms of their antimicrobial activity, behavior in the body, safety, or ability to suppress drug-resistant microorganisms.

Vaccines reduce the risk of infection by working with the body's natural defenses to help it safely develop immunity against pathogens. Although vaccines have been considered among the most powerful tools available to public health, there are certain limitations associated with vaccines for treating or preventing infectious diseases. For example, development of vaccines against a pathogen infection usually requires identification or isolation of the pathogen. In the case where the specific pathogen is unknown or isolation of a pathogen poses a great difficulty, preparation of vaccines would be of a great challenge and may take a much longer time. In addition, antigenicity of the pathogen is easily altered, and for pathogens that have multiple strains with different surface antigens, inconsistency in the antigen structure between vaccine strain and the infected strain would be a significant problem. When a strain different from the vaccine administered causes an infectious disease, the vaccination becomes ineffective. Furthermore, pathogen leakage has been observed in certain vaccines and causes undesired side effect and massive inflammation within the subject.

As a result, infectious diseases remain a major public health threat and a leading cause of illness, disability and death across the world. Accordingly, there remains an ongoing and unmet need for the development of novel therapeutic strategies and vaccines to treat infectious diseases.

SUMMARY OF THE INVENTION

The present invention is based, at least in part, on the discovery that pathogens or pathogen associated molecular patterns (PAMPs) isolated using an opsonin or lectin, e.g., an engineered lectin or fragment thereof, can be used to generate functional vaccines for the treatment of infectious diseases. In particular, the present inventors have surprisingly discovered that, pathogens or pathogen associated molecular patterns (PAMPs) isolated using an engineered lectin when combined with a bioactive agent, e.g., an adjuvant, and/or a scaffold, allow for the rapid creation of high potency pathogen vaccines (FIG. 1). When used to vaccinate animals, a single dose of these vaccines resulted in a significantly reduced pathogen titer in the vaccinated animals and a significantly prolonged survival time after infecting the animals with a lethal dose of bacteria. Indeed, as shown in Example 1, a single dose of the vaccine composition of the invention can protect the vaccinated mice from a bacteria challenge over a period of 90 days. In addition, the opsonin or lectin, e.g., an engineered lectin or fragment thereof, not only functions to isolate a pathogen for use in the vaccine compositions and present the pathogen to immune cells to initiate an immune response, but also serves as an anchor structure to immobilize the pathogen, thus preventing leakage of the pathogen from the vaccine composition, and preventing any undesired side effects currently experienced with pathogen leakage.

The vaccine compositions of the present invention possess additional improvements over existing vaccines. For example, the vaccine compositions of the present invention allow the rapid and direct isolation of pathogens circulating in a blood sample from a patient with infectious disease including both known and unknown pathogens, pathogens present within other biological fluids, or pathogens present in in vitro cultures. The claimed vaccine compositions can also be used against pathogens that are difficult to isolate and purify. Once the pathogens are isolated from a subject, the vaccine compositions can be readily prepared in a fast and convenient manner anywhere in the world, and can be available for patients in a timely manner, for example, within one day. In addition, vaccination using the claimed vaccine compositions can occur in a more controlled, localized and safer manner, without compromising the efficacy of the vaccine compositions. The improved stability of the claimed vaccines allows them to be portable and to be used for long term storage at room temperature without the need of refrigeration. Furthermore, the vaccine compositions can be multivalent vaccines when more than one type of pathogens are included in the compositions, and can also be used to vaccinate against different species or strains of a given pathogen. In addition, the vaccine compositions, if implanted, can be easily removed from the subject after vaccination. For example, in the case where too much immune response or undesired side effects are initiated after vaccination, the implanted vaccine compositions can be readily removed from the subject. In contrast, current existing vaccines cannot be removed once they are introduced in the subjects. These improvements circumvent the major limitations of current pathogen vaccines, and would be of great interest to the public, especially during the time of an epidemic, for example, for populations in developing countries, or of great value for military uses, where vaccines that are readily available are highly desired. Indeed, the ability to rapidly create functional and highly stable vaccines that are not only easy for storage and handling, but may be administered in a safer and more controlled manner and confer a long-term protective effect, renders the vaccine compositions of the present invention significantly advantageous over existing vaccines.

Accordingly, in one aspect, the present invention provides vaccine compositions. The vaccine compositions comprise an opsonin-bound or lectin-bound pathogen construct, and a bioagent capable of recruiting an immune cell in a subject.

In some embodiments, the bioagent is selected from the group consisting of interleukin (IL)-1, IL-2, IL-3, IL-4, IL-5, IL-6, IL-7, IL-8, IL-10, IL-12, IL-15, IL-17, IL-18, tumor necrosis factor (TNF)-alpha, interferon (IFN)-gamma, IFN-alpha, granulocyte macrophage colony stimulating factor (GM-CSF), granulocyte colony stimulating factor (G-CSF), Fms-related tyrosine kinase ligand (FTL)-3 ligand, CCL19, CCL21, M-SCF, MIF, CD40L, CD3, ICAM, transforming growth factor (TGF)-beta, cytosine-guanosine oligonucleotide (CpG-ODN), lipopolysaccharides (LPS), Fas ligand, Trail, lymphotactin, Mannan (M-FP), APG-2, Hsp70 and Hsp90.

In some embodiments, the bioagent comprises an adjuvant. In other embodiments, the adjuvant is selected from the group consisting of cytosine-guanosine oligonucleotide (CpG-ODN) sequence, granulocyte macrophage colony stimulating factor (GM-CSF), ovalbumin (OVA), monophosphoryl lipid A (MPL), poly(I:C), MF59, alum, aluminum hydroxide, aluminum phosphate, calcium phosphate hydroxide, Quil A, N-acetyl muramyl-L-alanyl-D-isoglutamine (MDP), FIA, montanide, adjuvant 65, lipovant, poly (DL-lactide-coglycolide) microspheres, paraffin oil, squalene, virosome, AS03, AS04, IL-1, IL-3, IL-4, IL-5, IL-6, IL-7, IL-8, IL-10, IL-12, IL-15, IL-17, IL-18, STING, Toll-like receptor ligand, CD40L, pathogen-associated molecular patterns (PAMPs), damage-associated molecular pattern molecules (DAMPs), Freund's complete adjuvant, Freund's incomplete adjuvant, antibodies against immune suppressive molecules (e.g., antibody or antagonist against transforming growth factor (TGF)-beta, A2aR antagonists), lipopolysaccharides (LPS), Fas ligand, Trail, lymphotactin, Mannan (M-FP), APG-2, Hsp70 and Hsp90.

In some embodiments, the lectin-bound pathogen construct comprises a lectin, a portion of a lectin, an engineered lectin or a portion thereof. In some embodiments, the lectin is a collectin. In other embodiments, the lectin is a ficolin. In some embodiments, the lectin is a mannose-binding lectin (MBL). In other embodiments, the lectin comprises amino acid residues 81 to 228 of MBL (SEQ ID NO: 1). In yet another embodiment, the lectin comprises amino acid residues 111 to 228 of MBL. In some embodiments, the mannose-binding lectin (MBL) is capable of binding to the pathogen. In some embodiments, the lectin comprises Surfactant Protein D (SPD). In other embodiments, the Surfactant Protein D (SPD) is capable of binding to the pathogen.

In some embodiments, the opsonin-bound or lectin-bound pathogen construct further comprises an immunoglobulin (IgG) Fc portion.

In some embodiments, the opsonin-bound or lectin-bound pathogen construct further comprises a solid substrate. In other embodiments, the solid substrate is selected from the group consisting of a magnetic bead, a microporous membrane, a hollow-fiber reactor, a blood filtration membrane and a blood flow device. In some embodiments, the solid substrate is a magnetic bead. In other embodiments, the pathogen is present on the solid substrate at a quantity of about 1 pg to about 1000 µg.

In some embodiments, the pathogen is an infectious microorganism selected from the group consisting of a bacterium, a fungus, a virus and a parasite, or a fragment thereof.

In some embodiments, the bacterium is selected from the group consisting of *Acinetobacter baumanii, Burkholderia cepacia, Bacterioides fragilis, Chlamydia trachomatis, Citrobacter freundii, Campylobacter jejuni, Escherichia coli, Enterobacter aerogenes, Enterobacter cloacae, Haemophilus inf'b, Helicobacter pylori, Klebsiella oxytoca, K. pneumonia* (MDR/CRE), *Legionella pneumophila, Neisseria meningitides, Neisseria gonorrhoeae, Pseudomonas aeruginosa, Salmonella typhi, paratyphi, typhimurium, Serratia marcescens, Shigella flexneri, Stenotrophomonas maltophilia, Yersinia pseudotuberculosis, Bacillus subtilis, Clostridium neoformans, C. difficile, C. perfringens, Corynebacterium* spp, *Enterococcus faecalis, Enterococcus faecium*, vancomycin-resistant *Enterococci* (VRE), *Listeria monocytogenes, Mycobactrium avium, M. tuberculosis, M. leprae, Nocardia farcinica, P. acnes, Staphylococcus aureus*, methicillin-susceptible *Staphylococcus aureus* (MSSA), methicillin-resistant *Staphylococcus aureus* (MRSA), *Staphylococcus epidermidis, Streptococcus pyogenes*, Strep Group A, Strep Group B (agalactiae) and Strep Group C.

In some embodiments, the bacterium is an antibiotic-resistant bacterium. In some embodiment, the bacterium is a multi-drug resistant bacterium. In other embodiments, the antibiotic-resistant bacterium or the multi-drug resistant bacterium is selected from the group consisting of *Acinetobacter baumanii, Escherichia coli, Klebsiella oxytoca, K. pneumonia* (MDR/CRE), *Pseudomonas aeruginosa, C. difficile*, vancomycin-resistant *Enterococci* (VRE) and methicillin-resistant *Staphylococcus aureus* (MRSA).

In some embodiments, the fungus is selected from the group consisting of *Aspergillus* spp, *Blastomyces, Candida albicans, glabrata, guilliermondii, krusei, parapsilosis, tropicalis Cryptococcus, Fusarium* spp., *Mucor* spp., *Saccharomyces*, and *Pneumocystis jirovecii (carinii)*.

In some embodiments, the virus is selected from the group consisting of Dengue virus, Ebola virus, EBV, Hepitis A virus, Hepitis B virus, Hepitis C virus, Hepitis D virus, HIV, HSV 1, HSV 2, Cytomegalovirus (CMV), Influenza A virus, Marburg virus, Human respiratory syncytial virus (RSV), SARS-CoV, West Nile virus, Human papillomavirus (HPV), Human rhinoviruses (HRVs), and Zica virus.

In some embodiments, the parasite is selected from the group consisting of *Cryptosporidium, Leishmania, Malaria, Schistosoma, Trichomonasm* and *Trypanosoma*.

In some embodiments, the pathogen comprises a cell wall component of the infectious microorganism. In other embodiments, the pathogen comprises the whole infectious microbial cell. In some embodiments, the cell wall components of the infectious microorganism are glycosylated. In other embodiments, the cell wall components are mannosylated. In some embodiments, the cell wall components are mannose-capped lipoarabinomannan (ManLAM). In other embodiments, the cell wall components are phosphatidylinositol mannoside (PIM).

In some embodiments, the pathogen is a mycoplasma. In other embodiments, the mycoplasma is selected from the group consisting of *M. pneumoniae, M. hominis* and *M. orale*.

In some embodiments, the pathogen comprises a pathogen-associated molecule pattern (PAMP). In other embodiments, the PAMP is selected from the group consisting of a pathogen fragment, a pathogen debris, a pathogen nucleic acid, a pathogen lipoprotein, a pathogen surface glycoprotein, a pathogen membrane component, and a component released from the pathogen.

In some embodiments, the component released from the pathogen comprises a toxin. In other embodiments, the toxin is selected from the group consisting of endotoxin, lipopolysaccharide (LPS), lipoteichoic acid (LTA), wall teichoic acid (WTA) and Ricin.

In some embodiments, the pathogen is in a sample derived from a subject in vivo. In other embodiments, the sample is selected from the group consisting of a blood sample, a plasma sample, a serum sample, a blood culture sample, a cerebrospinal fluid sample, a joint fluid sample, a urine sample, a semen sample, a saliva sample, a sputum sample, a bronchial fluid sample, and a tear sample.

In some embodiments, the pathogen is derived from an in vitro culture, a microorganism lysate, a crude lysate, or a purified lysate. In some embodiments, the pathogen is a synthetic pathogen.

In some embodiments, the pathogen is neutralized. In other embodiments, the pathogen is neutralized by treatment with antibiotics, ultraviolet light, sonication, microwave, bead mill, x-ray, autoclave, irradiation or mechanical disruption. In some embodiments, the pathogen is non-infectious after neutralization.

In some embodiments, the immune cell is an antigen-presenting cell. In other embodiments, the immune cell is selected from the group consisting of a dendritic cell, a macrophage, a T cell and a B cell.

In some embodiments, the vaccine composition comprises at least two different types of pathogen. In other embodiments, the vaccine composition comprises at least three different types of pathogen. In some embodiments, the vaccine composition is capable of targeting against different species of a pathogen.

In some embodiments, the vaccine composition is suitable for implantation in a subject. In other embodiments, the vaccine composition is suitable for subcutaneous implantation. In some embodiments, the vaccine composition is suitable for injection in a subject. In other embodiments, the vaccine composition is suitable for oral administration in a subject. In another embodiment, the vaccine composition is in the form of a pill, a tablet, a capsule, a soft gel, a chewable, a powder, an emulsion, or an aqueous solution.

In some embodiments, the vaccine composition is lyophilized. In other embodiments, the vaccine composition has a shelf life of about 30 days to about 1 year. In some embodiments, the vaccine composition has a shelf life of at least 1 year. In other embodiments, the vaccine composition is capable of being stored at room temperature. In some embodiments, the vaccine composition is portable.

In some embodiments, the subject is a mammal. In other embodiments, the mammal is selected from the group consisting of a human, an embryo, a horse, a dog, a cat, a cow, a sheep, a pig, a fish, an amphibian, a reptile, a goat, a bird, a monkey, a mouse, a rabbit, and a rat. In some embodiments, the mammal is a human.

In some embodiments, the vaccine compositions further comprise a scaffold comprising a biomaterial and capable of recruiting and activating the immune cell in the subject.

In some embodiments, the biomaterial is selected from the group consisting of glycosaminoglycan, silk, fibrin, MATRIGEL®, poly-ethyleneglycol (PEG), polyhydroxy ethyl methacrylate, polyvinyl alcohol, polyacrylamide, poly (N-vinyl pyrolidone), poly(lactic acid), poly glycolic acid (PGA), poly lactic-co-glycolic acid (PLGA), poly e-carpolactone (PCL), polyethylene oxide, poly propylene fumarate (PPF), poly acrylic acid (PAA), polyhydroxybutyric acid, hydrolysed polyacrylonitrile, polymethacrylic acid, polyethylene amine, esters of alginic acid; pectinic acid; and alginate, fully or partially oxidized alginate, hyaluronic acid, carboxy methyl cellulose, heparin, heparin sulfate, chitosan, carboxymethyl chitosan, chitin, pullulan, gellan, xanthan, collagen, gelatin, carboxymethyl starch, carboxymethyl dextran, chondroitin sulfate, cationic guar, cationic starch, and combinations thereof. In other embodiments, the biomaterial is selected from the group consisting of poly(L-lactide-co-glycolide) acid (PLGA), mesoporous silica, cryogel, and combinations thereof.

In one aspect, the present invention provides methods of treating a pathogen infection in a subject in need thereof. The methods comprise administering the vaccine composition of the present invention to the subject, thereby treating the pathogen infection in the subject.

In another aspect, the present invention provides methods of vaccinating a subject against a pathogen infection. The methods comprise administering the vaccine composition of the present invention to the subject, thereby vaccinating the subject against the pathogen infection.

In one aspect, the present invention provides methods of treating an antibiotic-resistant bacterial infection in a subject in need thereof. The methods comprise administering the vaccine composition of the present invention to the subject, thereby treating the antibiotic-resistant bacterial infection in the subject. In some embodiments, the vaccine composition is specific for the antibiotic-resistant bacterium in the subject.

In another aspect, the present invention provides methods of decreasing the level of a pathogen in a subject having a pathogen infection. The methods comprise administering the vaccine composition of the present invention to the subject, thereby decreasing the level of the pathogen in the subject.

In some embodiments, the level of the pathogen is decreased in an organ of the subject. In other embodiments, the organ is selected from the group consisting of a lung, a liver, a kidney, and a spleen.

In one aspect, the present invention provides methods of increasing the survival rate of a subject having a pathogen infection. The methods comprise administering the vaccine composition of the present invention to the subject, thereby increasing the survival rate of the subject.

In some embodiments, the subject is a mammal. In other embodiments, the mammal is selected from the group consisting of a human, an embryo, a horse, a dog, a cat, a cow, a sheep, a pig, a fish, an amphibian, a reptile, a goat, a bird, a monkey, a mouse, a rabbit, and a rat. In some embodiments, the mammal is a human.

In some embodiments, the infection is an acute infection. In other embodiments, the infection is a chronic infection.

In a further aspect, the present invention provides methods of producing a vaccine. The methods comprise contacting a sample comprising a pathogen or fragment thereof with an opsonin or a lectin, wherein the opsonin or lectin is capable of binding to the pathogen or fragment thereof in the sample, thereby forming an opsonin-bound or lectin-bound pathogen construct; isolating the opsonin-bound or lectin-bound pathogen construct from the sample; and combining the opsonin-bound or lectin-bound pathogen construct with a bioagent capable of recruiting an immune cell in a subject, thereby producing the vaccine.

In some embodiments, the pathogen is derived from a subject in vivo. In other embodiments, the pathogen comprises a pathogen-associated molecule pattern (PAMP). In some embodiments, the PAMP is selected from the group consisting of a pathogen fragment, a pathogen debris, a pathogen nucleic acid, a pathogen lipoprotein, a pathogen surface glycoprotein, a pathogen membrane component, and a released component from the pathogen.

In some embodiments, the pathogen is derived from an in vitro culture, a microorganism lysate, a crude lysate, or a purified lysate. In other embodiments, the pathogen is a synthetic pathogen.

In some embodiments, the bioagent comprises an adjuvant.

The present invention also provides vaccine compositions comprising a scaffold comprising a biomaterial and capable of recruiting and activating an immune cell in a subject; and an opsonin-bound or lectin-bound pathogen construct.

In some embodiments, the biomaterial is selected from the group consisting of glycosaminoglycan, silk, fibrin, MATRIGEL®, poly-ethyleneglycol (PEG), polyhydroxy ethyl methacrylate, polyvinyl alcohol, polyacrylamide, poly (N-vinyl pyrolidone), poly(lactic acid), poly glycolic acid (PGA), poly lactic-co-glycolic acid (PLGA), poly e-carpolactone (PCL), polyethylene oxide, poly propylene fumarate (PPF), poly acrylic acid (PAA), polyhydroxybutyric acid, hydrolysed polyacrylonitrile, polymethacrylic acid, polyethylene amine, esters of alginic acid; pectinic acid; and alginate, fully or partially oxidized alginate, hyaluronic acid, carboxy methyl cellulose, heparin, heparin sulfate, chitosan, carboxymethyl chitosan, chitin, pullulan, gellan, xanthan, collagen, gelatin, carboxymethyl starch, carboxymethyl dextran, chondroitin sulfate, cationic guar, cationic starch, and combinations thereof. In other embodiments, the biomaterial is selected from the group consisting of poly(L-lactide-co-glycolide) acid (PLGA), mesoporous silica, cryogel, and combinations thereof.

In some embodiments, the scaffold further comprises a bioagent. In other embodiments, the bioagent is capable of recruiting the immune cell in the subject.

In some embodiments, the bioagent is selected from the group consisting of interleukin (IL)-1, IL-2, IL-3, IL-4, IL-5, IL-6, IL-7, IL-8, IL-10, IL-12, IL-15, IL-17, IL-18, tumor necrosis factor (TNF)-alpha, interferon (IFN)-gamma, IFN-alpha, granulocyte macrophage colony stimulating factor (GM-CSF), granulocyte colony stimulating factor (G-CSF), Fms-related tyrosine kinase ligand (FTL)-3 ligand, CCL19, CCL21, M-SCF, MIF, CD40L, CD3, ICAM, transforming growth factor (TGF)-beta, cytosine-guanosine oligonucleotide (CpG-ODN), lipopolysaccharides (LPS), Fas ligand, Trail, lymphotactin, Mannan (M-FP), APG-2, Hsp70 and Hsp90.

In some embodiments, the bioagent comprises an adjuvant. In other embodiments, the adjuvant is selected from the group consisting of cytosine-guanosine oligonucleotide (CpG-ODN) sequence, granulocyte macrophage colony stimulating factor (GM-CSF), ovalbumin (OVA), monophosphoryl lipid A (MPL), poly(I:C), MF59, alum, aluminum hydroxide, aluminum phosphate, calcium phosphate hydroxide, Quil A, N-acetyl muramyl-L-alanyl-D-isoglutamine (MDP), FIA, montanide, adjuvant 65, lipovant, poly (DL-lactide-coglycolide) microspheres, paraffin oil, squalene, virosome, AS03, AS04, IL-1, IL-3, IL-4, IL-5, IL-6, IL-7, IL-8, IL-10, IL-12, IL-15, IL-17, IL-18, STING, Toll-like receptor ligand, CD40L, pathogen-associated molecular patterns (PAMPs), damage-associated molecular pattern molecules (DAMPs), Freund's complete adjuvant, Freund's incomplete adjuvant, antibodies against immune suppressive molecules (e.g., antibody or antagonist against transforming growth factor (TGF)-beta, A2aR antagonists), lipopolysaccharides (LPS), Fas ligand, Trail, lymphotactin, Mannan (M-FP), APG-2, Hsp70 and Hsp90.

In some embodiments, the lectin-bound pathogen construct comprises a lectin, a portion of a lectin, an engineered lectin or a portion thereof. In some embodiments, the lectin is a collectin. In other embodiments, the lectin is a ficolin. In some embodiments, the lectin is a mannose-binding lectin (MBL). In other embodiments, the lectin comprises amino acid residues 81 to 228 of MBL (SEQ ID NO: 1). In yet another embodiment, the lectin comprises amino acid residues 111 to 228 of MBL. In some embodiments, the mannose-binding lectin (MBL) is capable of binding to the pathogen. In some embodiments, the lectin is Surface Protein D (SPD). In other embodiments, the Surface Protein D (SPD) is capable of binding to the pathogen.

In some embodiments, the opsonin-bound or lectin-bound pathogen construct further comprises an immunoglobulin (IgG) Fc portion.

In some embodiments, the opsonin-bound or lectin-bound pathogen construct further comprises a solid substrate. In other embodiments, the solid substrate is selected from the group consisting of a magnetic bead, a microporous membrane, a hollow-fiber reactor, a blood filtration membrane and a blood flow device. In some embodiments, the solid substrate is a magnetic bead. In other embodiments, the pathogen is present on the solid substrate at a quantity of about 1 pg to about 1000 µg.

In some embodiments, the pathogen is an infectious microorganism selected from the group consisting of a bacterium, a fungus, a virus and a parasite, or a fragment thereof.

In some embodiments, the bacterium is selected from the group consisting of *Acinetobacter baumanii, Burkholderia cepacia, Bacterioides fragilis, Chlamydia trachomatis, Citrobacter freundii, Campylobacter jejuni, Escherichia coli, Enterobacter aerogenes, Enterobacter cloacae, Haemophilus inf* b, *Helicobacter pylori, Klebsiella oxytoca, K. pneumonia* (MDR/CRE), *Legionella pneumophila, Neisseria meningitides, Neisseria gonorrhoeae, Pseudomonas aeruginosa, Salmonella typhi, paratyphi, typhimurium, Serratia marcescens, Shigella flexneri, Stenotrophomonas maltophilia, Yersinia pseudotuberculosis, Bacillus subtilis, Clostridium neoformans, C. difficile, C. perfringens, Corynebacterium* spp, *Enterococcus faecalis, Enterococcus faecium,* vancomycin-resistant *Enterococci* (VRE), *Listeria monocytogenes, Mycobactrium avium, M. tuberculosis, M. leprae, Nocardia farcinica, P. acnes, Staphylococcus aureus,* methicillin-susceptible *Staphylococcus aureus* (MSSA), methicillin-resistant *Staphylococcus aureus* (MRSA), *Staphylococcus epidermidis, Streptococcus pyogenes,* Strep Group A, Strep Group B (agalactiae) and Strep Group C.

In some embodiments, the bacterium is an antibiotic-resistant bacterium. In some embodiment, the bacterium is a multi-drug resistant bacterium. In other embodiments, the antibiotic-resistant bacterium or the multi-drug resistant bacterium is selected from the group consisting of *Acinetobacter baumanii, Escherichia coli, Klebsiella oxytoca, K. pneumonia* (MDR/CRE), *Pseudomonas aeruginosa, C. difficile,* vancomycin-resistant *Enterococci* (VRE) and methicillin-resistant *Staphylococcus aureus* (MRSA).

In some embodiments, the fungus is selected from the group consisting of *Aspergillus* spp, *Blastomyces, Candida albicans, glabrata, guilliermondii, krusei, parapsilosis, tropicalis Cryptococcus, Fusarium* spp., *Mucor* spp., *Saccharomyces,* and *Pneumocystis jirovecii (carinii).*

In some embodiments, the virus is selected from the group consisting of Dengue virus, Ebola virus, EBV, Hepitis A virus, Hepitis B virus, Hepitis C virus, Hepitis D virus, HIV, HSV 1, HSV 2, Cytomegalovirus (CMV), Influenza A virus, Marburg virus, Human respiratory syncytial virus (RSV), SARS-CoV, West Nile virus, Human papillomavirus (HPV), Human rhinoviruses (HRVs), and Zica virus.

In some embodiments, the parasite is selected from the group consisting of *Cryptosporidium, Leishmania, Malaria, Schistosoma, Trichomonasm* and *Trypanosoma.*

In some embodiments, the pathogen comprises a cell wall component of the infectious microorganism. In other embodiments, the pathogen comprises the whole infectious microbial cell. In some embodiments, the cell wall components of the infectious microorganism are glycosylated. In other embodiments, the cell wall components are mannosylated. In some embodiments, the cell wall components are mannose-capped lipoarabinomannan (ManLAM). In other embodiments, the cell wall components are phosphatidylinositol mannoside (PIM).

In some embodiments, the pathogen comprises a cell wall component of the infectious microorganism. In other embodiments, the pathogen comprises the whole infectious microbial cell. In some embodiments, the cell wall components of the infectious microorganism are glycosylated. In other embodiments, the cell wall components are mannosylated. In some embodiments, the cell wall components are mannose-capped lipoarabinomannan (ManLAM). In other embodiments, the cell wall components are phosphatidylinositol mannoside (PIM).

In some embodiments, the pathogen is a mycoplasma. In other embodiments, the mycoplasma is selected from the group consisting of *M. pneumoniae, M. hominis* and *M. orale.*

In some embodiments, the pathogen comprises a pathogen-associated molecule pattern (PAMP). In other embodiments, the PAMP is selected from the group consisting of a pathogen fragment, a pathogen debris, a pathogen nucleic acid, a pathogen lipoprotein, a pathogen surface glycoprotein, a pathogen membrane component, and a component released from the pathogen.

In some embodiments, the component released from the pathogen comprises a toxin. In other embodiments, the toxin is selected from the group consisting of endotoxin, lipopolysaccharide (LPS), lipoteichoic acid (LTA), wall teichoic acid (WTA) and Ricin.

In some embodiments, the pathogen is in a sample derived from a subject in vivo. In other embodiments, the sample is selected from the group consisting of a blood sample, a plasma sample, a serum sample, a blood culture sample, a cerebrospinal fluid sample, a joint fluid sample, a urine sample, a semen sample, a saliva sample, a sputum sample, a bronchial fluid sample, and a tear sample.

In some embodiments, the pathogen is derived from an in vitro culture, a microorganism lysate, a crude lysate, or a purified lysate. In some embodiments, the pathogen is a synthetic pathogen.

In some embodiments, the pathogen is neutralized. In other embodiments, the pathogen is neutralized by treatment with antibiotics, ultraviolet light, sonication, microwave, bead mill, x-ray, autoclave, irradiation or mechanical disruption. In some embodiments, the pathogen is non-infectious after neutralization.

In some embodiments, the immune cell is an antigen-presenting cell. In other embodiments, the immune cell is selected from the group consisting of a dendritic cell, a macrophage, a T cell and a B cell.

In some embodiments, the vaccine composition comprises at least two different types of pathogen. In other embodiments, the vaccine composition comprises at least three different types of pathogen. In some embodiments, the vaccine composition is capable of targeting against different species of a pathogen.

In some embodiments, the vaccine composition is suitable for implantation in a subject. In other embodiments, the vaccine composition is suitable for subcutaneous implantation. In some embodiments, the vaccine composition is suitable for injection in a subject. In other embodiments, the vaccine composition is suitable for oral administration in a subject. In another embodiment, the vaccine composition is in the form of a pill, a tablet, a capsule, a soft gel, a chewable, a powder, an emulsion, or an aqueous solution.

In some embodiments, the vaccine composition is lyophilized. In other embodiments, the vaccine composition has a shelf life of about 30 days to about 1 year. In some embodiments, the vaccine composition has a shelf life of at least 1 year. In other embodiments, the vaccine composition is capable of being stored at room temperature. In some embodiments, the vaccine composition is portable.

In some embodiments, the vaccine composition is capable of immobilizing the opsonin-bound or lectin-bound pathogen construct and preventing leakage of the opsonin-bound or lectin-bound pathogen construct from the scaffold.

In some embodiments, the subject is a mammal. In other embodiments, the mammal is selected from the group consisting of a human, an embryo, a horse, a dog, a cat, a cow, a sheep, a pig, a fish, an amphibian, a reptile, a goat, a bird, a monkey, a mouse, a rabbit, and a rat. In some embodiments, the mammal is a human.

In one aspect, the present invention provides stable scaffold compositions. The stable scaffold compositions comprise a biomaterial and capable of recruiting and activating an immune cell in a subject, wherein the scaffold is lyophilized, and wherein the scaffold has a shelf life of about 30 days to about 1 year.

In some embodiments, the biomaterial is selected from the group consisting of glycosaminoglycan, silk, fibrin, MATRIGEL®, poly-ethyleneglycol (PEG), polyhydroxy ethyl methacrylate, polyvinyl alcohol, polyacrylamide, poly (N-vinyl pyrolidone), poly(lactic acid), poly glycolic acid (PGA), poly lactic-co-glycolic acid (PLGA), poly e-carpolactone (PCL), polyethylene oxide, poly propylene fumarate (PPF), poly acrylic acid (PAA), polyhydroxybutyric acid, hydrolysed polyacrylonitrile, polymethacrylic acid, polyethylene amine, esters of alginic acid; pectinic acid; and alginate, fully or partially oxidized alginate, hyaluronic acid, carboxy methyl cellulose, heparin, heparin sulfate, chitosan, carboxymethyl chitosan, chitin, pullulan, gellan, xanthan, collagen, gelatin, carboxymethyl starch, carboxymethyl dextran, chondroitin sulfate, cationic guar, cationic starch, and combinations thereof. In other embodiments, the biomaterial is selected from the group consisting of poly(L-lactide-co-glycolide) acid (PLGA), mesoporous silica, cryogel, and combinations thereof.

In some embodiments, the scaffold further comprises a bioagent. In some embodiments, the bioagent is capable of recruiting the immune cell in the subject.

In some embodiments, the bioagent is selected from the group consisting of interleukin (IL)-1, IL-2, IL-3, IL-4, IL-5, IL-6, IL-7, IL-8, IL-10, IL-12, IL-15, IL-17, IL-18, tumor necrosis factor (TNF)-alpha, interferon (IFN)-gamma, IFN-alpha, granulocyte macrophage colony stimulating factor (GM-CSF), granulocyte colony stimulating factor (G-CSF), Fms-related tyrosine kinase ligand (FTL)-3 ligand, CCL19, CCL21, M-SCF, MIF, CD40L, CD3, ICAM, transforming growth factor (TGF)-beta, cytosine-guanosine oligonucleotide (CpG-ODN), lipopolysaccharides (LPS), Fas ligand, Trail, lymphotactin, Mannan (M-FP), APG-2, Hsp70 and Hsp90.

In some embodiments, the bioagent comprises an adjuvant. In other embodiments, the adjuvant is selected from the group consisting of cytosine-guanosine oligonucleotide (CpG-ODN) sequence, granulocyte macrophage colony stimulating factor (GM-CSF), ovalbumin (OVA), monophosphoryl lipid A (MPL), poly(I:C), MF59, alum, aluminum hydroxide, aluminum phosphate, calcium phosphate hydroxide, Quil A, N-acetyl muramyl-L-alanyl-D-isoglutamine (MDP), FIA, montanide, adjuvant 65, lipovant, poly (DL-lactide-coglycolide) microspheres, paraffin oil, squalene, virosome, AS03, AS04, IL-1, IL-3, IL-4, IL-5, IL-6, IL-7, IL-8, IL-10, IL-12, IL-15, IL-17, IL-18, STING, Toll-like receptor ligand, CD40L, pathogen-associated molecular patterns (PAMPs), damage-associated molecular pattern molecules (DAMPs), Freund's complete adjuvant, Freund's incomplete adjuvant, antibodies against immune suppressive molecules (e.g., antibody or antagonist against transforming growth factor (TGF)-beta, A2aR antagonists), lipopolysaccharides (LPS), Fas ligand, Trail, lymphotactin, Mannan (M-FP), APG-2, Hsp70 and Hsp90. In certain embodiments, the adjuvant comprises granulocyte macrophage colony stimulating factor (GM-CSF). In certain embodiments, the adjuvant comprises a polyehylenimine (PEI)-CpG-ODN sequence.

In some embodiments, the immune cell is an antigen-presenting cell. In other embodiments, the immune cell is selected from the group consisting of a dendritic cell, a macrophage, a T cell and a B cell.

In some embodiments, the scaffold composition is suitable for implantation in a subject. In other embodiments, the scaffold composition is suitable for subcutaneous implantation. In some embodiments, the scaffold composition is suitable for injection in a subject. In other embodiments, the scaffold composition is suitable for oral administration in a subject. In some embodiments, the scaffold composition is in the form of a pill, a tablet, a capsule, a soft gel, a chewable, a powder, an emulsion, or an aqueous solution.

In some embodiments, the subject is a mammal. In other embodiments, the mammal is selected from the group consisting of a human, an embryo, a horse, a dog, a cat, a cow, a sheep, a pig, a fish, an amphibian, a reptile, a goat, a bird, a monkey, a mouse, a rabbit, and a rat. In some embodiments, the mammal is a human.

In some embodiments, the scaffold composition is capable of being stored at room temperature. In some embodiments, the scaffold composition is portable.

In another aspect, the present invention provides scaffold compositions comprising a biomaterial and capable of recruiting and activating an immune cell in a subject, wherein the scaffold comprises a solid substrate, and wherein the solid substrate is suitable for attachment of a pathogen.

In some embodiments, the solid substrate is selected from the group consisting of a magnetic bead, a microporous membrane, a hollow-fiber reactor, a blood filtration membrane and a blood flow device. In some embodiments, the solid substrate is a magnetic bead. In other embodiments, the pathogen is present on the solid substrate at a quantity of about 1 pg to about 1000 µg.

In some embodiments, the biomaterial is selected from the group consisting of glycosaminoglycan, silk, fibrin, MATRIGEL®, poly-ethyleneglycol (PEG), polyhydroxy ethyl methacrylate, polyvinyl alcohol, polyacrylamide, poly (N-vinyl pyrolidone), poly(lactic acid), poly glycolic acid (PGA), poly lactic-co-glycolic acid (PLGA), poly e-carpolactone (PCL), polyethylene oxide, poly propylene fumarate (PPF), poly acrylic acid (PAA), polyhydroxybutyric acid, hydrolysed polyacrylonitrile, polymethacrylic acid, polyethylene amine, esters of alginic acid; pectinic acid; and alginate, fully or partially oxidized alginate, hyaluronic acid, carboxy methyl cellulose, heparin, heparin sulfate, chitosan, carboxymethyl chitosan, chitin, pullulan, gellan, xanthan, collagen, gelatin, carboxymethyl starch, carboxymethyl dextran, chondroitin sulfate, cationic guar, cationic starch, and combinations thereof. In other embodiments, the biomaterial is selected from the group consisting of poly(L-lactide-co-glycolide) acid (PLGA), mesoporous silica, cryogel, and combinations thereof.

In some embodiments, the scaffold further comprises a bioagent. In some embodiments, the bioagent is capable of recruiting the immune cell in the subject.

In some embodiments, the bioagent is selected from the group consisting of interleukin (IL)-1, IL-2, IL-3, IL-4, IL-5, IL-6, IL-7, IL-8, IL-10, IL-12, IL-15, IL-17, IL-18, tumor necrosis factor (TNF)-alpha, interferon (IFN)-gamma, IFN-alpha, granulocyte macrophage colony stimulating factor (GM-CSF), granulocyte colony stimulating factor (G-CSF), Fms-related tyrosine kinase ligand (FTL)-3 ligand, CCL19, CCL21, M-SCF, MIF, CD40L, CD3, ICAM, transforming growth factor (TGF)-beta, cytosine-guanosine oligonucleotide (CpG-ODN), lipopolysaccharides (LPS), Fas ligand, Trail, lymphotactin, Mannan (M-FP), APG-2, Hsp70 and Hsp90.

In some embodiments, the bioagent comprises an adjuvant. In other embodiments, the adjuvant is selected from the group consisting of cytosine-guanosine oligonucleotide (CpG-ODN) sequence, granulocyte macrophage colony stimulating factor (GM-CSF), ovalbumin (OVA), monophosphoryl lipid A (MPL), poly(I:C), MF59, alum, aluminum hydroxide, aluminum phosphate, calcium phosphate hydroxide, Quil A, N-acetyl muramyl-L-alanyl-D-isoglutamine (MDP), FIA, montanide, adjuvant 65, lipovant, poly (DL-lactide-coglycolide) microspheres, paraffin oil, squalene, virosome, AS03, AS04, IL-1, IL-3, IL-4, IL-5, IL-6, IL-7, IL-8, IL-10, IL-12, IL-15, IL-17, IL-18, STING, Toll-like receptor ligand, CD40L, pathogen-associated molecular patterns (PAMPs), damage-associated molecular pattern molecules (DAMPs), Freund's complete adjuvant, Freund's incomplete adjuvant, antibodies against immune suppressive molecules (e.g., antibody or antagonist against transforming growth factor (TGF)-beta, A2aR antagonists), lipopolysaccharides (LPS), Fas ligand, Trail, lymphotactin, Mannan (M-FP), APG-2, Hsp70 and Hsp90. In certain embodiments, the adjuvant comprises granulocyte macrophage colony stimulating factor (GM-CSF). In certain embodiments, the adjuvant comprises a polyehylenimine (PEI)-CpG-ODN sequence.

In some embodiments, the immune cell is an antigen-presenting cell. In other embodiments, the immune cell is selected from the group consisting of a dendritic cell, a macrophage, a T cell and a B cell.

In some embodiments, the scaffold composition is suitable for implantation in a subject. In other embodiments, the scaffold composition is suitable for subcutaneous implantation. In some embodiments, the scaffold composition is suitable for injection in a subject. In other embodiments, the scaffold composition is suitable for oral administration in a subject. In some embodiments, the scaffold composition is in the form of a pill, a tablet, a capsule, a soft gel, a chewable, a powder, an emulsion, or an aqueous solution.

In some embodiments, the subject is a mammal. In other embodiments, the mammal is selected from the group consisting of a human, an embryo, a horse, a dog, a cat, a cow, a sheep, a pig, a fish, an amphibian, a reptile, a goat, a bird, a monkey, a mouse, a rabbit, and a rat. In some embodiments, the mammal is a human.

In some embodiments, the scaffold composition is lyophilized. In other embodiments, the scaffold composition has a shelf life of about 30 days to about 1 year. In some embodiments, the scaffold composition has a shelf life of at least 1 year. In other embodiments, the scaffold composition is capable of being stored at room temperature. In some embodiments, the scaffold composition is portable.

In some embodiments, the pathogen is an infectious microorganism selected from the group consisting of a bacterium, a fungus, a virus and a parasite, or a fragment thereof.

In some embodiments, the pathogen comprises a pathogen-associated molecule pattern (PAMP). In other embodiments, the PAMP is selected from the group consisting of a pathogen fragment, a pathogen debris, a pathogen nucleic acid, a pathogen lipoprotein, a pathogen surface glycoprotein, a pathogen membrane component, and a component released from the pathogen.

In some embodiments, the component released from the pathogen comprises a toxin. In other embodiments, the toxin is selected from the group consisting of endotoxin, lipopolysaccharide (LPS), lipoteichoic acid (LTA), wall teichoic acid (WTA) and Ricin.

In some embodiments, the pathogen is in a sample derived from a subject in vivo. In other embodiments, the sample is selected from the group consisting of a blood sample, a plasma sample, a serum sample, a blood culture sample, a cerebrospinal fluid sample, a joint fluid sample, a urine sample, a semen sample, a saliva sample, a sputum sample, a bronchial fluid sample, and a tear sample.

In some embodiments, the pathogen is derived from an in vitro culture, a microorganism lysate, a crude lysate, or a purified lysate. In some embodiments, the pathogen is a synthetic pathogen.

In one aspect, the present invention provides a recombinant opsonin or lectin suitable for binding a pathogen or fragment thereof derived from a subject, wherein the opsonin or lectin comprises a pulmonary surfactant. In some embodiments, the pulmonary surfactant is surfactant protein D (SPD).

In another aspect, the present invention provides an opsonin-bound or lectin-bound pathogen constructs. The opsonin-bound or lectin-bound pathogen constructs comprise a pathogen or fragment thereof derived from a subject bound to an opsonin or a lectin, wherein the opsonin or lectin comprises a pulmonary surfactant. In some embodiments, the pulmonary surfactant is surfactant protein D (SPD).

In another aspect, the present invention provides stable opsonin-bound or lectin-bound pathogen constructs. The stable opsonin-bound or lectin-bound pathogen constructs comprise a pathogen or fragment thereof derived from a subject bound to an opsonin, wherein the opsonin-bound or lectin-bound pathogen construct is lyophilized, and wherein the opsonin-bound or lectin-bound pathogen construct has a shelf life of about 30 days to about 1 year.

In some embodiments, the lectin-bound pathogen construct comprises a lectin or a portion of a lectin, an engineered lection or a portion thereof. In some embodiments, the lectin is a collectin. In other embodiments, the lectin is a ficollin. In some embodiments, the lectin is a mannose-binding lectin (MBL). In other embodiments, the lectin comprises amino acid residues 81 to 228 of MBL (SEQ ID NO: 1). In yet another embodiment, the lectin comprises amino acid residues 111 to 228 of MBL. In some embodiments, the mannose-binding lectin (MBL) is capable of binding to the pathogen. In some embodiments, the lectin is Surface Protein D (SPD). In other embodiments, the Surface Protein D (SPD) is capable of binding to the pathogen.

In some embodiments, the opsonin-bound or lectin-bound pathogen construct further comprises an immunoglobulin (IgG) Fc portion.

In some embodiments, the opsonin-bound or lectin-bound pathogen construct further comprises a solid substrate. In other embodiments, the solid substrate is selected from the group consisting of a magnetic bead, a microporous membrane, a hollow-fiber reactor, a blood filtration membrane and a blood flow device. In some embodiments, the solid substrate is a magnetic bead. In other embodiments, the pathogen is present on the solid substrate at a quantity of about 1 pg to about 1000 µg.

In some embodiments, the pathogen is an infectious microorganism selected from the group consisting of a bacterium, a fungus, a virus and a parasite, or a fragment thereof.

In some embodiments, the bacterium is selected from the group consisting of *Acinetobacter baumanii, Burkholderia cepacia, Bacterioides fragilis, Chlamydia trachomatis, Citrobacter freundii, Campylobacter jejuni, Escherichia coli, Enterobacter aerogenes, Enterobacter cloacae, Haemophilus inf* b, *Helicobacter pylori, Klebsiella oxytoca, K. pneumonia* (MDR/CRE), *Legionella pneumophila, Neisseria meningitides, Neisseria gonorrhoeae, Pseudomonas aeruginosa, Salmonella typhi, paratyphi, typhimurium, Serratia marcescens, Shigella flexneri, Stenotrophomonas maltophilia, Yersinia pseudotuberculosis, Bacillus subtilis, Clostridium neoformans, C. difficile, C. perfringens, Corynebacterium spp, Enterococcus faecalis, Enterococcus faecium*, vancomycin-resistant *Enterococci* (VRE), *Listeria monocytogenes, Mycobactrium avium, M. tuberculosis, M. leprae, Nocardia farcinica, P. acnes, Staphylococcus aureus*, methicillin-susceptible *Staphylococcus aureus* (MSSA), methicillin-resistant *Staphylococcus aureus* (MRSA), *Staphylococcus epidermidis, Streptococcus pyogenes*, Strep Group A, Strep Group B (agalactiae) and Strep Group C.

In some embodiments, the bacterium is an antibiotic-resistant bacterium. In some embodiment, the bacterium is a multi-drug resistant bacterium. In other embodiments, the antibiotic-resistant bacterium or the multi-drug resistant bacterium is selected from the group consisting of *Acinetobacter baumanii, Escherichia coli, Klebsiella oxytoca, K. pneumonia* (MDR/CRE), *Pseudomonas aeruginosa, C. difficile*, vancomycin-resistant *Enterococci* (VRE) and methicillin-resistant *Staphylococcus aureus* (MRSA).

In some embodiments, the fungus is selected from the group consisting of *Aspergillus* spp, *Blastomyces, Candida albicans, glabrata, guilliermondii, krusei, parapsilosis, tropicalis Cryptococcus, Fusarium* spp., *Mucor* spp., *Saccharomyces*, and *Pneumocystis jirovecii (carinii)*.

In some embodiments, the virus is selected from the group consisting of Dengue virus, Ebola virus, EBV, Hepitis A virus, Hepitis B virus, Hepitis C virus, Hepitis D virus, HIV, HSV 1, HSV 2, Cytomegalovirus (CMV), Influenza A virus, Marburg virus, Human respiratory syncytial virus (RSV), SARS-CoV, West Nile virus, Human papillomavirus (HPV), Human rhinoviruses (HRVs), and Zica virus.

In some embodiments, the parasite is selected from the group consisting of *Cryptosporidium, Leishmania, Malaria, Schistosoma, Trichomonasm* and *Trypanosoma*.

In some embodiments, the pathogen is a mycoplasma. In other embodiments, the mycoplasma is selected from the group consisting of *M. pneumoniae, M. hominis* and *M. orale*.

In some embodiments, the pathogen comprises a cell wall component of the infectious microorganism. In other embodiments, the pathogen comprises the whole infectious microbial cell. In some embodiments, the cell wall components of the infectious microorganism are glycosylated. In other embodiments, the cell wall components are mannosylated. In some embodiments, the cell wall components are mannose-capped lipoarabinomannan (ManLAM). In other embodiments, the cell wall components are phosphatidylinositol mannoside (PIM).

In some embodiments, the pathogen comprises a pathogen-associated molecule pattern (PAMP). In other embodiments, the PAMP is selected from the group consisting of a pathogen fragment, a pathogen debris, a pathogen nucleic acid, a pathogen lipoprotein, a pathogen surface glycoprotein, a pathogen membrane component, and a component released from the pathogen.

In some embodiments, the component released from the pathogen comprises a toxin. In other embodiments, the toxin is selected from the group consisting of endotoxin, lipopolysaccharide (LPS), lipoteichoic acid (LTA), wall teichoic acid (WTA) and Ricin.

In some embodiments, the pathogen is in a sample derived from a subject in vivo. In other embodiments, the sample is selected from the group consisting of a blood sample, a plasma sample, a serum sample, a blood culture sample, a cerebrospinal fluid sample, a joint fluid sample, a urine sample, a semen sample, a saliva sample, a sputum sample, a bronchial fluid sample, and a tear sample.

In some embodiments, the pathogen is derived from an in vitro culture, a microorganism lysate, a crude lysate, or a purified lysate. In some embodiments, the pathogen is a synthetic pathogen.

In some embodiments, the pathogen is neutralized. In other embodiments, the pathogen is neutralized by treatment with antibiotics, ultraviolet light, sonication, microwave, bead mill, x-ray, autoclave, irradiation or mechanical disruption. In some embodiments, the pathogen is non-infectious after neutralization.

In some embodiments, the immune cell is an antigen-presenting cell. In other embodiments, the immune cell is selected from the group consisting of a dendritic cell, a macrophage, a T cell and a B cell.

In some embodiments, the opsonin-bound or lectin-bound pathogen construct comprises at least two different types of pathogen. In other embodiments, the opsonin-bound or lectin-bound pathogen construct comprises at least three different types of pathogen. In some embodiments, the opsonin-bound or lectin-bound pathogen construct is capable of targeting against different species of a pathogen.

In some embodiments, the opsonin-bound or lectin-bound pathogen construct is suitable for implantation in a subject. In other embodiments, the opsonin-bound or lectin-bound pathogen construct is suitable for subcutaneous implantation. In some embodiments, the opsonin-bound or lectin-bound pathogen construct is suitable for injection in a subject. In other embodiments, the opsonin-bound or lectin-bound pathogen construct is suitable for oral administration in a subject. In another embodiment, the vaccine composition is in the form of a pill, a tablet, a capsule, a soft gel, a chewable, a powder, an emulsion, or an aqueous solution.

In some embodiments, the opsonin-bound or lectin-bound pathogen construct is lyophilized. In other embodiments, the opsonin-bound or lectin-bound pathogen construct has a shelf life of about 30 days to about 1 year. In some embodiments, the opsonin-bound or lectin-bound pathogen construct has a shelf life of at least 1 year. In other embodiments, the opsonin-bound or lectin-bound pathogen construct is capable of being stored at room temperature. In some embodiments, the opsonin-bound or lectin-bound pathogen construct is portable.

In some embodiments, the subject is a mammal. In other embodiments, the mammal is selected from the group consisting of a human, an embryo, a horse, a dog, a cat, a cow, a sheep, a pig, a fish, an amphibian, a reptile, a goat, a bird, a monkey, a mouse, a rabbit, and a rat. In some embodiments, the mammal is a human.

The present invention also provides methods of treating a pathogen infection in a subject in need thereof. The methods comprise administering the vaccine composition of the present invention to the subject, thereby treating the pathogen infection in the subject.

In one aspect, the present invention provides methods of vaccinating a subject against a pathogen infection. The methods comprise administering the vaccine composition of the present invention to the subject, thereby vaccinating the subject against the pathogen infection.

In another aspect, the present invention provides methods of treating an antibiotic-resistant bacterial infection in a subject in need thereof. The methods comprise administering the vaccine composition of the present invention to the subject, thereby treating the antibiotic-resistant bacterial infection in the subject. In some embodiments, the vaccine composition is specific for the antibiotic-resistant bacterium in the subject.

In one aspect, the present invention provides methods of decreasing the level of a pathogen in a subject having a pathogen infection. The methods comprise administering the vaccine composition of the present invention to the subject, thereby decreasing the level of the pathogen in the subject.

In some embodiments, the level of the pathogen is decreased in an organ of the subject. In some embodiments, the organ is selected from the group consisting of a lung, a liver, a kidney, and a spleen.

In one aspect, the present invention provides methods of increasing the survival rate of a subject having a pathogen infection. The methods comprise administering the vaccine composition of the present invention to the subject, thereby increasing the survival rate of the subject.

In another aspect, the present invention provides methods of reducing the level of pain associated with a pathogen infection in a subject in need thereof. The methods comprise administering the vaccine composition of the present invention to the subject, thereby reducing the level of pain associated with a pathogen infection in the subject.

In yet another aspect, the present invention provides methods of reducing the level of distress associated with a pathogen infection in a subject in need thereof. The methods comprise administering the vaccine composition of the present invention to the subject, thereby reducing the level of distress associated with a pathogen infection in the subject.

In some embodiments, the subject is a mammal. In other embodiments, the mammal is selected from the group consisting of a human, an embryo, a horse, a dog, a cat, a cow, a sheep, a pig, a fish, an amphibian, a reptile, a goat, a bird, a monkey, a mouse, a rabbit, and a rat. In some embodiments, the mammal is a human.

In some embodiments, the infection is an acute infection. In other embodiments, the infection is a chronic infection.

In one aspect, the present invention provides methods of treating a pathogen infection in a subject in need thereof. The methods comprise administering the scaffold composition of the present invention and the opsonin-bound or lectin-bound pathogen construct of the present invention to the subject, thereby treating the pathogen infection in the subject.

In another aspect, the present invention provides methods of vaccinating a subject against a pathogen infection. The methods comprise administering the scaffold composition of the present invention and the opsonin-bound or lectin-bound pathogen construct of the present invention to the subject, thereby vaccinating the subject against the pathogen infection.

In one aspect, the present invention provides methods of treating an antibiotic-resistant bacterial infection in a subject in need thereof. The methods comprise administering the scaffold composition of the present invention and the opsonin-bound or lectin-bound pathogen construct of the present invention to the subject, thereby treating the antibiotic-resistant bacterial infection in the subject. In some embodiments, the opsonin-bound or lectin-bound pathogen construct is specific for the antibiotic-resistant bacterium in the subject.

In another aspect, the present invention provides methods of decreasing the level of a pathogen in a subject having a pathogen infection. The methods comprise administering the scaffold composition of the present invention and the opsonin-bound or lectin-bound pathogen construct of the present invention to the subject, thereby decreasing the level of the pathogen in the subject.

In some embodiments, the level of the pathogen is decreased in an organ of the subject. In some embodiments, the organ is selected from the group consisting of a lung, a liver, a kidney, and a spleen.

In one aspect, the present invention provides methods of increasing survival rate of a subject having a pathogen infection. The methods comprise administering the scaffold composition of the present invention and the opsonin-bound or lectin-bound pathogen construct of the present invention to the subject, thereby increasing the survival rate of the subject.

In another aspect, the present invention provides methods of reducing the level of pain associated with a pathogen infection in a subject in need thereof. The methods comprise administering the scaffold composition of the present invention and the opsonin-bound or lectin-bound pathogen construct of the present invention to the subject, thereby reducing the level of pain associated with a pathogen infection in the subject.

In yet another aspect, the present invention provides methods of reducing the level of distress associated with a pathogen infection in a subject in need thereof. The methods comprise administering the scaffold composition of the present invention and the opsonin-bound or lectin-bound pathogen construct of the present invention to the subject, thereby reducing the level of distress associated with a pathogen infection in the subject.

In some embodiments, the scaffold composition of the present invention and the opsonin-bound or lectin-bound pathogen construct of the present invention are administered simultaneously to the subject. In other embodiments, the scaffold composition of the present invention is administered to the subject prior to the opsonin-bound or lectin-bound pathogen construct of the present invention. In yet another embodiment, the scaffold composition of the present invention is administered to the subject after the opsonin-bound or lectin-bound pathogen construct of the present invention.

In some embodiments, the subject is a mammal. In other embodiments, the mammal is selected from the group consisting of a human, an embryo, a horse, a dog, a cat, a cow, a sheep, a pig, a fish, an amphibian, a reptile, a goat, a bird, a monkey, a mouse, a rabbit, and a rat. In some embodiments, the mammal is a human.

In some embodiments, the infection is an acute infection. In other embodiments, the infection is a chronic infection.

In one aspect, the present invention provides methods of producing a vaccine. The methods comprise contacting a sample comprising a pathogen or fragment thereof with an opsonin or a lectin, wherein the opsonin or the lectin is capable of binding to a pathogen or fragment thereof in the sample, thereby forming an opsonin-bound or lectin-bound pathogen construct; isolating the opsonin-bound or lectin-bound pathogen construct from the sample; and combining the isolated opsonin-bound or lectin-bound pathogen construct with a scaffold, thereby producing the vaccine.

In some embodiments, the pathogen is derived from a subject in vivo. In some embodiments, the pathogen is derived from an in vitro culture, a microorganism lysate, a crude lysate, or a purified lysate. In some embodiments, the pathogen is a synthetic pathogen.

In some embodiments, the pathogen comprises a pathogen-associated molecule pattern (PAMP). In some embodiments, the PAMP is selected from the group consisting of a pathogen fragment, a pathogen debris, a pathogen nucleic acid, a pathogen lipoprotein, a pathogen surface glycoprotein, a pathogen membrane component, and a released component from the pathogen.

In some embodiments, the pathogen comprises a cell wall component of the infectious microorganism. In other embodiments, the pathogen comprises the whole infectious microbial cell. In some embodiments, the cell wall components of the infectious microorganism are glycosylated. In other embodiments, the cell wall components are mannosylated. In some embodiments, the cell wall components are mannose-capped lipoarabinomannan (ManLAM). In other embodiments, the cell wall components are phosphatidylinositol mannoside (PIM).

In another aspect, the present invention provides methods of producing a vaccine. The methods comprise administering an opsonin or a lectin to a subject, wherein the opsonin or lectin is capable of binding to a pathogen or fragment thereof, from the subject, thereby forming an opsonin-bound or lectin-bound pathogen construct; isolating the opsonin-bound or lectin-bound pathogen construct from the subject; and combining the isolated opsonin-bound or lectin-bound pathogen construct with a scaffold, thereby producing the vaccine.

In one aspect, the present invention provides kits for vaccinating a subject against a pathogen infection. The kits comprise a vaccine composition of the present invention; and instructions for administering the vaccine to the subject. In some embodiments, the vaccine composition is prepackaged in a sterile container.

In another aspect, the present invention provides kits. The kits comprise a scaffold composition of the present invention; an opsonin-bound or lectin-bound pathogen construct of the present invention, and instructions for administering the scaffold composition and the opsonin-bound or lectin-bound pathogen construct to the subject.

In some embodiments, the scaffold composition and the opsonin-bound or lectin-bound pathogen construct are prepackaged in a sterile container. In other embodiments, the scaffold composition and the opsonin-bound or lectin-bound pathogen construct are prepackaged in different sterile containers. In certain embodiments, the scaffold composition and the opsonin-bound or lectin-bound pathogen construct are prepackaged in the same sterile container.

The present invention is illustrated by the following drawings and detailed description, which do not limit the scope of the invention described in the claims.

BRIEF DESCRIPTION THE DRAWINGS

FIG. 1 depicts the overall pathogen vaccine concept of the present invention.

FIG. 2 depicts FcMBL ELISA standard curve generated using the fungal MBL target, mannan. Specifically, 1 µM FcMBL coated supraparamagnetic particles were used to capture mannan in either buffer or whole donor blood. Serial dilutions of mannan was added to the indicated solutions, mixed with the FcMBL beads, assayed by ELISA and used to generate a curve for quantification of pathogen associated molecular patterns (PAMPs) from test samples.

Figure 5A:
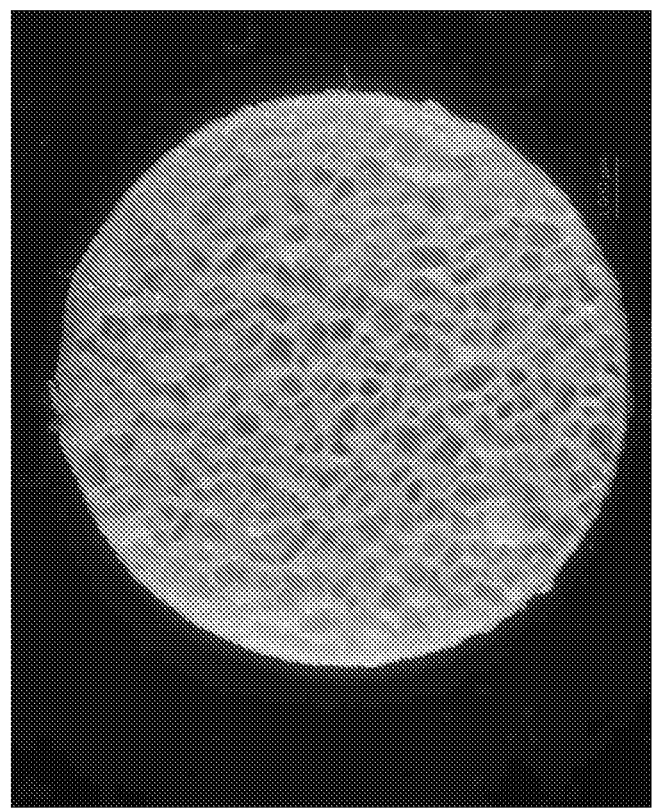
Figure 5C:
Figure 5B:
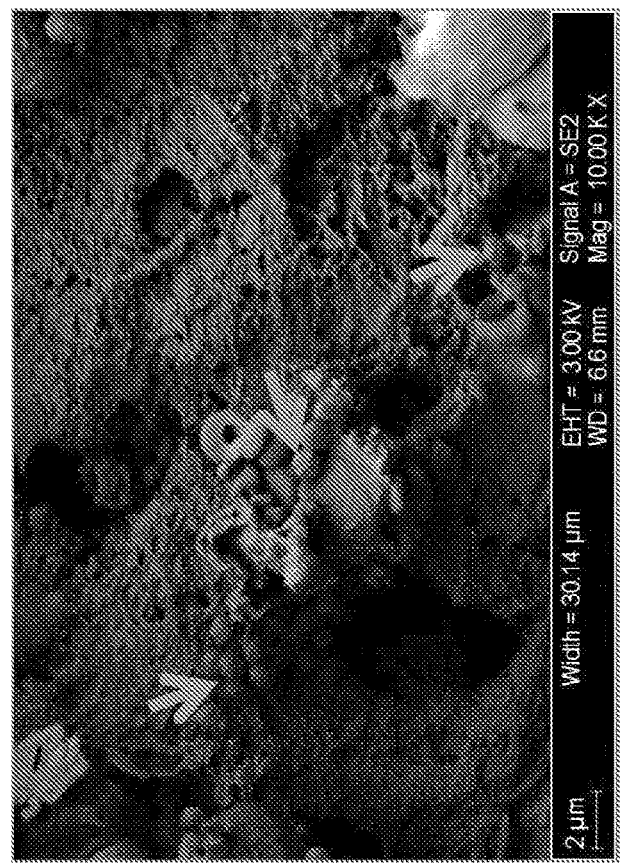

FIGS. 5A-5C depict images of a pathogen vaccine of the present invention. FIG. 5A depicts that the vaccine includes a PLG scaffold containing FcMBL beads coated with captured antibiotics treated RS218 pathogenic *E. coli*. FIG. 5B is an SEM image of FcMBL beads with captured *E. coli* PAMPs incorporated into PLG scaffolds. The FcMBL Beads (1 micron) are clearly visible dispersed throughout the holes and cavities in the PLG scaffolds. FIG. 5C is an SEM image of control scaffolds without the FcMBL beads.

Figure 6:
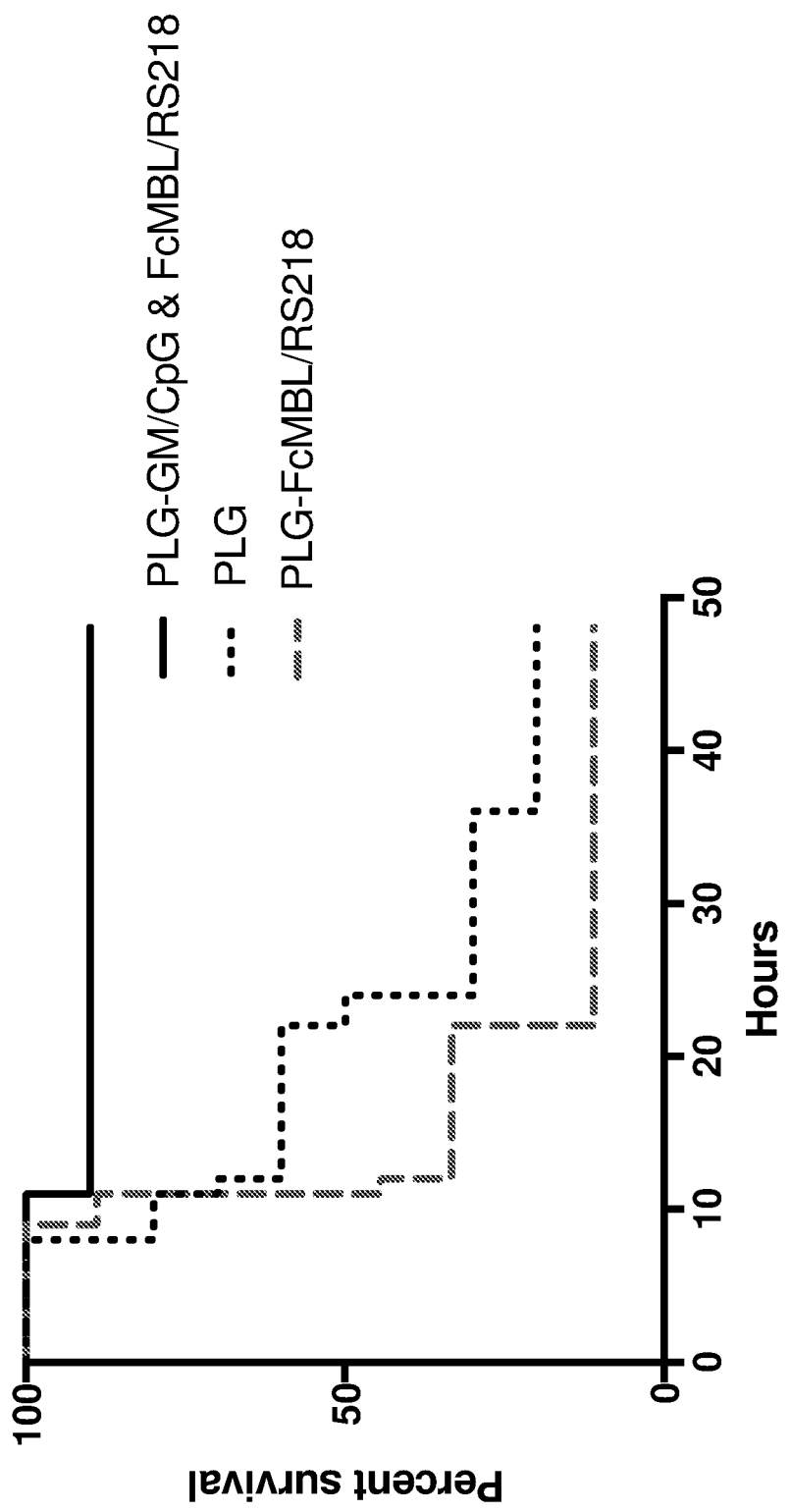

FIG. 6 depicts the survival curves of vaccinated mice upon infection with a lethal dose of RS218 *E. coli* bacteria. Mice were implanted subcutaneously with a PLG vaccine scaffold containing FcMBL captured RS218 fragments for 3 weeks. Mice were infected intraperitoneally on day 21 with a lethal dose of RS218. Survival of mice was monitored for 48 hours and mice were humanely sacrificed earlier if clinical conditions required. Vaccinated animals exhibited a significantly prolonged survival time. A prophylactic vaccine of PLG-GMCFS/CpG with FcMBL beads coated with RS218 protected 9 out of 10 mice till the end of the study at 48 hours while PLG scaffold alone or PLG with FcMBL beads/RS218 lysate without recruiting and adjuvant factors did not protect. Treatment groups (n=10).

Figure 7B:
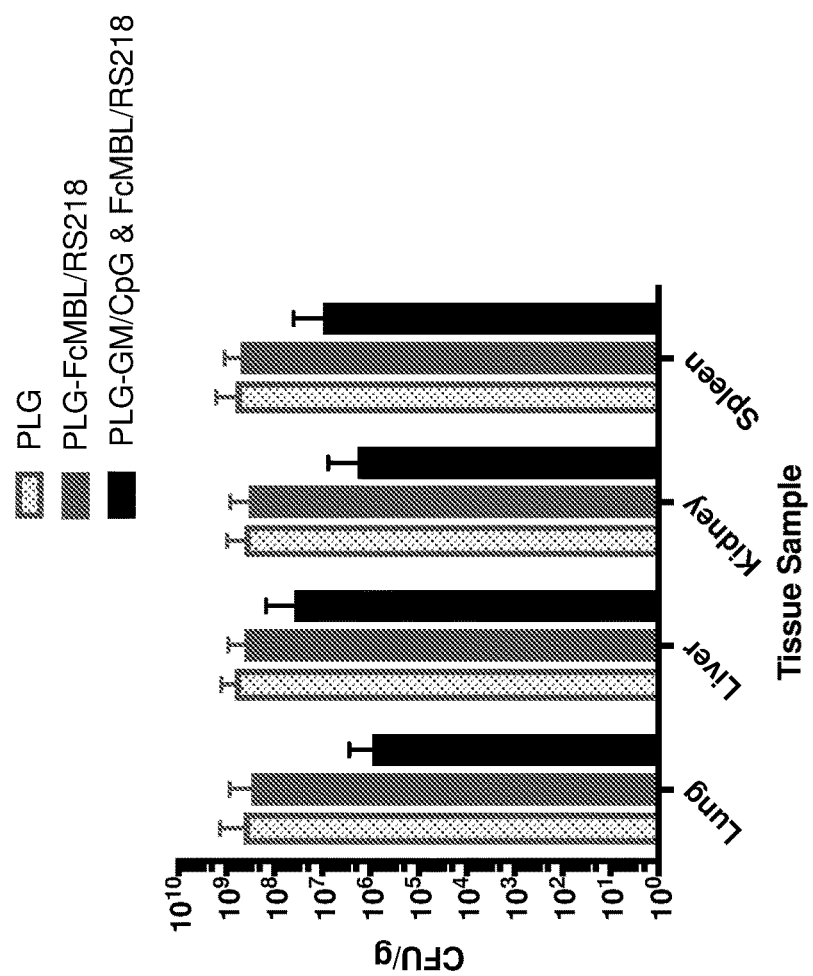
Figure 7A:
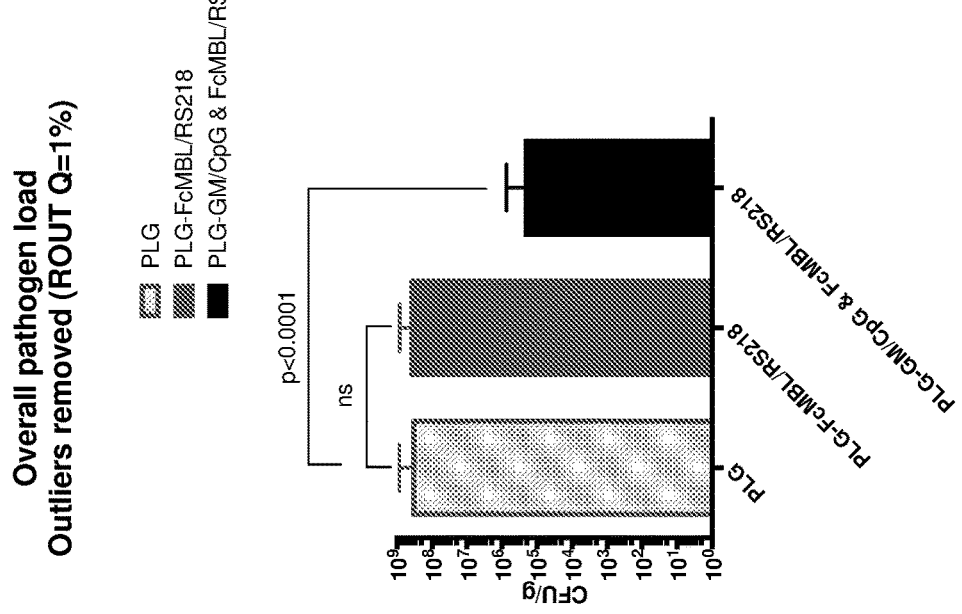

FIGS. 7A-7B depict the total organ pathogen counts and the individual organ pathogen counts of vaccinated mice upon treatment with a lethal dose of RS218 bacteria, respectively. Mice were implanted subcutaneously with a PLG vaccine scaffold containing FcMBL captured RS218 fragments for 3 weeks. Mice were infected intraperitoneally on day 21 with a lethal dose of RS218. Organ cultures were collected in a sterile fashion, processed by mechanical disruption and plated to determine the titer of pathogen in the organs. A significant reduction in pathogen titers was observed in vaccinated animals. Treatment groups (n=10). Pathogen loads were reduced by 2.5-3.5 logs (p=0.0021-0.0057).

Figure 8:
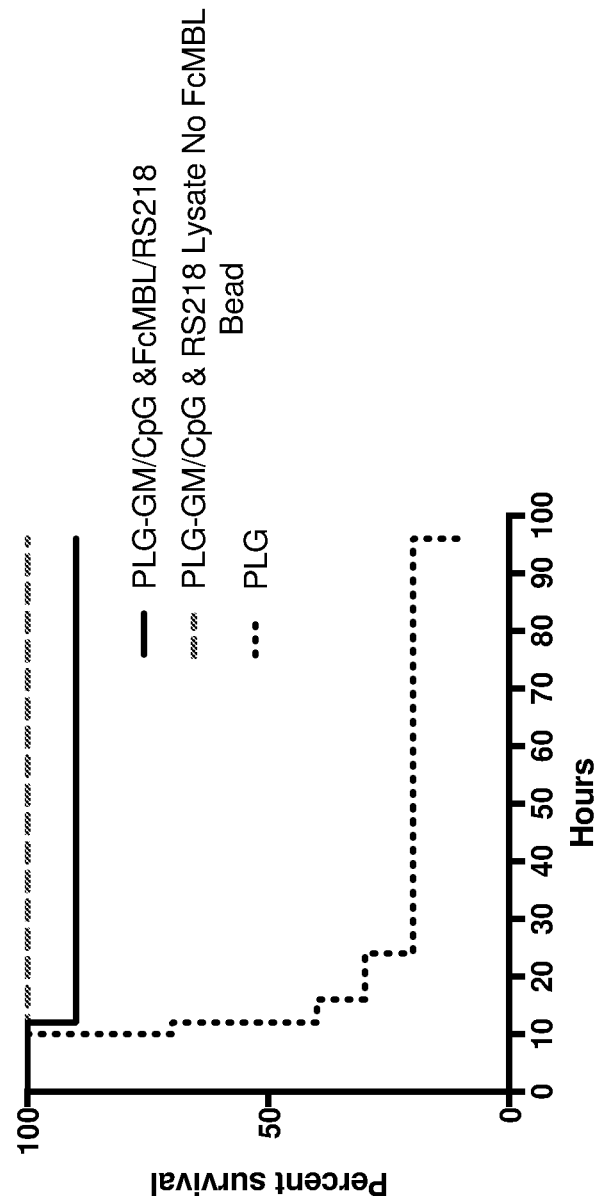

FIG. 8 depicts the survival curves of mice vaccinated with PLG vaccine scaffolds containing either FcMBL captured RS218 fragments or whole RS218 lysate. Mice were implanted subcutaneously with a PLG vaccine scaffold (with GM-CSF and CpG) or scaffolds containing either FcMBL captured RS218 fragments or whole RS218 lysate for 21 days, then challenged intraperitoneally with a sub-lethal dose of RS218 bacteria. Survival of vaccinated mice was monitored. Vaccinated animals exhibited a significantly prolonged survival time.

Figure 9:
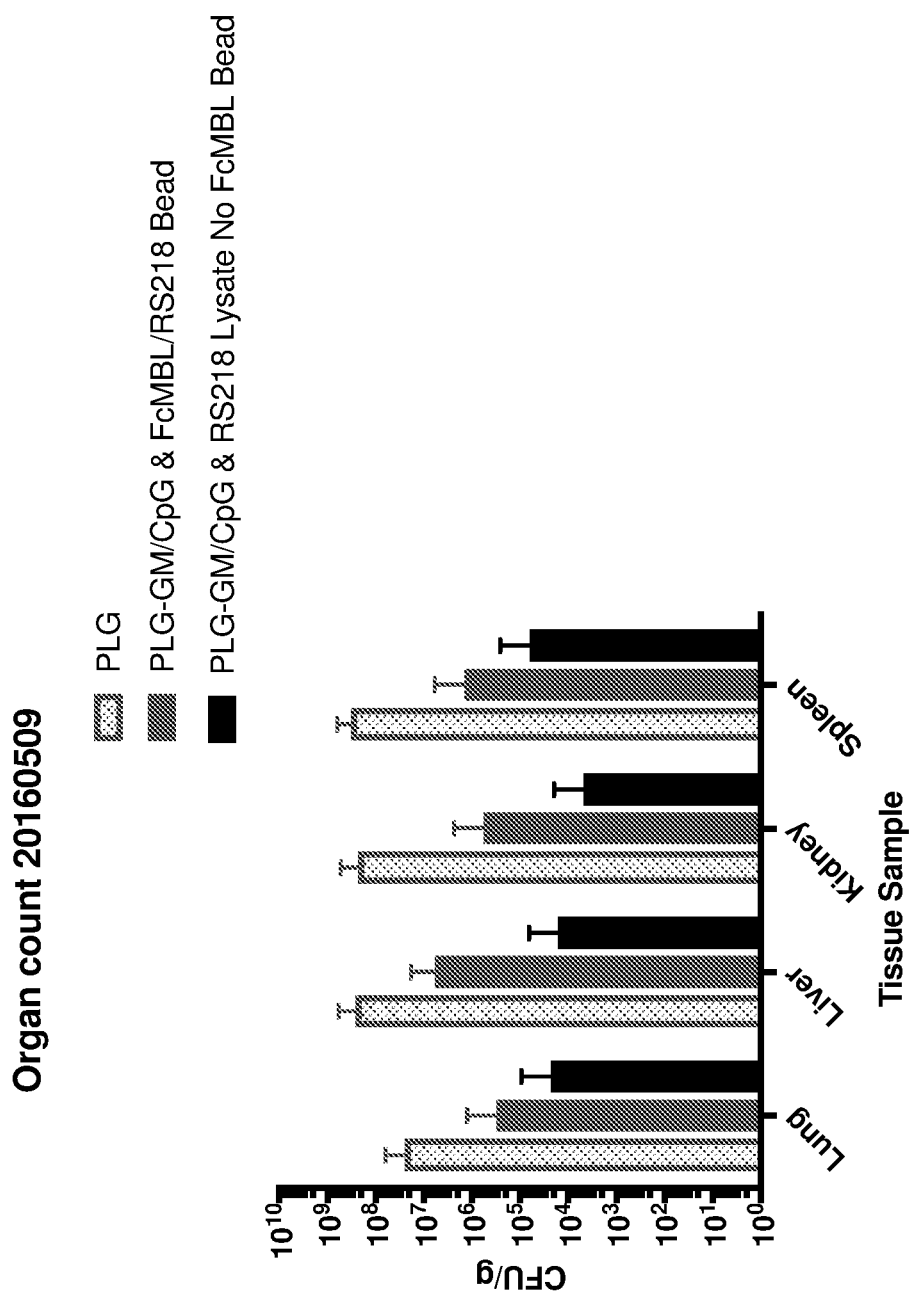

FIG. 9 depicts the individual organ pathogen counts of mice vaccinated with PLG vaccine scaffolds containing either FcMBL captured RS218 fragments or whole RS218 lysate. Mice were implanted subcutaneously with a PLG vaccine scaffold (with GM-CSF and CpG) or scaffolds containing either FcMBL captured RS218 fragments or whole RS218 lysate for 21 days, then challenged intraperitoneally with a sub-lethal dose of RS218 bacteria. Organ cultures were collected in a sterile fashion, processed by mechanical disruption and plated to determine the titer of pathogen in each individual organ. Organ cultures showed a significant reduction in pathogen titers in the vaccinated animals.

FIGS. 10A-10C depict in vitro quantification of the amount of CpG, GM-CSF and *E. coli* RS218 endotoxin leakage out of the PLG vaccine scaffolds, during leach of the sucrose, containing either FcMBL captured RS218 fragments or whole RS218 lysate. No significant difference was observed for the CpG content (FIG. 10A) and the GM-CSF content (FIG. 10B) when comparing between sham scaffolds, those with no beads (only lysate), or beads with lysate. However, a significant endotoxin leakage was observed in PLG vaccine scaffolds containing the whole RS218 lysate, whereas the PLG vaccine scaffolds containing the FcMBL captured RS218 fragments demonstrated minimal leakage of endotoxin (FIG. 10C).

Figure 11C:
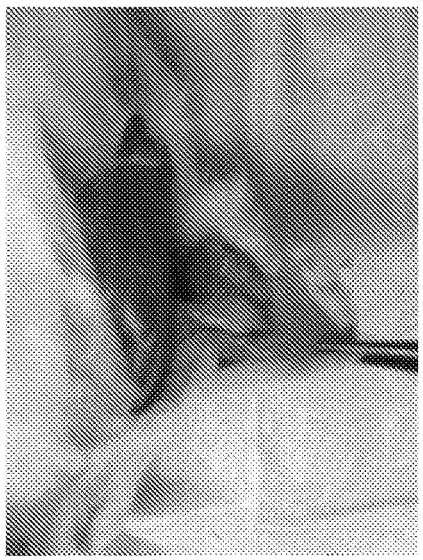
Figure 11B:
Figure 11A:

FIGS. 11A-11C are images taken at the sites of vaccine implantation depicting the overall condition of the vaccinate mice. Mice were implanted subcutaneously with a PLG vaccine scaffold (with GM-CSF and CpG) or scaffolds containing either FcMBL captured RS218 fragments or whole RS218 lysate for 21 days, then challenged intraperitoneally with a sub-lethal dose of RS218 bacteria. Mice receiving the sham scaffolds had no signs of immune reaction (FIG. 11A), and the vaccine scaffold was largely intact in mice receiving the PLG vaccine scaffolds containing FcMBL captured RS218 fragments (FIG. 11B). However, mice receiving the PLG vaccine scaffolds containing whole RS218 lysate experienced undesired side effects with formation of large abscesses (FIG. 11C).

Figure 12A:
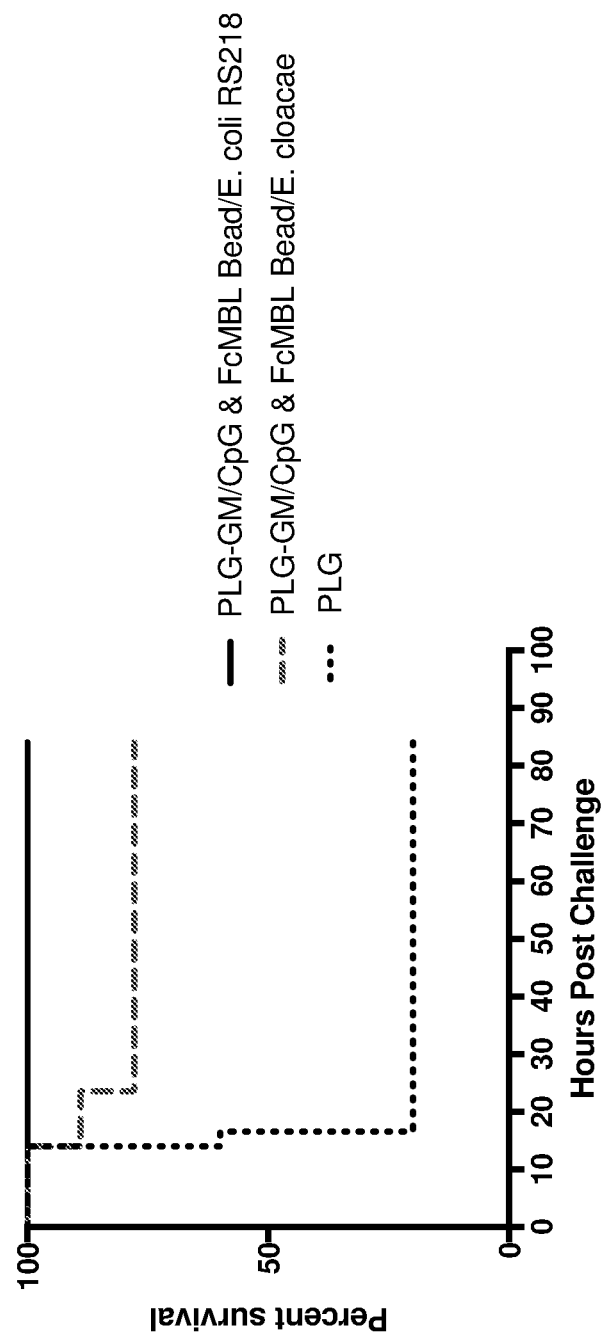
Figure 12B:
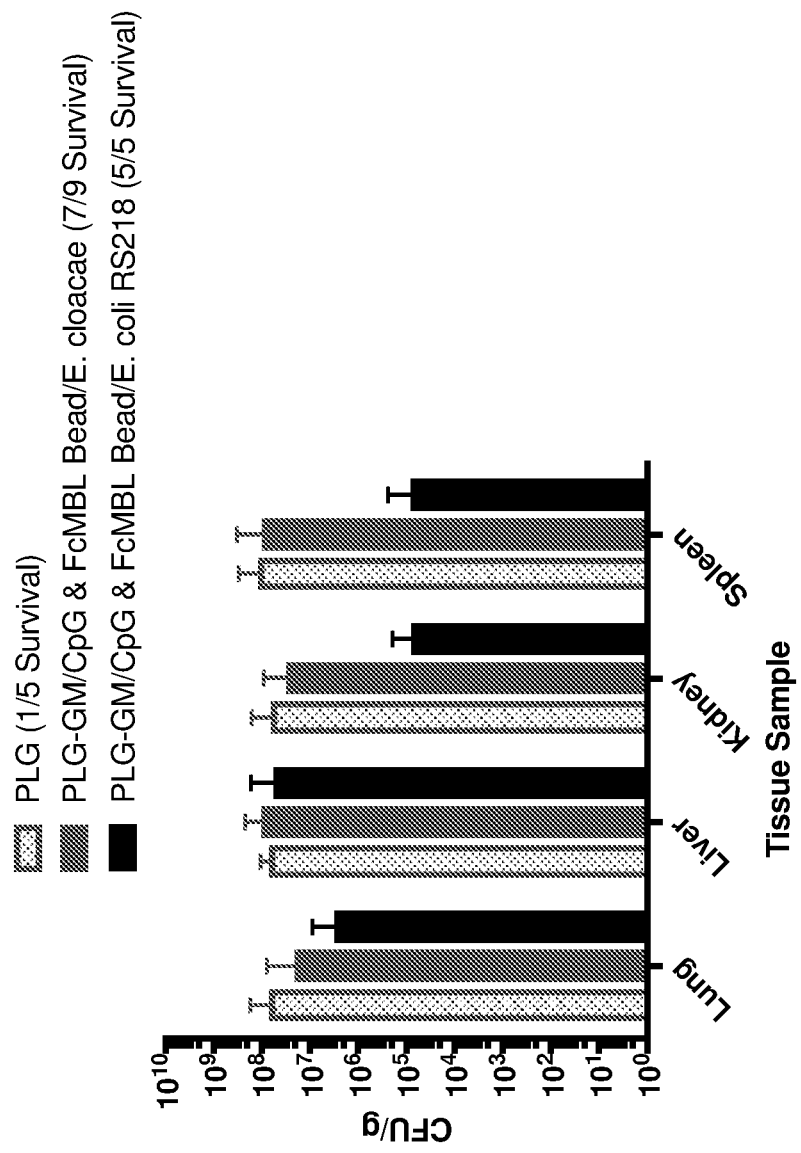

FIGS. 12A-12B depict cross-reactivity of the infection vaccine technology. FIG. 12A depicts the survival curves of mice vaccinated with PLG vaccine scaffolds containing either FcMBL captured *E. cloacae* lysate or FcMBL captured *E. coli* RS218 lysate. Mice were implanted subcutaneously with a PLG vaccine scaffold (with GM-CSF and CpG) or scaffolds containing either FcMBL captured *E. cloacae* lysate or FcMBL captured RS218 lysate for 21 days, then challenged intraperitoneally with a lethal dose of RS218 bacteria. Survival of vaccinated mice was monitored. A prophylactic vaccine of PLG-GMCSF/CpG with FcMBL beads coated with RS218 lysate protected 100% mice till the end of the study at 96 hours from the RS218 challenge, and vaccine of PLG-GMCSF/CpG with FcMBL beads coated with *E. cloacae* lysate protected 78% mice till the end of the study at 96 hours from the RS218 challenge (LD90 at 20 hrs). PLG scaffolds with only GMCSF recruiting and CpG adjuvant (without FcMBL beads and RS218 lysate) protected only 20% of animals at 96 hours. Both *E. cloacae* and *E. coli* are members of the order Enterobacteriaceae. FIG. 12B depicts the individual organ pathogen counts of mice with PLG vaccine scaffolds containing either FcMBL captured *E. cloacae* lysate or FcMBL captured RS218 lsate. Organ cultures were collected in a sterile fashion, processed by mechanical disruption and plated to determine the titer of pathogen in each individual organ. Organ cultures showed a reduction in pathogen titers in the vaccinated animals.

Figure 13:
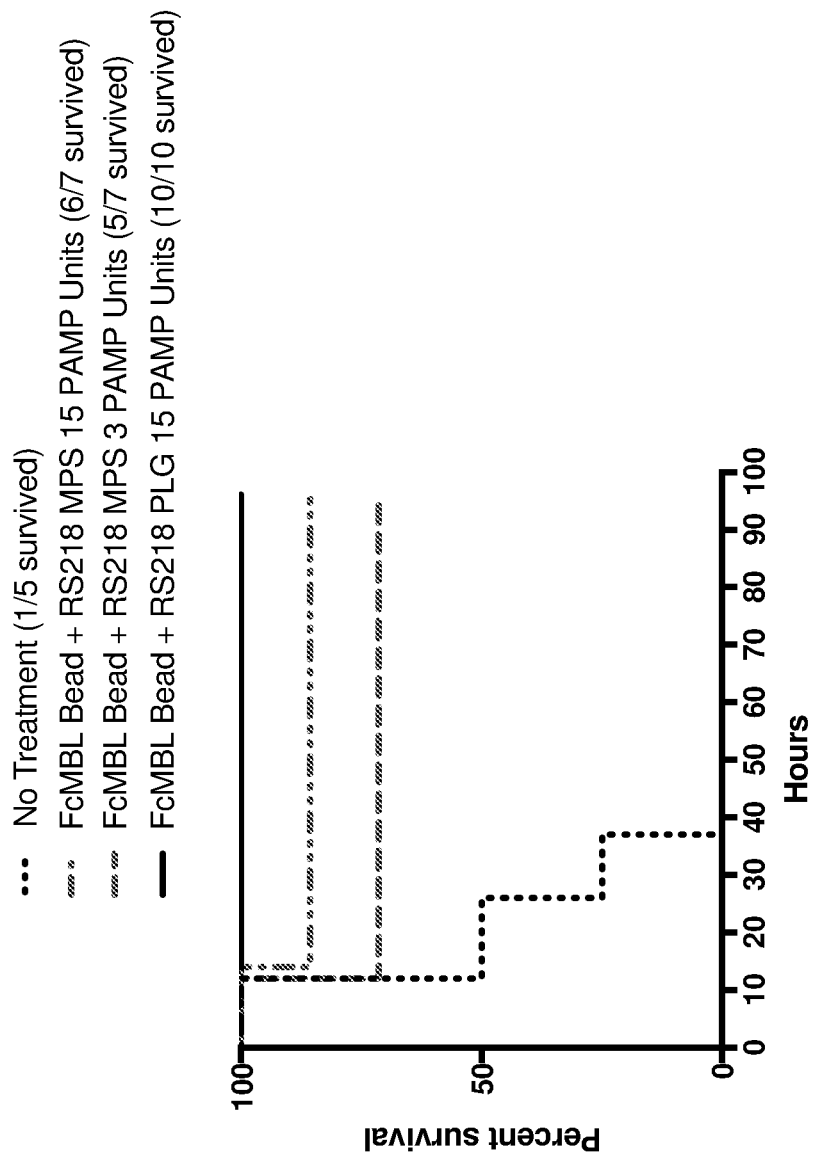

FIG. 13 depicts a dose response study for vaccine compositions with different scaffolds. Specifically, a prophylactic vaccine of MPS scaffold and GMCSF/CpG with FcMBL beads were coated with different doses of *E. coli* RS218 Lysate. Vaccine with 15 PAMP units protected 90% of mice from 21 days challenge while vaccine with 3 PAMP units only protected 70% All mice receiving PLG vaccine scaffolds containing GMCSF/CpG and FcMBL beads coated with 15 PAMPs survived the challenge.

Figure 14:
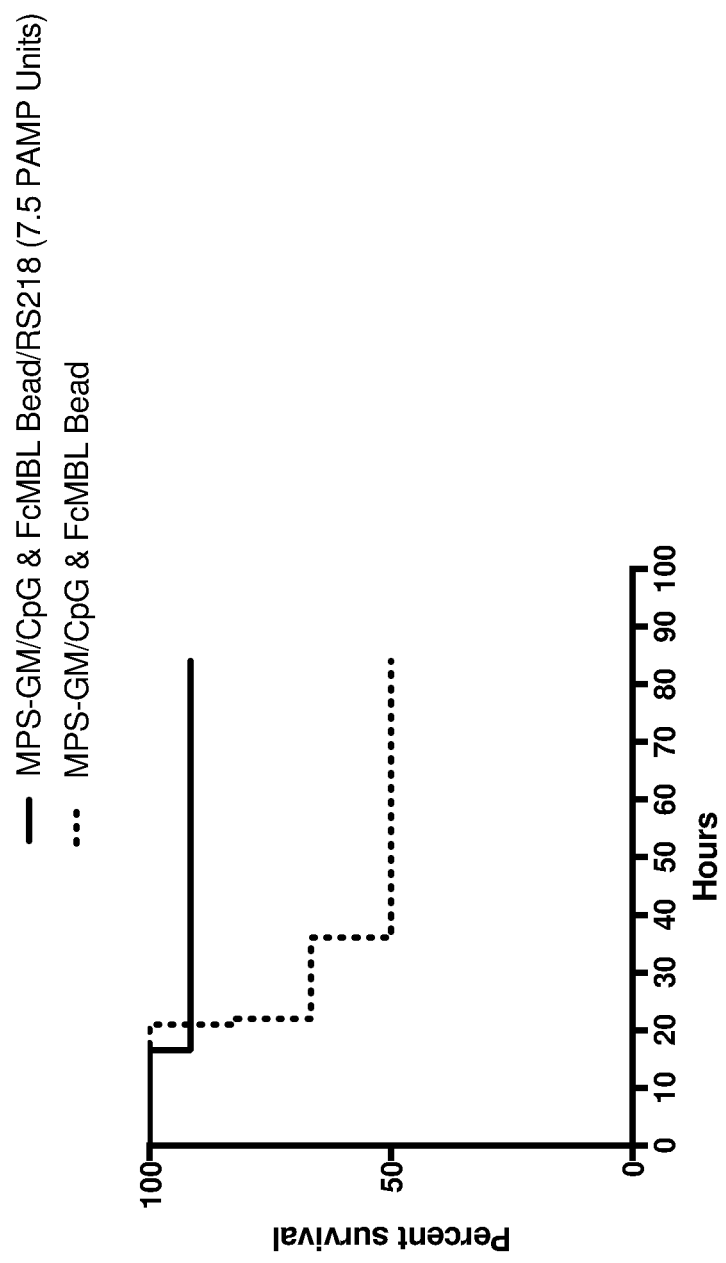

FIG. 14 depicts the survival curves of mice vaccinated with MPS vaccine scaffolds containing FcMBL captured RS218 lysate. A prophylactic vaccine of MPS-GMCSF/CpG with FcMBL beads coated with *E. coli* (RS218) lysate protected 90% mice till the end of the study at 96 hours from the RS218 challenge (n=12). Only 50% of mice vaccinated with sham MPS-GMCSF/CpG survived (n=6) with the RS218 challenge.

Figure 15A:
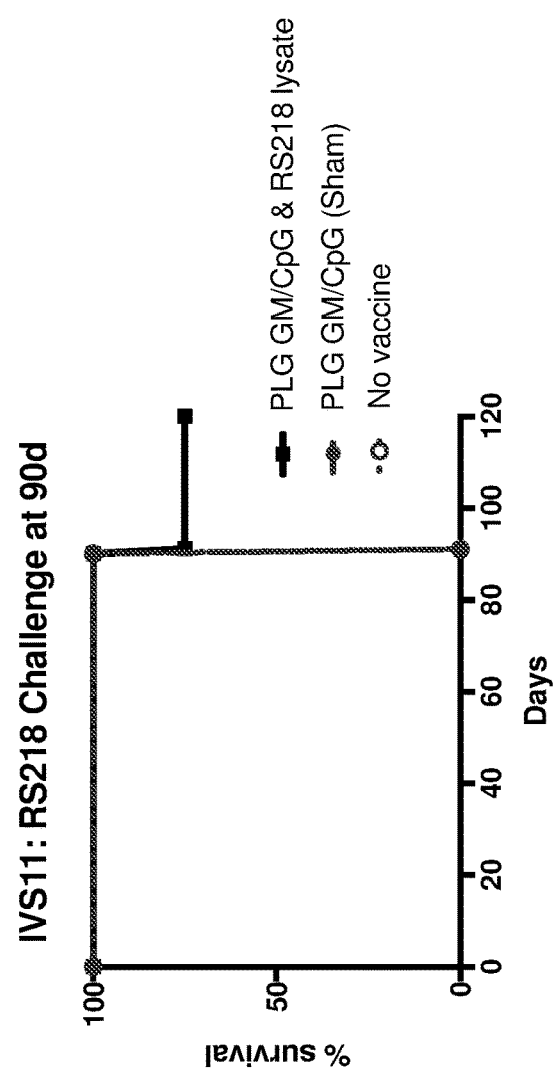
Figure 15B:
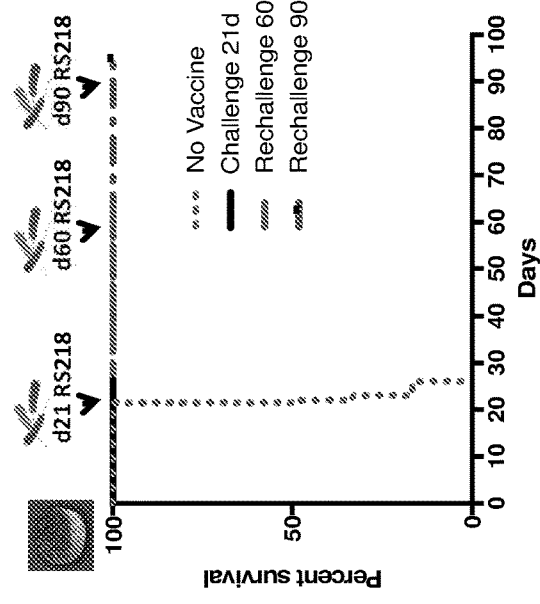

FIGS. 15A-15B depict the long-term effect of a single implanted dose of the infection vaccine technology. FIG. 15A depicts that a prophylactic vaccine of PLG-GMCSF/CpG with FcMBL beads coated with *E. coli* RS218 lysate protected 100% of mice for more than 96 days despite (boosting) RS218 challenges at 21, 60 and 90 days. FIG. 15B depicts that the use of a more challenged dose of RS218 bacteria, and shows that a prophylactic vaccine of PLG-GMCSF/CpG with FcMBL beads coated with *E. coli* RS218 lysate protected 75% of mice for more than 96 days.

FIG. 16 are histology images depicting dense cellular infiltration with both PLG and MPS scaffolds.

Figure 17:
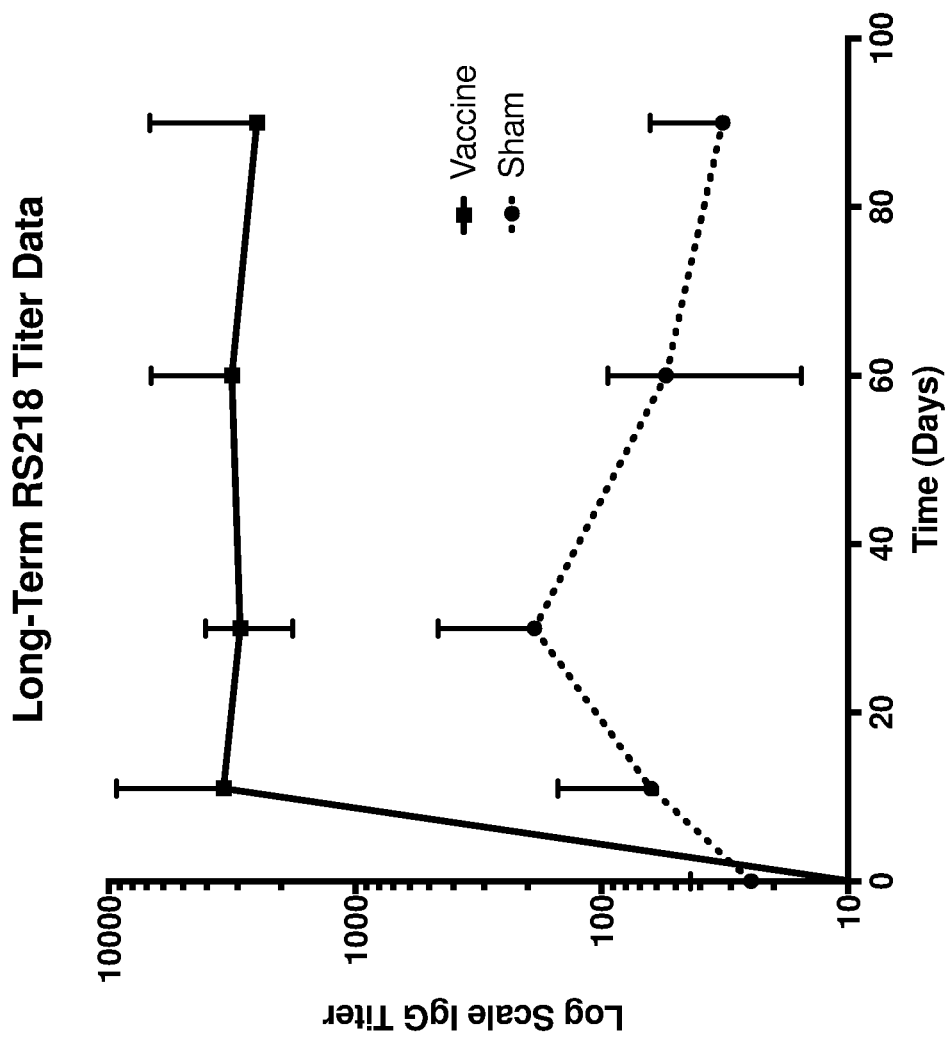

FIG. 17 depict the long-term antibody-mediated protection effect of the infection vaccine technology, Specifically, FIG. 17 depicts a long-term IgG titer against the RS218 bacteria over a period of 90 days.

Figure 18:
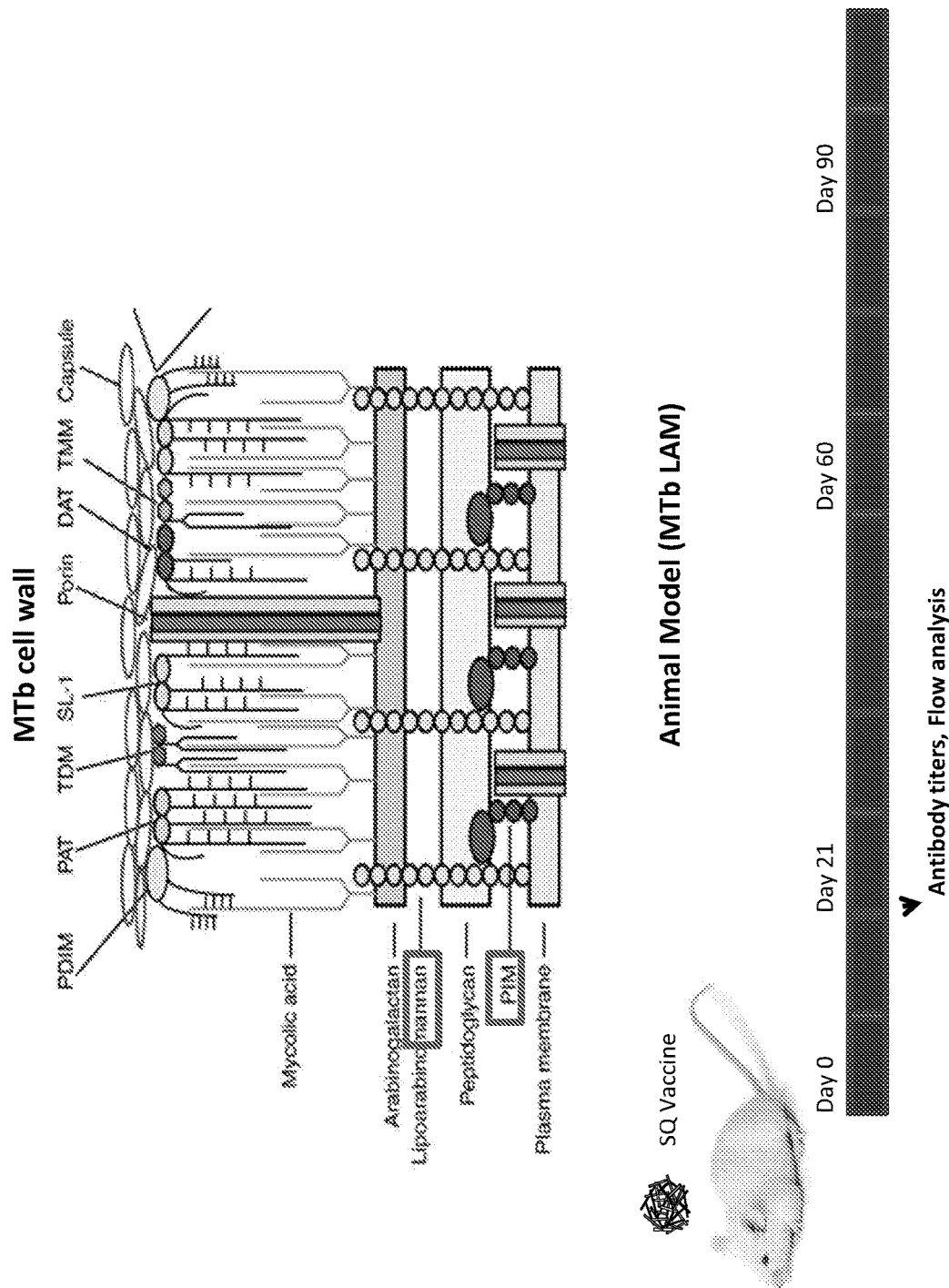

FIG. 18 depicts binding of FcMBL to *Mycobacterium tuberculosis* (MTb) in tuberculosis and the potential use of the infection vaccine technology for treating tuberculosis. Specifically, FcMBL can bind to mannosylated components of *Mycobacterium tuberculosis* (MTb) cell wall e.g. mannose-capped Lipoarabinomannan (ManLAM), and Phosphatidylinositol Mannoside (PIM).

Figure 19:
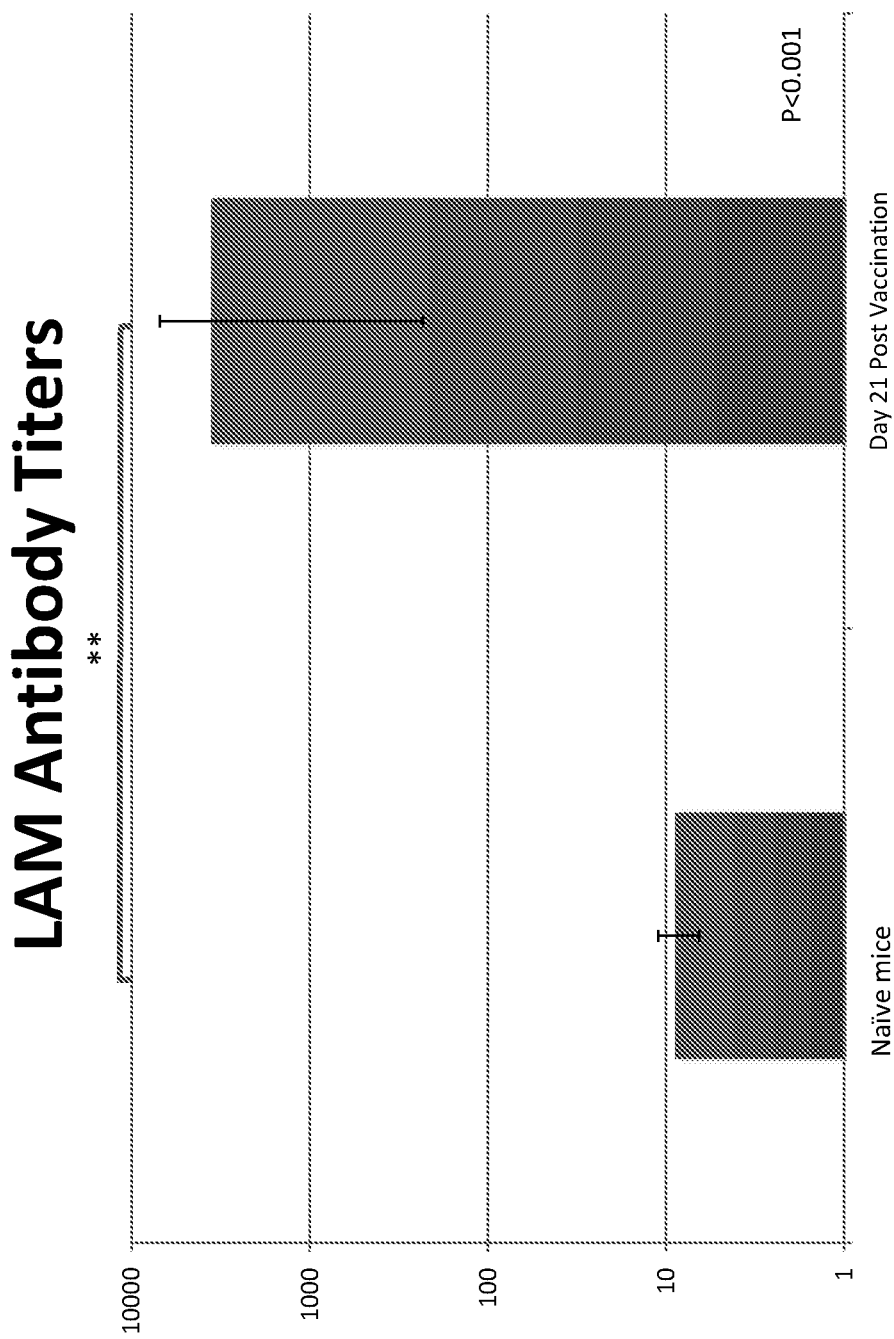

FIG. 19 depicts the antibody-mediated effect of the infection vaccine technology against mannose-capped Lipoarabinomannan (ManLAM). When mice were vaccinated with a single dose of MPS-GMCSF/CpG containing FcMBL beads coated with LAM Lysate, the titers of LAM-specific IgG increased by 2-3 logs over pre-vaccinated naïve animals. (p=<0.001).

Figure 20:
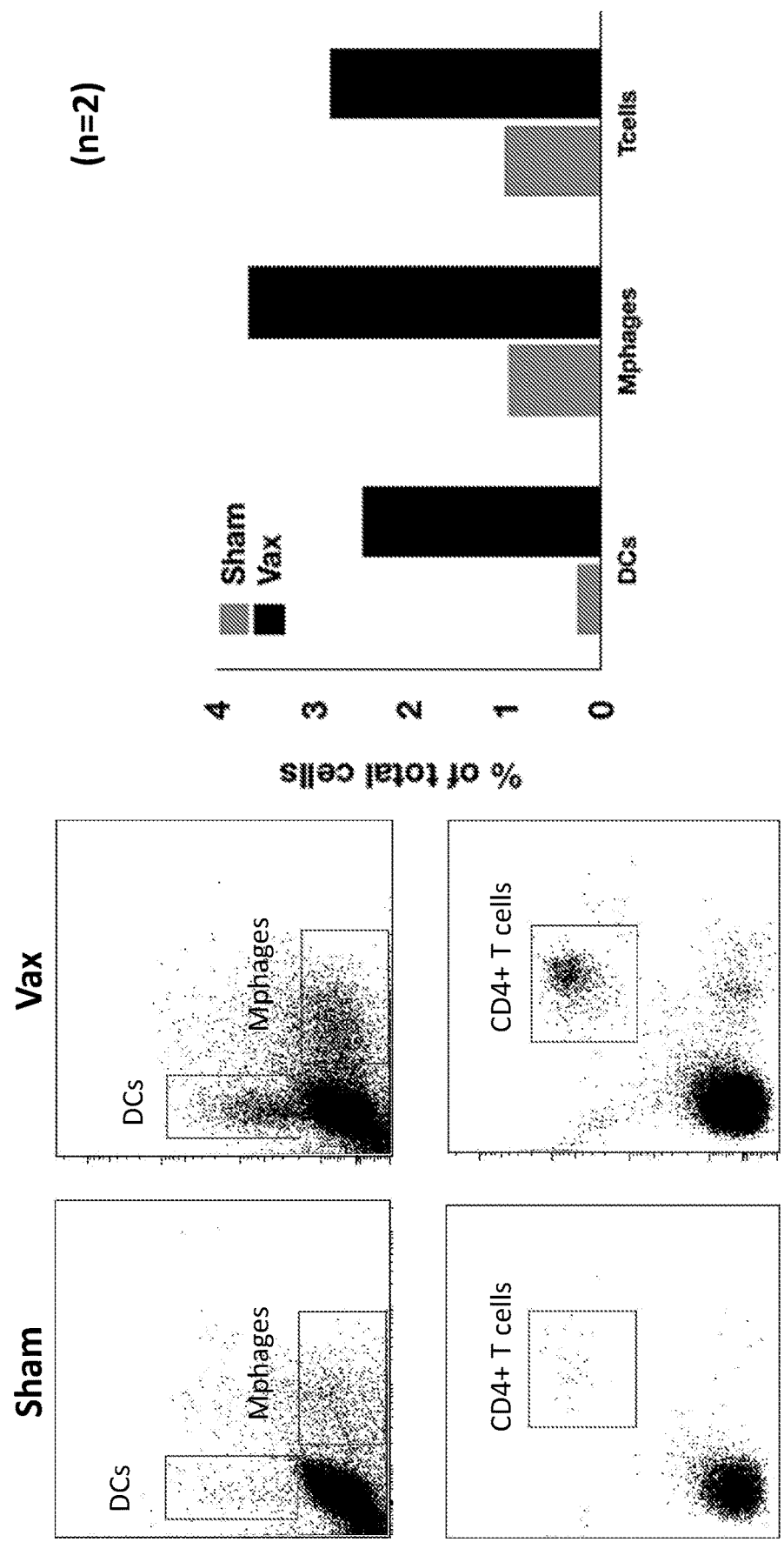

FIG. 20 depicts the cell-mediated anti-LAM response against mannose-capped Lipoarabinomannan (ManLAM). Specifically, FIG. 20 depicts the FACS analysis of infiltrating cells in sham MPS scaffolds or in MPS in PLG scaffolds containing FcMBL beads and MTb PAMPs. Control scaffolds (sham) showed few infiltrating cells, while dendritic cells (DCs), macrophages (Mphages) and CD4+ T cells were significantly increased in test scaffolds (Vax) (graph on right).

Figure 21A:
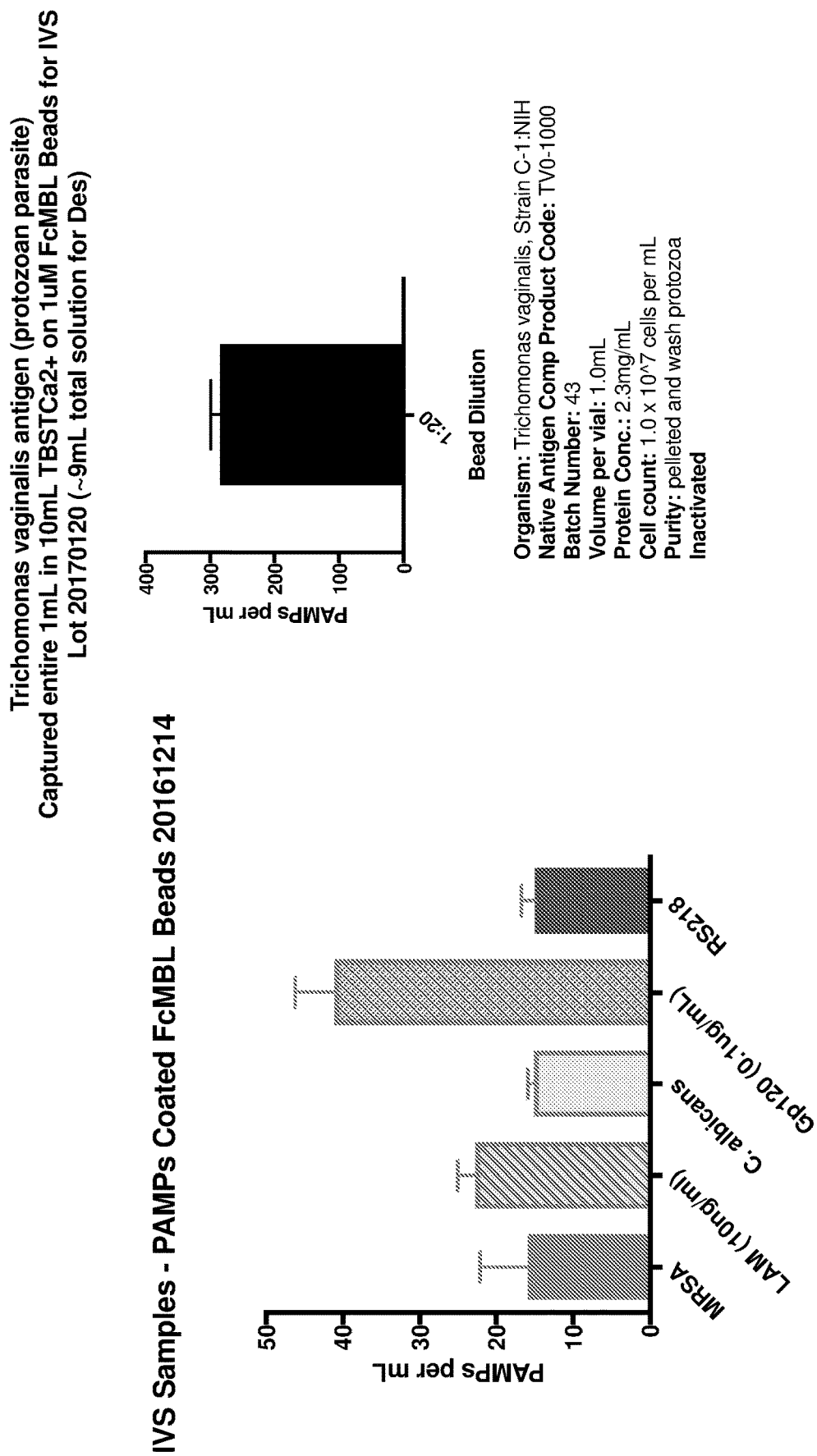
Figure 21B:
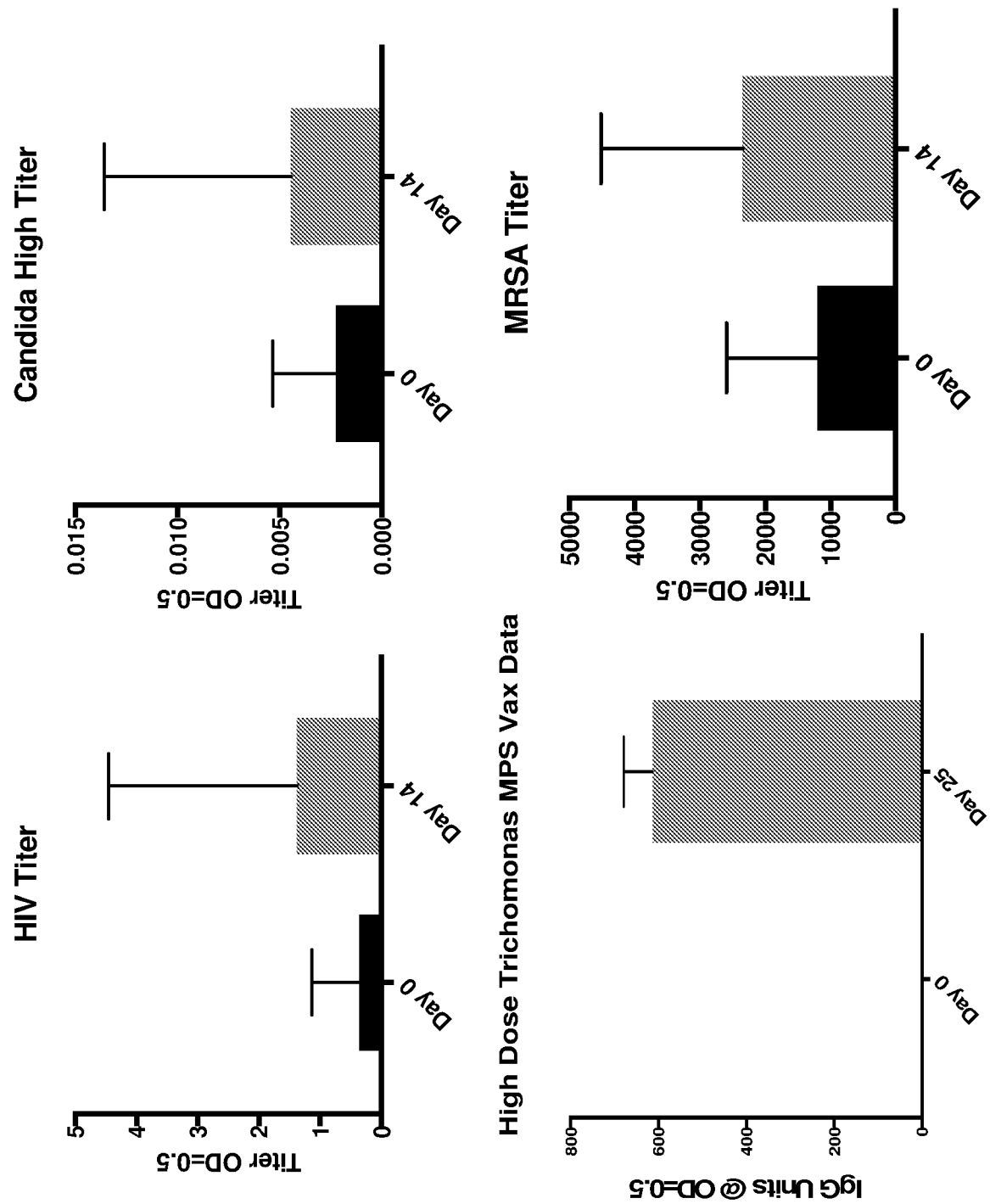

FIGS. 21A-21B depict the ability of FcMBL to capture multiple pathogen genera. FIG. 21A depicts that different amount of PAMPs from Gram negative bacteria (*E. coli* RS218), Gram positive (MRSA, LAM), fungi (*Candida albicans*), viruses (HIV gp120) and parasites (*Trichomonas vaginalis*) were coated with FcMBL beads. FIG. 21B depicts an increased antibody titer in mice on vaccination. Mice were vaccinated with a single dose of MPS-GMCSF/CpG containing FcMBL beads coated with samples from gram negative bacteria (*E. coli* RS218), Gram positive (MRSA, LAM), fungi (*Candida albicans*), viruses (HIV gp120) and parasites (*Trichomonas vaginalis*). The titers of LAM-specific IgG was increased over pre-vaccinated naïve animals in all cases.

Figure 22:
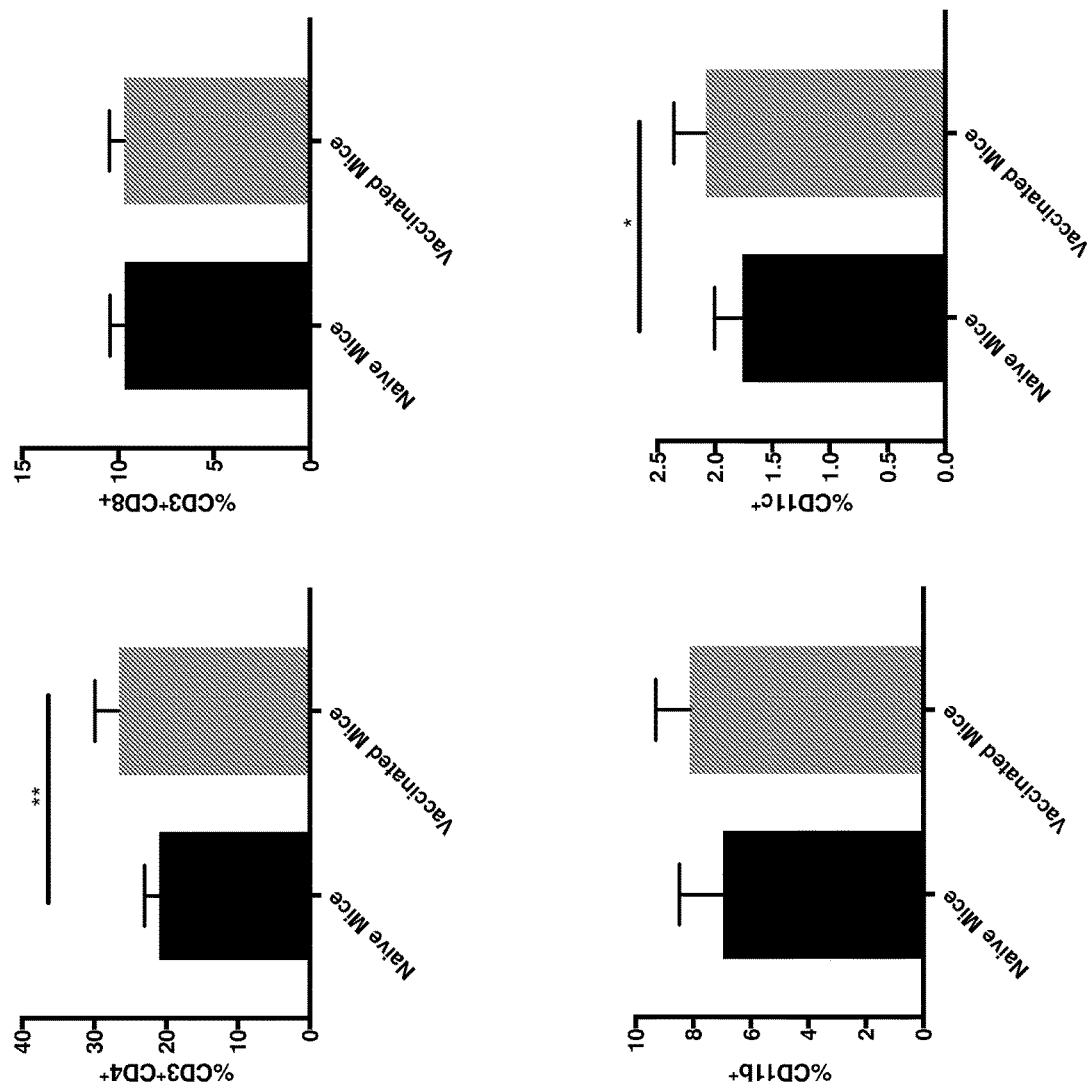

FIG. 22 depicts the cell-mediated anti-*Trichomonas* response against *Trichomonas* lysate incorporated into a vaccine. Specifically, FIG. 22 depicts the FACS analysis of infiltrating cells in spleens of vaccinated animals. Control spleens (Naive) showed fewer infiltrating CD4+T cells and CD11c cells than spleens in the vaccinated animal groups.

Figure 23:
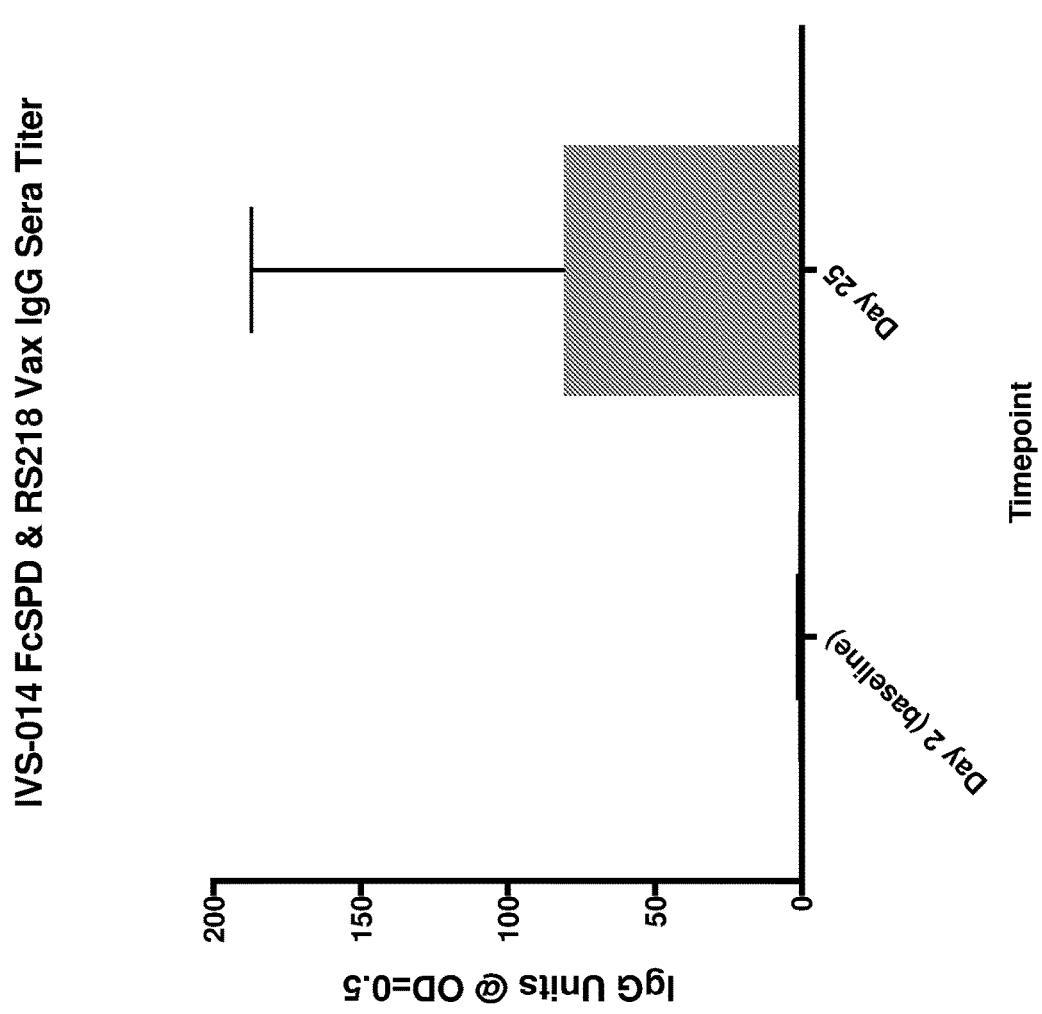

FIG. 23 depicts the antibody titers generated in mice vaccinated with a vaccine composition comprising an alternative lectin, surfactant protein D (SPD). Surfactant protein D (SPD) is another collectin (C-type lectin with collagen region) related to MBL. An FcSPD was generated, which has 77% protein sequence identity to FcMBL. FcSPD was shown to be able to bind the RS218 *E. coli*. An antibody-mediated immune reaction was elicited when FcSPD captured RS218 was incorporated into the MPS scaffold and used to vaccinate mice. An increased antibody titer was observed in vaccinated mice when compared to the non-vaccinated control.

DETAILED DESCRIPTION OF THE INVENTION

Figure 1:
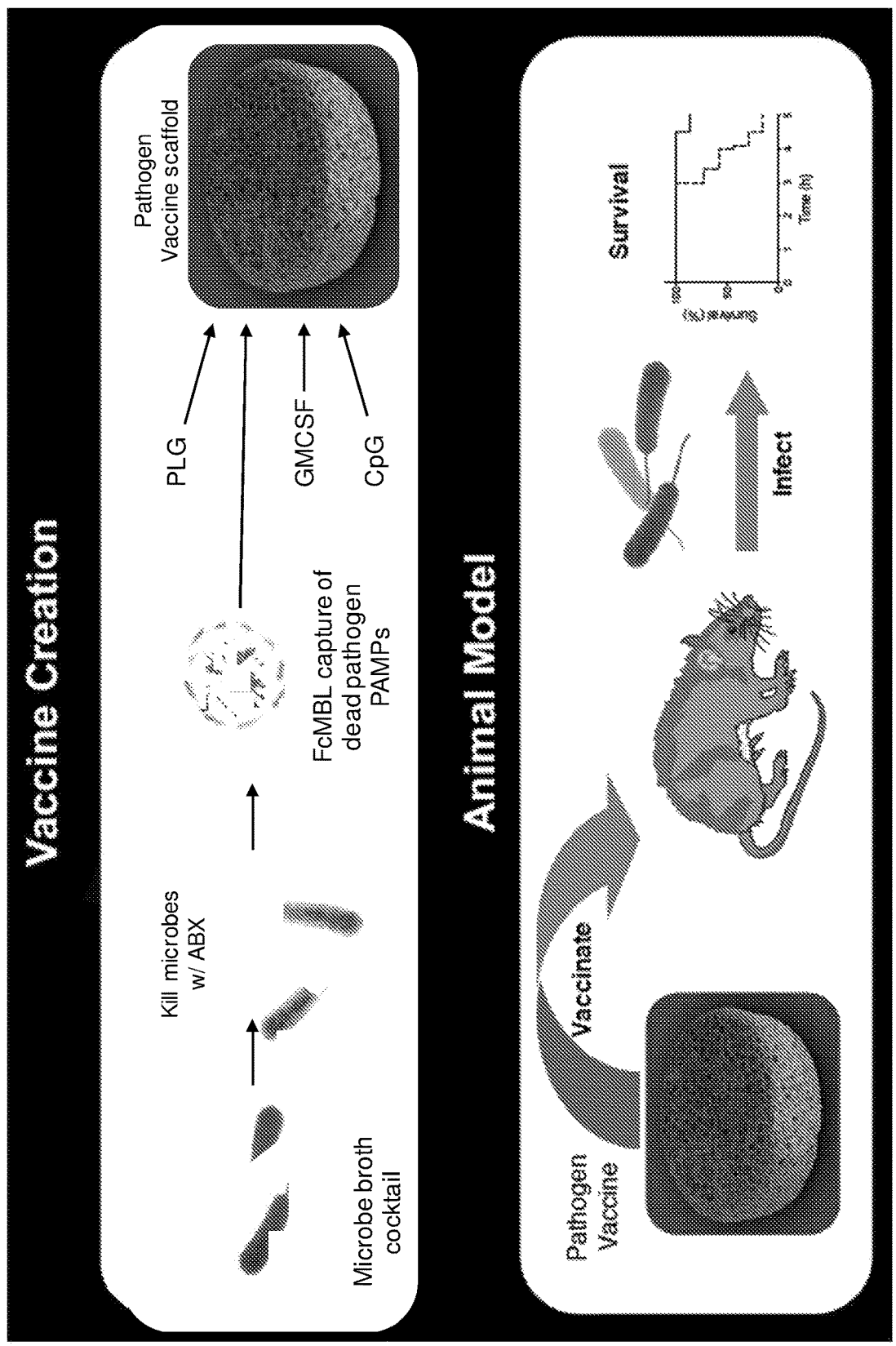

The present invention is based, at least in part, on the discovery that pathogens or pathogen associated molecular patterns (PAMPs) isolated using an opsonin or lectin, e.g., an engineered lectin or fragment thereof, can be used to generate functional vaccines for the treatment of infectious diseases. In particular, the present inventors have surprisingly discovered that pathogens or pathogen associated molecular patterns (PAMPs) isolated using an engineered lectin, when combined with a bioactive agent, e.g., an adjuvant, and/or a scaffold, allow for the rapid creation of high potency pathogen vaccines (FIG. 1). When used to vaccinate animals, a single dose of these vaccines resulted in a significantly reduced pathogen titer in the vaccinated animals and a significantly prolonged survival time after infecting the animals with a lethal dose of bacteria. Indeed, as shown in Example 1, a single dose of the vaccine composition of the invention can protect the vaccinated mice from bacteria challenge over a period of 90 days. In addition, the opsonin or lectin, e.g., an engineered lectin or fragment thereof, not only functions to isolate a pathogen for use in the vaccine compositions and present the pathogen to immune cells to initiate immune response, but also serves as an anchor structure to immobilize the pathogen, thus preventing leakage of pathogen from the vaccine composition, and preventing any undesired side effects currently experienced with the pathogen leakage.

The vaccine compositions of the present invention possess additional improvements over existing vaccines. For example, the vaccine compositions of the present invention allow the rapid and direct isolation of pathogens circulating in a blood sample from a patient with infectious disease including both known and unknown pathogens, pathogens present within other biological fluids, or pathogens present in in vitro cultures. The claimed vaccine compositions can also be used against pathogens that are difficult to isolate and purify. Once the pathogens are isolated from a subject, the vaccine compositions can be readily prepared in a fast and convenient manner anywhere in the world, and can be available for patients in a timely manner, for example, within one day. In addition, vaccination using the claimed vaccine compositions can occur in a more controlled, localized and safer manner, without compromising the efficacy of the vaccine compositions. The improved stability of the claimed vaccines allows them to be portable and be used for long term storage at room temperature without the need of refrigeration. Furthermore, the vaccine compositions can be multivalent vaccines when more than one type of pathogens are included in the compositions, and can also be used to vaccinate against different species or strains of a given pathogen. In addition, the vaccine compositions, if implanted, can be easily removed from the subject after vaccination. For example, in the case where too much immune response or undesired side effects are initiated after vaccination, the implanted vaccine compositions can be readily removed from the subject. In contrast, current existing vaccines cannot be removed once they are injected in the subjects. These improvements circumvent the major limitations of current pathogen vaccines, and would be of great interest to the public, especially during the time of an epidemic, for example, for populations in developing countries, or of great value for military uses, where vaccines that are readily available are highly desired. Indeed, the ability to rapidly create functional and highly stable vaccines that are not only easy for storage and handling, but may be administered in a safer and more controlled manner and confer a long-term protective effect, renders the vaccine compositions of the present invention significantly advantageous over existing vaccines.

Accordingly, the present invention provides vaccine compositions and methods of producing such compositions. Other embodiments of the invention include methods of treating a pathogen infection, methods of vaccinating a subject against a pathogen infection, and methods for treating an antibiotic-resistance bacterial infection in a subject in need thereof. In further embodiments, the invention includes methods of decreasing the level of a pathogen in a subject having a pathogen infection, methods of increasing the surviving rate of a subject having a pathogen infection, methods of reducing pain associated with a pathogen infection and methods of reducing distress associated with a pathogen infection in a subject in need thereof. Novel scaffold compositions and pathogen compositions and uses thereof are also provided herein.

I. Definitions

In order that the present invention may be more readily understood, certain terms are first defined. In addition, it should be noted that whenever a value or range of values of a parameter are recited, it is intended that values and ranges intermediate to the recited values are also part of this invention.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

The articles "a" and "an" are used herein to refer to one or to more than one (i.e., to at least one) of the grammatical object of the article. By way of example, "an element" means one element or more than one element.

The term "comprising" or "comprises" is used herein in reference to compositions, methods, and respective component(s) thereof, that are essential to the invention, yet open to the inclusion of unspecified elements, whether essential or not.

The term "consisting of" refers to compositions, methods, and respective components thereof as described herein, which are exclusive of any element not recited in that description of the embodiment.

The term "vaccine," as used herein, includes any composition containing an immunogenic determinant which stimulates the immune system such that it can better respond to subsequent infections. A vaccine usually contains an immunogenic determinant, e.g., an antigen, and an adjuvant, the adjuvant serving to non-specifically enhance the immune response to that immunogenic determinant. Currently produced vaccines predominantly activate the humoral immune system, i.e., the antibody dependent immune response. Other vaccines focus on activating the cell-mediated immune system including cytotoxic T lymphocytes which are capable of killing targeted pathogens.

The term "opsonin," as used herein, refers to any protein or fragment thereof that recognizes a surface molecule of a pathogen cell, e.g., a pathogen associated molecular pattern (PAMP), thereby marking and targeting the bound pathogen cell for destruction, e.g., by complement attack and phagocytosis. In some embodiments, the opsonin is a natural opsonin, such as an antibody that is generated by B cells in response to antigen exposure, a complement protein that is part of the innate immune response, or a soluble immune pattern-recognition protein that is capable of identifying non-self or altered-self molecular patterns, coating the foreign microbes or altered/dying cells, and enhancing neutrophil reactivity against them by phagocytosis or complement attack (Litvack et al, 2010, *Innate Immunity* 16(3):191-200). Examples of soluble immune pattern-recognition proteins may include, but are not limited to, collectins, ficolins, pentraxins, sCD14, MFG-E8, natural IgM and C1q.

The term "lectin," as used herein, refers to any protein or fragment thereof, that is capable of binding a carbohydrate structure, e.g., a carbohydrate structure on a pathogen or a carbohydrate structure associated with a pathogen associated molecular pattern (PAMP). Lectins include both naturally occurring lectins or engineered lectins, e.g., engineered mannose binding lectins (MBL), surfactant protein D (SPD), or fragments thereof. For example, engineered mannose binding lectins include the carbohydrate recognition domain of MBL, e.g., the neck and lectin domains of MBL, e.g., amino acid residues 81 to 228 of MBL or amino acid residues 111 to 228 of MBL, fused downstream to the Fc portion of human IgG.

The term "pathogen", as used herein, refers to any pathogen or pathogen fragment capable of inducing an infectious disease in a subject. In some embodiments, the pathogen is an infectious microorganism selected from the group consisting of a bacterium, a fungus, a virus and a parasite, or a fragment thereof. The pathogen may comprise a whole infectious pathogen cell, or a part of the pathogen cell, e.g., a cell wall component of the infectious microorganism. In some embodiments, the pathogen comprises a pathogen-associated molecule pattern (PAMP), e.g., a pathogen fragment, a pathogen debris, a pathogen nucleic acid, a pathogen lipoprotein, a pathogen surface glycoprotein, a pathogen membrane component, or a component released from the pathogen. The term "pathogen" also includes a mycoplasma or a toxin released from the pathogen. The pathogen for use in a vaccine composition of the present invention causes disease or infection in the species of a subject, e.g., a mammal, to which the vaccine is administered, or in a closely related species. For example, the pathogen can be isolated from the same subject who receives the vaccine comprising the pathogen. Alternatively, the pathogen can be isolated from one subject having a pathogen infection and the vaccine composition comprising the pathogen is administered to a different subject having the same pathogen infection. Pathogens suitable for use in the vaccine compositions can also be derived from an in vitro culture, a microorganism lysate, a crude lysate, or a purified lysate, or alternatively, the pathogen may be a synthetic pathogen.

The term "pathogen associated molecular pattern" or "PAMP," as used herein, refers to any component of a microorganism that directs the targeted host cell to distinguish "self" from "non-self", e.g., infected pathogen, and promotes signals associated with innate immunity. Exemplary PAMPs may include, but not limited to, a pathogen fragment; a pathogen debris; a pathogen nucleic acid, including DNA (e.g., unmethylated CpG motifs), double-stranded RNA (dsRNA), single-stranded RNA (ssRNA), and 5'-triphosphate RNA; a pathogen lipoprotein; a pathogen surface glycoprotein; a pathogen membrane component such as peptidoglycans, glycosylphosphatidylinositol; and a component released from the pathogen, e.g., a toxin released from the pathogen. In some embodiments, the toxin is selected from the group consisting of endotoxin, lipopolysaccharide (LPS), lipoteichoic acid (LTA), wall teichoic acid (WTA) and Ricin.

The term "bioagent", as used herein, refers to any agent capable of recruiting an immune cell in a subject. The bioagent can be a naturally occurring, synthetically produced, or recombinantly produced compound. A bioagent suitable for use in the vaccine compositions of the claimed invention include adjuvants; cytokines, e.g., IL-1, IL-2, IL-3, IL-4, IL-5, IL-6, IL-7, IL-8, IL-10, IL-12, IL-15, IL-17, IL-18, interferon-γ (γ-IFN), IFN-α, tumor necrosis factor (TNF); or growth factors, e.g., transforming growth factor-α (TGF-α), TGF-β, granulocyte/macrophage colony stimulating factor (GM-CSF), granulocyte colony stimulating factor (G-CSF), fibroblast growth factor (FGF), nerve growth factor (NFG), neurotrophins, epidermal growth factor (EGF), platelet derived growth factor (PDGF), insulin-like growth factor (IGF), hepatocyte growth factor (HGF), erythropoietin (EPO), thrombopoietin 9TPO), myostatin (GDF-8), growth differentiation factor-9 (GDF-9), acidic fibroblast growth factor (aFGF or FGF-1), or basic fibroblast growth factor (bFGF or FGF-2).

The term "adjuvant", as used herein, refers to compounds that can be added to vaccines to stimulate immune responses against antigens. Adjuvants may enhance the immunogenicity of highly purified or recombinant antigens. Adjuvants may reduce the amount of antigen or the number of immunizations needed to protective immunity. For example, adjuvants may activate antibody-secreting B cells to produce a higher amount of antibodies. Alternatively, adjuvants can act as a depot for an antigen, present the antigen over a longer period of time, which could help maximize the immune response and provide a longer-lasting protection. Adjuvants may also be used to enhance the efficacy of a vaccine by helping to modify the immune response to particular types of immune system cells, for example, by activating T cells instead of antibody-secreting B cells depending on the purpose of the vaccine.

The term "scaffold," as used herein, refers to any structure comprising a biomaterial and capable of recruiting and activating an immune cell in a subject. The scaffold provides a physical structure onto which or into which the opsonin- or lectin-bound pathogen construct or the bioagent can associate or attach. The opsonin- or lectin-bound pathogen construct can be encapsulated within the scaffold for delivery or administration to a subject, therefore preventing any undesired leakage of pathogen from the vaccine composition. The scaffolds comprise a biocompatible material that is not toxic or immunogenic. As used herein, the term "biocompatible material" refers to any material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood.

The term "immune cell," as used herein, refers to any cell of the immune system that functions to protect the body against both infectious disease and foreign invaders. Exemplary immune cells include, but are not limited to, a T cell, a B cell, an antigen-presenting cell, a dendritic cell, a macrophage, a granulocytes, a monocyte, a neutrophil, and a natural killer (NK) cell. In some embodiments, the immune cell is an antigen-presenting cell.

The term "antigen-presenting cell," as used herein, refers to any cells that are capable of displaying antigen on their surfaces. Antigen-presenting cells process antigens into peptide fragments and present them on the cell surface to the T cells of the immune system. Antigen-presenting cells can be found in a variety of tissue types. Classical antigen-presenting cells, including macrophages, B cells, and dendritic cells, associate with an MHC class II molecule to present foreign antigens to helper T cells. While other cell types, e.g., mast cells, basophils, eosinophils, and group 3 innate lymphoid cells (ILC3s), that can express MHC class II molecules, may also serve as antigen-presenting cells (Kambayashi and Laufer, 2014, *Nature Reviews Immunology* 14, 719-730). Antigen-presenting cells may also include any cells, e.g., nucleated cells, that are capable of displaying endogenous peptides on the cell surface to cytotoxic T cells, typically using an MCH class I molecule. In addition to the MHC family of proteins, antigen presentation relies on other specialized signaling molecules on the surfaces of both APCs and T cells.

The term "lyophilization", as used herein, refers to a dehydration process used to preserve a composition, e.g., a vaccine composition, a scaffold composition and/or an opsonin-bound or lectin-bound pathogen construct of the present invention, or make the composition more convenient for storage and transport. Freeze-drying works by freezing the composition and then reducing the surrounding pressure to allow the frozen water in the composition to sublimate directly from the solid phase to the gas phase. In some embodiments, lyophilization increases the stability of the vaccine compositions of the claimed invention, thereby allows the vaccine compositions to be portable and to be stored at room temperature without the need of refrigeration.

By "treatment", "prevention" or "amelioration" of a disease or disorder, e.g., an infectious disease caused by a pathogen, is meant delaying or preventing the onset of such a disease or disorder, reversing, alleviating, ameliorating, inhibiting, slowing or stopping the progression, aggravation or deterioration, the progression or severity of a condition associated with such a disease or disorder, e.g., a pathogen infection. In one embodiment, the symptoms of a disease or disorder, e.g., a pathogen infection, or pain and distress associated with a pathogen infection, are alleviated by at least 5%, at least 10%, at least 20%, at least 30%, at least 40%, at least 50%, at least 60%, at least 70%, at least 80%, at least 90%, or at least 95%.

As used herein, a "subject" means a human or an animal. The animal may be a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, sheep, pigs, goats, birds, horses, pigs, deer, bison, buffalo, amphibians, reptiles, feline species, e.g., domestic cat, canine species, e.g., dog, fox, wolf, avian species, e.g., chicken, emu, ostrich, and fish, e.g., trout, catfish and salmon. In certain embodiments, the subject is an embryo or a fetus, where a life-long protection is elicited after vaccination with the present invention.

In certain embodiments, the subject is a mammal, e.g., a primate, e.g., a human. The terms, "patient" and "subject" are used interchangeably herein. Preferably, the subject is a mammal. The mammal can be a human, non-human primate, mouse, rat, dog, cat, horse, pig, sheep, goat, bird, reptile, amphibian, fish or cow. Mammals other than humans can be advantageously used as subjects that represent animal models of infectious diseases, or other related pathologies. A subject can be male or female. The subject can be an adult, an adolescent or a child. A subject can be one who has been previously diagnosed with or identified as suffering from or having a risk for developing an infectious disease, or disease and condition associated with pathogen infection.

II. Vaccine Compositions of the Invention

The invention provides vaccine compositions suitable for the prophylaxis and treatment of infectious diseases. The vaccine compositions comprise an opsonin- or lectin-bound pathogen construct and a bioagent capable of recruiting an immune cell in a subject.

The vaccine compositions of the present invention are tailored to activate immune cells and prime the cells with a specific antigen, e.g., a pathogen presented in the form of an opsonin-bound pathogen construct or in the form of a lectin-bound pathogen construct, thereby enhancing immune defenses and destruction against the undesired pathogen. The vaccine compositions attract appropriate immune cells, such as macrophages, T cells, B cells, natural killer cells, and dendritic cells.

Any pathogen or pathogen fragment that is capable of inducing an infectious disease in a subject may be used in the vaccine compositions of the invention. In some embodiments, a pathogen is an infectious microorganism, including both the whole infectious pathogen cell, or any cellular fragments of the infectious microorganism, e.g., cell wall components of the infectious microorganism. In other embodiments, the pathogen comprises pathogen-released materials, pathogen debris, pathogen toxins, or pathogen-associated molecule patterns (PAMPs). In some embodiments, the cell wall components of the infectious microorganism are glycosylated. In other embodiments, the cell wall components are mannosylated. In some embodiments, the cell wall components are mannose-capped lipoarabinomannan (ManLAM). In other embodiments, the cell wall components are phosphatidylinositol mannoside (PIM).

Examples of pathogens that are suitable for use in the vaccine compositions include, but are not limited to, a bacterium, a virus, a viroid, a mycoplasma, a parasite, a fungus or a fragment thereof. A bacteria may be a member of the genus *Neisseria, Aerobacter, Pseudomonas, Porphyromonas, Salmonella, Escherichia, Pasteurella, Shigella, Bacillus, Helibacter, Corynebacterium, Clostridium, Mycobacterium, Yersinia, Staphylococcus; Bordetelia, Brucelia, Vibrio, Streptococcus, Plasmodium, Schisostoma* or *Candida*. Exemplary bacteria may also include, but are not limited to, *Acinetobacter baumanii, Burkholderia cepacia, Bacterioides fragilis, Chlamydia trachomatis, Citrobacter freundii, Campylobacter jejuni, Escherichia coli, Enterobacter aerogenes, Enterobacter cloacae, Haemophilus inf*b, *Helicobacter pylori, Klebsiella oxytoca, K. pneumonia* (MDR/CRE), *Legionella pneumophila, Neisseria meningitides, Neisseria gonorrhoeae, Pseudomonas aeruginosa, Salmonella typhi, paratyphi, typhimurium, Serratia marcescens, Shigella flexneri, Stenotrophomonas maltophilia, Yersinia pseudotuberculosis, Bacillus subtilis, Clostridium neoformans, C. difficile, C. perfringens, Corynebacterium* spp, *Enterococcus faecalis, Enterococcus faecium*, vancomycin-resistant *Enterococci* (VRE), *Listeria monocytogenes, Mycobactrium avium, M. tuberculosis, M. leprae, Nocardia farcinica, P. acnes, Staphylococcus aureus*, methicillin-susceptible *Staphylococcus aureus* (MSSA), methicillin-resistant *Staphylococcus aureus* (MRSA), *Staphylococcus epidermidis, Streptococcus pyogenes*, Strep Group A, Strep Group B (agalactiae) and Strep Group C.

In some embodiments, the bacterium is an antibiotic-resistant bacterium. In some embodiment, the bacterium is a multi-drug resistant bacterium. In other embodiments, the antibiotic-resistant bacterium or the multi-drug resistant bacterium is selected from the group consisting of *Acinetobacter baumanii, Escherichia coli, Klebsiella oxytoca, K. pneumonia* (MDR/CRE), *Pseudomonas aeruginosa, C. difficile*, vancomycin-resistant *Enterococci* (VRE) and methicillin-resistant *Staphylococcus aureus* (MRSA).

Any fungus may be used in the vaccine compositions of the present invention. Exemplary fungi may include, but are not limited to, *Aspergillus* spp, *Blastomyces, Candida albicans, glabrata, guilliermondii, krusei, parapsilosis, tropicalis Cryptococcus, Fusarium* spp., *Mucor* spp., *Saccharomyces*, and *Pneumocystis jirovecii (carinii)*.

Exemplary viruses for use in the vaccine compositions of the present invention may include, but are not limited to, influenza virus, Dengue virus, Ebola virus, EBV, Hepitis A virus, Hepitis B virus, Hepitis C virus, Hepitis D virus, HSV 1, HSV 2, Cytomegalovirus (CMV), Influenza A virus, Marburg virus, human respiratory syncytial virus (RSV), SARS-CoV, West Nile virus, human papillomavirus (HPV), human rhinoviruses (HRVs), Zica virus, human immunodeficiency virus (HIV-1 and HIV-2), human T-cell leukemia virus (HTLV), poliomyelitis virus, pox virus, measles virus, arbor virus, Coxsackie virus, herpes virus, hantavirus, Baculovirus, mumps virus, circovirus, vichaivirus, arenavirus, rotavirus, cytomegalovirus, avian leukosis-sarcoma virus (ALV), murine leukemia virus (MLV), feline leukemia virus (FeLV), simian sarcoma virus (SIS), mouse mammary tumor virus (MMTV), Mason-Pfizer monkey virus (MPMV), simian AIDS viruses (SRVs), simian T-cell leukemia virus (SUN), bovine leukemia virus (BLV), simian immunodeficiency virus (SIV), feline immunodeficiency virus (FTV), Visna/maedi virus (VMV), equine infectious anemia virus (EIAV) and caprine arthritis-encephalitis virus (CAEV).

Exemplary parasites for use in the vaccine compositions of the present invention may include, but are not limited to, *Cryptosporidium, Leishmania, Malaria, Schistosoma, Trichomonasm* and *Trypanosoma*. Exemplary mycoplasma for use in the vaccine compositions of the present invention may include, but are not limited to, *M. pneumoniae, M. hominis* and *M. orale*.

In some embodiments, the pathogen comprises pathogen associated molecular patterns (PAMPs). The term "pathogen associated molecular pattern", as used herein, refers to any component of a microorganism that is recognized by cells of the innate immune system in the host (Tang et al., 2012, *Immunol Rev.*, 249(1): 158-175 and Sangiuliano et al., 2014, *Mediators of Inflammation*, Article ID 821043). Specifically, since PAMPs are present in diverse organisms, but absent in the host, they provide exogenous danger signals, that are recognized by specific receptors in host cells and alert the host immune system to the presence of pathogens, thereby promoting immunity.

Exemplary PAMPs may include, but are not limited to, a pathogen fragment; a pathogen debris; a pathogen nucleic acid, including DNA (e.g., unmethylated CpG motifs), double-stranded RNA (dsRNA), single-stranded RNA (ssRNA), and 5'-triphosphate RNA; a pathogen lipoprotein; a pathogen surface glycoprotein; a pathogen membrane component such as peptidoglycans, glycosylphosphatidylinositol; and a component released from the pathogen, e.g., a toxin released from the pathogen. In some embodiments, the toxin is selected from the group consisting of endotoxin, lipopolysaccharide (LPS), lipoteichoic acid (LTA), wall teichoic acid (WTA) and Ricin.

PAMPs can be recognized by pattern recognition receptors (PPRs) such as Toll-like receptors (TLRs) and other PRRs, such as retinoid acid-inducible gene I (RIG-I)-like receptors (RLRs), AIM2 like receptors (ALRs), and nucleotide-binding oligomerization domain (NOD)-like receptors (NLRs). Following PAMP recognition, activated TLRs and other PRRs localized to the cell surface, the cytoplasm, and/or intracellular vesicles provide signals to the host indicating the presence of a microbial infection and trigger proinflammatory and antimicrobial responses by activating a multitude of intracellular signaling pathways, including adapter molecules, kinases, and transcription factors such as nuclear factor-κB (NF-κB), activator protein-1 (AP-1), and IFN regulatory factors (IRFs). PAMP-induced signal transduction pathways ultimately result in the activation of gene expression and the synthesis of a broad range of molecules, including cytokines, chemokines, cell adhesion molecules, and immunoreceptors that direct the adaptive immune response to invading pathogens by sensing microorganisms.

An effective amount of a pathogen or a pathogen fragment should be included in the vaccine composition. The effective amount of a pathogen or a pathogen fragment is the amount sufficient to produce an immune response, e.g., an antibody secreting B cell or cytotoxic T cell mediated immune response, directed against one or more of the pathogen or pathogen fragments of the vaccine compositions of the invention. The ability of the vaccine compositions of the invention to elicit an immune response can be determined using any routine method available to those of skill in the art. In some embodiments, the effective amount of each composition is the amount sufficient to produce a cytotoxic T cell response in the subject as measured, for example, by a mixed lymphocyte T cell assay.

In some embodiments, the pathogens or pathogen fragments are present in the vaccine composition at an amount of about 1 pg to about 1000 μg. In some embodiments, the amount of pathogens or pathogen fragments is 1 μg to 100 μg, 1 μg to 200 μg, 1 μg to 300 μg, 1 μg to 400 μg, 1 μg to 500 μg, 1 μg to 600 μg, 1 μg to 700 μg, 1 μg to 800 μg, or 1 μg to 900 μg. In some embodiments, the amount of pathogens or pathogen fragments is 1 μg to 10 μg, 1 μg to 20 μg, 1 μg to 30 μg, 1 μg to 40 μg, 1 μg to 50 μg, 1 μg to 60 μg, 1 μg to 70 μg, 1 μg to 80 μg, or 1 μg to 90 μg. In some embodiments, the amount of pathogens or pathogen fragments is 1 pg to 100 μg, 1 pg to 90 μg, 1 pg to 80 μg, 1 pg to 70 μg, 1 pg to 60 μg, 1 pg to 50 μg, 1 pg to 40 μg, 1 pg to 30 μg, 1 pg to 20 μg or 1 pg to 10 μg. In other embodiments, the amount of pathogens or pathogen fragments is 10 pg to 1 μg, 20 pg to 1 μg, 30 pg to 1 μg, 40 pg to 1 μg, 50 pg to 1 μg, 60 pg to 1 μg, 70 pg to 1 μg, 80 pg to 1 μg, 90 pg to 1 μg, 100 pg to 1 μg, or 1000 pg to 1 μg.

Pathogens for use in the vaccine compositions of the present invention are neutralized. For example, a pathogen is neutralized by treatment with antibiotics, ultraviolet light, sonication, microwave, bead mill, x-ray, autoclave, irradiation or mechanical disruption. Pathogens become non-infectious after neutralization. Use of non-infectious pathogens in a vaccine composition is beneficial and can reduce the potentially severe side effects experienced with pathogen toxins.

The vaccine compositions of the present invention may comprise one or more types of pathogens to create a monovalent or multivalent vaccine. In some embodiments, the vaccine compositions comprise one type of pathogen. In other embodiments, the vaccine compositions comprise multiple types of pathogens, e.g., at least 2, 3, 4, 5, 6, 7, 8, 9, or 10 different types of pathogens, such as 2, 3, 4, 5, 6, 7, 8, 9, 10, 1-4, 1-5, 2-5, 2-10, 3-6, 3-10 or 5-10 different types of pathogens.

The vaccine compositions of the present invention can also be used to vaccinate across species of a given pathogen. For example, the claimed vaccine compositions comprising one specific species or strain of a pathogen can be used to vaccinate against multiple related species or strains of the pathogen. The ability to vaccinate across species for a given pathogen is particularly advantageous, especially for pathogens that have multiple species or strains with different surface antigens. For those pathogens, inconsistency in the antigen structure between the vaccine strain and the infected strain would normally be a significant problem. For example, when a pathogen strain, which is different from the vaccine strain, causes an infectious disease, the vaccination would be rendered ineffective. However, this would not be a problem with the claimed vaccine compositions given their superior ability to target multiple species of a particular pathogen.

Pathogens suitable for use in the vaccine compositions of the invention can be obtained from any sources. For example, a pathogen can be isolated directly from a sample derived from a subject in vivo. In some embodiments, the pathogen is isolated from the same subject who receives the vaccine comprising the pathogen. In other embodiments, the pathogen is isolated from one subject having a pathogen infection and the vaccine composition comprising the pathogen is administered to a different subject having the same or similar pathogen infection. For example, the pathogen can be isolated from a human subject, and administered to a different human subject infected with the same pathogen or related species of the pathogen. Alternatively, the pathogen can be isolated from a subject, e.g., an animal, and administered to a different subject, e.g., a human, infected with the same pathogen or related species of the pathogen.

Examples of samples suitable for pathogen isolation include, but are not limited to, a blood sample, a plasma sample, a serum sample, a blood culture sample, a cerebrospinal fluid sample, a joint fluid sample, a urine sample, a semen sample, a saliva sample, a sputum sample, a bronchial fluid sample, and a tear sample.

Alternatively, pathogens suitable for use in the vaccine compositions can be derived from an in vitro culture, a microorganism lysate, a crude lysate, or a purified lysate. In another embodiment, the pathogen may be a synthetic pathogen.

Pathogens for use in the vaccine compositions are isolated using known methods in the art. In some embodiments, the pathogen is isolated from a sample using an opsonin or a lectin and presented in the form of an opsonin-bound pathogen construct or a lectin-bound pathogen construct in a vaccine composition.

As demonstrated in Example 1, pathogen fragments isolated using a lectin demonstrate an unexpected advantage over the direct use of a microorganism lysate, e.g., a bacterial lysate. Although both the bacterial lysate and the lectin captured bacterial fragments may be used to generate functional vaccine compositions and protect mice from a lethal challenge of bacterial infection, the direct use of a bacterial lysate in a vaccine composition was associated with undesirable side effects such as leaching of the lysate and formation of abscesses at the site of administration. Therefore, the lectin or opsonin, not only functions to isolate a pathogen for use in the vaccine compositions and present the pathogen to immune cells in order to elicitate long-term immune response, but also serves as an anchor structure to immobilize the pathogen, thereby preventing leakage of the pathogen from the vaccine composition.

Direct isolation of a pathogen using a lectin or an opsonin confers additional benefit, for example, when a particular pathogen or pathogen fragment, e.g., LPS, is difficult to purify, or when a pathogen is unknown or hard to culture, addition of the lectin or opsonin into a microorganism lysate would facilitate the isolation of a desired pathogen, thereby forming the opsonin- or lectin-bound pathogen construct that can be used in the vaccine compositions.

An opsonin suitable for use in the vaccine compositions of the present invention includes any protein or fragment thereof, that can recognize a surface molecule of a pathogen cell, e.g., a pathogen associated molecular pattern, thereby targeting the opsonin-bound pathogen cell for destruction by complement attack and phagocytosis.

In some embodiments, the opsonin in the opsonin-bound pathogen construct is a natural opsonin or a portion thereof, such as an antibody that is generated by B cells in response to antigen exposure, a complement protein that is part of the innate immune response, or a soluble immune pattern-recognition protein that is capable of identifying non-self or altered-self molecular patterns, coating the foreign microbes or altered/dying cells, and enhancing neutrophil reactivity against them by phagocytosis or complement attack (Litvack et al, 2010, Innate Immunity 16(3):191-200). Typically, foreign pathogens display altered arrays of molecules on their surfaces. For example, cell surfaces of foreign microbes often contain, or allow the access to different lipids, intracellular glycoproteins and nucleic acids such as DNA than those from host cells. These cell surface patterns are considered as signals for opsonin molecules, which will mark and target the recognized cells for killing. Similarly, a programmed cell death process such as apoptosis also generates cell surface blebs that contain intracellular components. These blebs are easily released for effective clearance or signaling. During late stages of cell death, soluble components such as lysoPC and nucleotides are also released that act as signals for opsonin molecules. (Litvack et al, 2010, Innate Immunity 16(3):191-200). Examples of soluble immune pattern-recognition protein may include, but not limited to, collectins, ficolins, pentraxins, sCD14, MFG-E8, natural IgM and C1q which can effectively identify some of these specific molecular patterns.

Engineered opsonins or lectins, e.g., engineered mannose binding lectins, surfactant protein D, or fragments thereof, may also be used in the vaccine compositions of the present invention. With the use of genetic engineering, and direct evolution and selection strategies, modified versions of natural opsonins or lectins can be engineered. Such engineered opsonin or lectin molecules may be used to bind pathogens or identify specific pathogen species for use in the vaccine composition for treatment and diagnosis of patients with infectious diseases.

In some embodiments, the opsonin-bound or lectin-bound pathogen construct comprises a lectin, a portion of a lectin, an engineered lectin or a portion thereof. In some embodiments, the lectin is a collecin. In other embodiments, the lectin is a ficolin.

In some embodiments, the lectin comprises pulmonary surfactant protein D (SPD). In other embodiments, the surfactant protein D (SPD) is capable of binding to the pathogen. Pulmonary surfactant, a complex mixture of lipids and proteins, is essential for lung function. Pulmonary surfactant protein D (SPD) has a significant role in immune and inflammatory regulation of the lung as it regulates of the level of surfactant in the lungs and acts as a host defense protein.

In some embodiments, the lectin is a mannose-binding lectin (MBL). MBL is a serum lectin that binds to mannose, N-acetylglucos amine (NAG)-containing carbohydrates, and various other carbohydrates that are present on the surface of many microbial pathogens. MBL (also called mannose- or mannan-binding protein, MBP) is a polymeric protein assembled from three or more 32 kDa monomers. Each monomer has an N-terminal cysteine rich region, a collagen-like gly-X-Y region, a neck region and a carbohydrate recognition domain. The assembly of the higher molecular weight polymers begins with formation of trimers of the 32 kDa monomer; these trimers then self-assembly into higher molecular weight polymers of three to six sets of trimers.

MBL is a key component in opsonization of microbial pathogens and in the activation of complement (via the lectin pathway) and coagulation. Opsonization is the binding of proteins to target cells and then targeting these cells for uptake and destruction by phagocytic cells, such as macrophages and neutrophils. This opsonization appears to be mediated by the small, cysteine-rich N-terminal domain of MBL as well as C3b deposited on the target cell surface by MBL-mediated lectin complement pathway activation. In the activation of complement via the lectin pathway, the microbe and specialized proteins, i.e., MASP-1 (Mannan-binding lectin Associated Serine Protease) and MASP-2, interact with bound MBL and activate complement in the absence of antibody (Matsushita & Fujita, 1992, J. Exp. Med. 176(5): 1497-1502; Thiel et al., 1997, Nature 386: 506-510). The higher molecular weight MBL complexes (5 to 6 repeats of the functional MBL trimer) are potent activators of complement via this lectin pathway, in which MASP 2 appears to activate complement, and MASP 1 activates coagulation. The smaller complexes (three to four repeats of the MBL trimer unit) are the most potent activators of coagulation (Krarup et al., 2007 PLoS One, 2(7), e623).

MBL is an excellent choice for use in the vaccine compositions described herein; however, the intact molecule is not typically used in the presence of whole blood because the wild type MBL has multiple functional domains that can activate phagocytosis, blood coagulation and complements, which could interfere with or complicate therapeutic vaccine function. This characteristic of MBL can be separated from its pathogen binding function as provided herein. More specifically, MBL contains four parts, from N- to C-terminus: a small N-terminal domain of essentially unknown function that may be involved in macrophage binding and/or MASP binding; a collagen segment that may also be involved in MASP binding and higher-order oligomerization; an alpha-helical "neck" segment that is sufficient for trimerization; and the carbohydrate recognition lectin domain at the C-terminus that mediates direct pathogen binding. The lectin domain is useful for the present invention for isolation of pathogens. In some embodiments, the lectin comprises the neck and lectin domains of MBL. For example, the lectin may comprise amino acid residues 81 to 228 of MBL (SEQ ID NO: 1), or amino acid residues 111 to 228 of MBL. See, e.g., U.S. Pat. No. 9,150,631. The entire contents of the foregoing patent are incorporated herein by reference.

Amino acid residues 81-228 of human MBL (which includes the coiled coil neck region and the carbohydrate recognition domains (CRD) of human MBL: 81 pdgdsslaas erkalqtema rikkwltfsl gkqvgnkffl tngeimtfek vkalcvkfqa 141 svatprnaae ngaiqnlike eaflgitdek tegqfvdltg nrltytnwne gepnnagsde 201 dcvlllkngq wndvpcstsh lavcefpi (SEQ ID NO: 1).

The binding characteristics of a lectin, e.g., MBL, can be manipulated by directed evolution for altered binding specificity. MBL may be modified so that it binds to a limited set of sugars or other molecular features, such that the modified MBL will bind to a selected set of microbes to provide a more specific capability for pathogen class capture. For example, the engineered MBL may be capable of capture certain pathogen class, e.g., one or more bacterial species, e.g., gram negative bacteria or gram positive bacteria; one or more viruses species; one or more fungi species; or one or more protozoan species.

For example, the engineered lectin, e.g., MBL, for use in the vaccine compositions of the present invention may be generated by looking at an atomic structure of MBL complexed with a sugar, and then mutating appropriate amino acids that make contact in a sugar-specific manner, such that distinctive contacts are lost or particular types of steric hindrance are created. For example, the three dimensional structure of rat MBL has been solved in a complex with a high-mannose oligosaccharide, with N-acetylglucosamine, and with a methylated fucose. His189Val and Ile207Val are examples of substitutions that modifications alter specificity.

A directed evolution strategy can be applied to MBL in order to select MBL variants with specific binding to a specific type of pathogen, for example, yeast, gram-positive bacteria, gram-negative, coagulase negative, and aerobic bacteria. Derivatives of MBL with a particular specificity can be isolated by any method known in the art, for example, a standard phage display strategy. First, a set of MBL variants can be expressed from a phagemid vector; then binds this library to a target of interest (e.g., E. coli) and one or two rounds of selection may be performed. Subsequently, a round of negative selection against a related target (e.g., Candida) is followed, taking those phagemids that fail to bind. These cycles of positive and negative selection are then repeated until a population of phages that generally bind to the target and do not bind to the non-target is generated. This method may be applied to any pair of microbial strains against which differential binding is desired, such as bacteria that are resistant and sensitive to a given antibiotic.

MBL belongs to the class of collectins in the C-type (calcium-dependent) lectin superfamily, other members of which, such as surfactant protein A, surfactant protein D, CL-L1 and CL-P1, may be useful for construction of engineered lectins for use in the vaccine compositions of the present invention. Other possible lectins include ficollin which can also activate the lectin pathway of complement and bind MASP proteins. Ficollin proteins are related to MBL but have a different, and a more limited specificity. In the context of the vaccine compositions described herein, one option is to use the lectin domain of a ficollin that corresponds to the lectin domain of MBL described above. Another approach is to use 'shuffling' of segments or individual amino acids between MBL and one or more Ficollins to create hybrid molecules that may have hybrid specificities. The directed evolution and selection approach described above also could potentially be used to generate engineered proteins that provide the class, subclass and species specificity.

The opsonin or lectin, e.g., engineered MBL or SPD, may further comprise an immunoglobulin Fc portion. For example, the neck and lectin domains of MBL may be fused downstream to the Fc portion of human IgG. The Fc portion may include the CH2-CH3 interface of the IgG Fc domain, which contains the binding sites for a number of Fc receptors including Staphylococcal protein A. In use, the Fc portion dimerizes and strengthens the avidity affinity of the binding by MBL lectins to monomeric sugars. Additionally, the n-linked glycosylation of the recombinant lectin can be removed. For example, when the neck and lectin domains of MBL, e.g., amino acid residues 81-228 of MBL, are fused with the Fc portion of IgG, the glycosylation of the resulting fusion protein can be removed by changing the amino acid at residue 297 from asparagine to aspartic acid (N297D) in the Kabat system of numbering amino acids in antibodies, which corresponds to amino acid 82 in this particular FcMBL construct.

The opsonin or lectin, e.g., engineered MBL or SPD, may further comprise a solid substrate. Any solid substrate that is for attachment of the fusion MBL lectin-Fc or SPD-Fc protein can be used in the vaccine composition of the present invention. The solid substrate may facilitate a long-term presentation of pathogen to an immune cell. Examples of solid substrates may include, but not limited to, a bead, e.g., a magnetic bead, a microporous membrane, a hollow-fiber reactor, a blood filtration membrane and a blood flow device.

In some embodiments, the solid substrate may comprise beads, e.g., magnetic beads, or other structured materials, which then pull pathogens out from a sample (including biological fluids such as blood or in vitro pathogen cultures, and any other samples as described above), and concentrate and collect the pathogens, including living pathogens. Alternatively, the solid substrate may comprise a hollow-fiber reactor or any other blood filtration membrane or flow device (e.g., a simple dialysis tube) or other resins, fibers, or sheets to selective bind and sequester the biological pathogens.

The beads, e.g., magnetic beads, can be of any shape, including but not limited to spherical, rod, elliptical, cylindrical, disc, and the like. In some embodiments, beads, e.g., magnetic beads, having a true spherical shape and defined surface chemistry are used to minimize chemical agglutination and non-specific binding. As used herein, the term "magnetic bead" refers to a nano- or micro-scale particle that is attracted or repelled by a magnetic field gradient or has a non-zero magnetic susceptibility. The magnetic bead can be paramagnetic or super-paramagnetic. In some embodiments, magnetic beads are super-paramagnetic. Magnetic beads are also referred to as magnetic particles. In some embodiments, magnetic beads having a polymer shell are used to protect the pathogen from exposure to iron. For example, polymer-coated magnetic beads can be used to protect pathogens from exposure to iron.

The beads, e.g., magnetic beads, can range in diameter from 1 nm to 1 mm. For example, beads, e.g., magnetic beads, are about 50 nm in diameter, about 128 nm in diameter, about 500 nm in diameter, about 1 µm in diameter, about 250 nm to about 250 µm in diameter, 0.1 µm to 100 µm in diameter, 0.1 µm to 50 µm in diameter, or 0.1 µm to 10 µm in diameter. In some embodiments, the magnetic bead is a magnetic nano-particle or magnetic micro-particle. Magnetic nanoparticles are a class of nanoparticle which can be manipulated using magnetic field or magnetic field gradient. Such particles commonly consist of magnetic elements such as iron, nickel or cobalt. Magnetic nano-particles are well-known and methods for their preparation have been described in the art. See, e.g., U.S. Pat. Nos. 6,878,445; 5,543,158; 5,578,325; 6,676,729; 6,045,925; and 7,462,446; and U.S. Patent Publications No. 2005/0025971; No. 2005/0200438; No. 2005/0201941; No. 2005/0271745; No. 2006/0228551; No. 2006/0233712; No. 2007/01666232; and No. 2007/0264199. The entire contents of the foregoing patents and patent applications are incorporated herein by reference.

Magnetic beads for use in the vaccine compositions of the present invention are easily and widely available commercially, with or without functional groups capable of binding to affinity molecules. Suitable magnetic beads are commercially available such as from Dynal Inc. (Lake Success, N.Y.); PerSeptive Diagnostics, Inc. (Cambridge, Mass.); Invitrogen Corp. (Carlsbad, Calif.); Cortex Biochem Inc. (San Leandro, Calif.); and Bangs Laboratories (Fishers, Ind.). In particular embodiments, magnetic particles are MyOne™ Dynabeads® magnetic beads (Dynal Inc.).

The opsonin or lectin, e.g., engineered opsonin or lectin, can be conjugated with a solid substrate by methods well known in the art for conjugating peptides with other molecules. For example, Hermanson, Bioconjugate Techniques (2nd Ed., Academic Press (2008)) and Niemeyr, *Bioconjugation Protocols: Strategies & Methods*, in Methods In Molecular Biology (Humana Press, 2004), provide a number of methods and techniques for conjugating peptides to other molecules.

Alternatively, the surface of the solid substrate can be functionalized to include binding molecules that bind selectively with the opsonin or lectin. These binding molecules are also referred to as affinity molecules. The binding molecule can be bound covalently or non-covalently on the surface of the solid substrate. As used herein, the term "binding molecule" or "affinity molecule" refers to any molecule that is capable of specifically binding an engineered opsonin or lectin described herein. Representative examples of binding molecules include, but are not limited to, antibodies, antigens, proteins, peptides, nucleic acids (DNA, RNA, PNA and nucleic acids that are mixtures thereof or that include nucleotide derivatives or analogs); receptor molecules, such as the insulin receptor; ligands for receptors (e.g., insulin for the insulin receptor); and biological, chemical, polymeric or other molecules that have affinity for another molecule, such as biotin and avidin.

Binding molecules can be conjugated to surface of the solid substrate using any of a variety of methods known to those of skill in the art. The binding molecule can be coupled or conjugated to surface of the solid substrate covalently or non-covalently. The covalent linkage between the binding molecule and the surface can also be mediated by a linker. The non-covalent linkage between the binding molecule and the surface can be based on ionic interactions, van der Waals interactions, dipole-dipole interactions, hydrogen bonds, electrostatic interactions, and/or shape recognition interactions.

The vaccine compositions of the present invention comprise one or more bioagents. As used herein, the term "bioagent" refers to any agent capable of recruiting an immune cell in a subject. The bioagent can be naturally occurring, synthetically produced, or recombinant compounds. A bioagent suitable for use in the vaccine compositions of the claimed invention include adjuvants; cytokines, e.g., IL-1, IL-2, IL-3, IL-4, IL-5, IL-6, IL-7, IL-8, IL-10, IL-12, IL-15, IL-17, IL-18, interferon-γ (γ-IFN), IFN-α, tumor necrosis factor (TNF); or growth factors, e.g., transforming growth factor-α (TGF-α), TGF-β, granulocyte/macrophage colony stimulating factor (GM-CSF), granulocyte colony stimulating factor (G-CSF), fibroblast growth factor (FGF), nerve growth factor (NFG), neurotrophins, epidermal growth factor (EGF), platelet derived growth factor (PDGF), insulin-like growth factor (IGF), hepatocyte growth factor (HGF), erythropoietin (EPO), thrombopoietin 9TPO), myostatin (GDF-8), growth differentiation factor-9 (GDF-9), acidic fibroblast growth factor (aFGF or FGF-1), or basic fibroblast growth factor (bFGF or FGF-2).

Suitable bioagents useful in accordance with the invention include, but are not limited to, DNA molecules, RNA molecules, antisense nucleic acids, ribozymes, plasmids, expression vectors, marker proteins, transcription or elongation factors, cell cycle control proteins, kinases, phosphatases, DNA repair proteins, oncogenes, tumor suppressors, angiogenic proteins, anti-angiogenic proteins, cell surface receptors, accessory signaling molecules, transport proteins, enzymes, anti-bacterial agents, anti-viral agents, antigens, immunogens, apoptosis-inducing agents, anti-apoptosis agents, cytotoxins, and antibodies against immunosuppression (e.g., transforming growth factor (TGF)-beta antibody or antagonists, and adenosine (A2aR) antagonists).

Bioagents suitable for use in the present invention may also include, but are not limited to, growth factors, hormones, neurotransmitters, neurotransmitter or growth factor receptors, interferons, interleukins, chemokines, cytokines, colony stimulating factors, chemotactic factors, MMP-sensitive substrate, extracellular matrix components. Exemplary bioagents include, but are not limited to, growth hormone, parathyroid hormone (PTH), bone morphogenetic protein (BMP), transforming growth factor-α (TGF-α), TGF-β, fibroblast growth factor (FGF), granulocyte/macrophage colony stimulating factor (GM-CSF), granulocyte colony stimulating factor (G-CSF), nerve growth factor (NFG), neurotrophins, epidermal growth factor (EGF), platelet derived growth factor (PDGF), insulin-like growth factor (IGF), vascular endothelial cell growth factor (VEGF), hepatocyte growth factor (HGF), erythropoietin (EPO), thrombopoietin 9TPO), myostatin (GDF-8), growth differentiation factor-9 (GDF-9), acidic fibroblast growth factor (aFGF or FGF-1), basic fibroblast growth factor (bFGF or FGF-2), interferon-γ (γ-IFN), IFN-α, tumor necrosis factor (TNF), fibrin, collagen, fibronectin, vitronectin, hyaluronic acid, RGD-containing peptides or polypeptides, IL-1, IL-2, IL-3, IL-4, IL-5, IL-6, IL-7, IL-8, IL-10, IL-12, IL-15, IL-17, IL-18, FLT-3 ligand, and CD40 ligand. Splice variants of any of the above mentioned proteins, and small molecule agonists or antagonists thereof that may be used advantageously to alter a function of a cell are also contemplated herein.

In some embodiments, the bioagent comprises one or more adjuvants. Adjuvants are compounds that enhance the specific immune response against antigens. Adjuvants are added to vaccines to stimulate the immune system's response to the target antigen. Adjuvants may enhance the immunogenicity of highly purified or recombinant antigens. Adjuvants may reduce the amount of antigen or the number of immunizations need to protective immunity. For example, adjuvants may activate antibody-secreting B cells to produce a higher amount of antibodies. Alternatively, adjuvants can act as a depot for an antigen, present the antigen over a longer period of time, which could help maximize the immune response and provide a longer-lasting protection. Adjuvants may also be used to enhance the efficacy of a vaccine by helping to modify the immune response to particular types of immune system cells, for example, by activating T cells instead of antibody-secreting B cells depending on the purpose of the vaccine. Adjuvants are also used in the production of antibodies from immunized animals (Petrovskyl et al, 2002, *Immunology and Cell Biology* 82: 488-496).

Adjuvants can be classified according to their source, mechanism of action or physicochemical properties. For example, adjuvants can be classified into three groups: (i) active immunostimulants, being substances that increase the immune response to the antigen; (ii) carriers, being immunogenic proteins that provide T-cell help; and (iii) vehicle adjuvants, being oil emulsions or liposomes that serve as a matrix for antigens as well as stimulating the immune response (Edelman R. 1992, *AIDS Res. Hum. Retroviruses* 8: 1409-11). An alternative adjuvant classification divides adjuvants according to administration route, namely mucosal or parenteral. A third classification divides adjuvants into alum salts and other mineral adjuvants; tensoactive agents; bacterial derivatives; vehicles and slow release materials or cytokines (Byars et al., 1990, *Laboratory Methods in Immunology:* 39-51). A fourth classification divides adjuvants into the following groups: gel-based adjuvants, tensoactive agents, bacterial products, oil emulsions, particulated adjuvants, fusion proteins or lipopeptides (Jennings R et al., 1998, *Dev. Biol. Stand*, 92: 19-28).

The vaccine compositions of the present invention may comprise one or more adjuvants. Adjuvants suitable for use in the present invention include, but are not limited to, mineral salt-based adjuvants such as alum-based adjuvants, calcium-based adjuvants, iron-based adjuvants, zirconium-based adjuvants; particulate adjuvants; mucosal adjuvants; tensoactive adjuvants; bacteria-derived adjuvants; oil-based adjuvants; cytokines, liposome adjuvants, polymeric microsphere adjuvants, carbohydrate adjuvants.

Exemplary adjuvants include, but are not limited to, aluminium hydroxide, aluminum phosphate, calcium phosphate, Quil A, Quil A derived saponin QS-21, or other types of saponins, Detox, ISCOMs, cell wall peptidoglycan or lipopolysaccharide of Gram-negative bacteria, trehalose dimycolate, bacterial nucleic acids such as DNA containing CpG motifs, FIA, Montanide, Adjuvant 65, Freund's complete adjuvant, Freund's incomplete adjuvant, Lipovant, interferon, granulocyte-macrophage colony stimulating factor (GM-CSF), AS03, AS04, IL-1, IL-2, IL-3, IL-4, IL-5, IL-6, IL-7, IL-8, IL-10, IL-12, IL-15, IL-17, IL-18, STING, Toll-like receptor ligand, CD40L, ovalbumin (OVA), monophosphoryl lipid A (MPL), poly(I:C), a combination of LPS (or MPLA) and OxPAPC, MF59, N-acetyl muramyl-L-alanyl-D-isoglutamine (MDP), poly (DL-lactide-coglycolide) microspheres, paraffin oil, squalene, virosome, gamma inulin, glucans, dextrans, lentinans, glucomannans and galactomannans, pathogen-associated molecular patterns (PAMPs), damage-associated molecular pattern molecules (DAMPs), antibodies against immune suppressive molecules (e.g., antibody or antagonist against transforming growth factor (TGF)-beta, A2aR antagonists), Freund's complete adjuvant, Freund's incomplete adjuvant, lipopolysaccharides (LPS), Fas ligand, Trail, lymphotactin, Mannan (M-FP), APG-2, Hsp70 and Hsp90.

Adjuvants may comprise any number of delivery systems, for example, mineral salts, surface active agents, synthetic micro particles, oil-in-water emulsions, immunostimulatory complexes, liposomes, virosomes, and virus-like particles. Adjuvants may further comprise one or more potentiators of the immune response such as microbial derivatives (e.g., bacterial products, toxins such as cholera toxin and heat labile toxin from *E. coli*, lipids, lipoproteins, nucleic acids, peptidogylcans, carbohydrates, peptides), cells, cytokines, (e.g., dendritic cells, IL-12, and GM-CSF), hormones, and small molecules. Adjuvants suitable for use in the present invention include, but are not limited to, oil-based adjuvants (e.g., Freund's adjuvant), CpG oligonucleotides, aluminum salt adjuvants, calcium salt adjuvants, emulsions and surfactant-based formulations (e.g., MF59, AS02, montanide, ISA-51, ISA-720, and QA21). For a review of improvements in vaccine adjuvants, see Pashine et al. 2005, *Nature Med.* 11(4): S63-S68.

In one embodiment, the adjuvant comprises or consists of one or more toll-like receptor (TLR) agonists. In one embodiment, the TLR agonist is a pathogen associated agonist selected from the group consisting of triacylated lipopeptides (gram positive bacteria), Peptidoglycan (gram positive bacteria), bacterial lipoprotein, lipoteichoic acid, LPS (*Porphyromonas gingivalis, Leptospira interrogans*), GPI-anchor proteins (*Trypanosoma cruzi*), neisserial porins, hemagglutinin (MV), phospholipomannan (*Candida*), LAM (Mycobacteria), ssRNA virus (WNV), dsRNA virus (RSV, MCMV), LPS (Gram-negative bacteria), F-protein (RSV), mannan (*Candida*), glycoinositolphospholipids (*Trypanosoma*), envelope proteins (RSV and MMTV), flagellin (Flagellated bacteria), phenol-soluble modulin (*Staphylococcus epidermidis*), diacylated lipopeptides (*Mycoplasma*), LTA (*Streptococcus*), zymosan (*Saccharomyces*), viral ssRNA (Influenza, VSV, HIV, HCV), ssRNA from RNA virus, dsDNA viruses (HSV, MCMV), hemozoin (*Plasmodium*), and unmethylated CpG DNA (bacteria and viruses). In one embodiment, the TLR agonist is a synthetic ligand selected from the group consisting of Pam3Cys, CFA, MALP2, Pam2Cys, FSL-1, Hib-OMPC, Poly I:C; poly A:U, AGP, MPL A, RC-529, MDF2P, CFA, flagellin, MALP-2, Pam2Cys, FSL-1, Guanosine analogs, imidazoquinolines (e.g. Imiquimod, Aldara® R848, Esiquimod®), loxoribine, imidazoquinolines, Loxoribine, ssPolyU, 3M-012, and CpG-oligonucleotides.

In some embodiments, the adjuvant comprises granulocyte-macrophage colony-stimulating factor (GM-CSF). Granulocyte-macrophage colony-stimulating factor (GM-CSF) is a protein secreted by macrophages, T cells, mast cells, endothelial cells and fibroblasts. Specifically, GM-CSF is a cytokine that functions as a white blood cell growth factor. GM-CSF stimulates stem cells to produce granulocytes and monocytes. Monocytes exit the blood stream, migrate into tissue, and subsequently mature into macrophages. GM-CSF also has the ability to recruit and program antigen-presenting cells.

GM-CSF polypeptides can be isolated from endogenous sources or synthesized in vivo or in vitro. Endogenous GM-CSF polypeptides are isolated from healthy human tissue. Synthetic GM-CSF polypeptides are synthesized following transfection or transformation of template DNA into a host organism or cell, e.g., a mammal or cultured human cell line. Alternatively, synthetic GM-CSF polypeptides are synthesized by polymerase chain reaction (PCR) or other well-known methods in the art (Sambrook, J., et al., *Molecular Cloning: A Laboratory Manual*. Cold Spring Harbor Laboratory Press, NY, Vol. 1, 2, 3 (1989), the entire contents of the foregoing publication is incorporated herein by reference).

GM-CSF polypeptides are modified to increase protein stability in vivo. Alternatively, GM-CSF polypeptides are engineered to be more or less immunogenic. GM-CSF polypeptides are recombinant. Alternatively, GM-CSF polypeptides are humanized derivatives of mammalian GM-CSF polypeptides. Exemplary mammalian species from which GM-CSF polypeptides are derived include, but are not limited to, mouse, rat, hamster, guinea pig, goat, bird, cat, dog, monkey, or primate. In some embodiments, GM-CSF is a recombinant human protein (PeproTech, Catalog #300-03). In other embodiments, GM-CSF is a recombinant murine (mouse) protein (PeproTech, Catalog #315-03). In yet another embodiment, GM-CSF is a humanized derivative of a recombinant mouse protein.

In some embodiments, the adjuvant comprises cytosine-Guanosine (CpG) Oligonucleotide (CpG-ODN) sequences, e.g., the adjuvant comprises CpG dinucleotides or CpG oligonucleotides. CpG sites are regions of deoxyribonucleic acid where a cysteine nucleotide occurs next to a guanine nucleotide in the linear sequence of bases along its length (the "p" represents the phosphate linkage between them and distinguishes them from a cytosine-guanine complementary base pairing). CpG sites play a pivotal role in DNA methylation, which is one of several endogenous mechanisms cells use to silence gene expression. Methylation of CpG sites within promoter elements can lead to gene silencing. CpG-ODN sequences found in bacterial DNA are potent immunomodulators that stimulate activation of an antigen presenting cell, for example, dendritic cell, leading to specific T-cell responses.

CpG oligonucleotides for use in the vaccine compositions of the present invention can be isolated from endogenous sources or synthesized in vivo or in vitro. Exemplary sources of endogenous CpG oligonucleotides include, but are not limited to, microorganisms, bacteria, fungi, protozoa, viruses, molds, or parasites. Synthetic CpG oligonucleotides are synthesized following transfection or transformation of template DNA into a host organism. Alternatively, Synthetic CpG oligonucleotides are synthesized by polymerase chain reaction (PCR) or other well-known methods in the art.

CpG oligonucleotides are presented for cellular uptake by dendritic cells. In one embodiment, naked CpG oligonucleotides are used in the vaccine compositions of the invention. The term "naked" is used to describe an isolated endogenous or synthetic polynucleotide (or oligonucleotide) that is free of additional substituents. In another embodiment, CpG oligonucleotides are bound to one or more compounds to increase the efficiency of cellular uptake. Alternatively, or in addition, CpG oligonucleotides are bound to one or more compounds to increase the stability of the oligonucleotide within the vaccine composition and/or dendritic cells.

CpG oligonucleotides are condensed prior to cellular uptake. In some embodiments, CpG oligonucleotides are condensed using polyethylimine (PEI), a cationic polymer that increases the efficiency of cellular uptake into dendritic cells. The amine-rick polycation, PEI, condenses plasmid DNA via association with DNA phosphate groups, resulting in small, positively charge condensates facilitating cell membrane association and DNA uptake into cells (Godbey et al., 1999, *Proc Natl Acad Sci USA*, 96(9): 5177-81).

In some embodiments, the bioagents, e.g., adjuvants, are linked to the solid substrate, e.g.,beads. Bioagents can be conjugated to the surface of the solid substrate using any of a variety of methods known to those of skill in the art for conjugating proteins or peptides with other molecules. For example, Hermanson, Bioconjugate Techniques (2nd Ed., Academic Press (2008)) and Niemeyr, *Bioconjugation Protocols: Strategies & Methods*, in Methods In Molecular Biology (Humana Press, 2004), provide a number of methods and techniques for conjugating peptides to other molecules. The bioagents can be coupled or conjugated to the surface of the solid substrate covalently or non-covalently. The covalent linkage between the bioagents and the surface can also be mediated by a linker. The non-covalent linkage between the bioagents and the surface can be based on ionic interactions, van der Waals interactions, dipole-dipole interactions, hydrogen bonds, electrostatic interactions, and/or shape recognition interactions.

The bioagents in the vaccine compositions of the present invention are capable of recruiting and/or activating an immune cell in a subject. An immune cell refers to any cell of the immune system that functions to protect the body against both infectious disease and foreign invaders. Exemplary immune cells include, but are not limited to, a T cell, a B cell, an antigen-presenting cell, a dendritic cell, a macrophage, a granulocytes, a monocyte, a neutrophil, and a natural killer (NK) cell.

In some embodiments, the immune cell is an antigen-presenting cell. Antigen-presenting cells (APCs), also known as accessory cells, are cells that display antigen complexed with major histocompatibility complexes (MHCs) on their surfaces. Antigen-presenting cells process antigens and present them to the T cells of the immune system. Antigen-presenting cells can be found in a variety of tissue types. Classical antigen-presenting cells, including macrophages, B cells, and dendritic cells, associate with an MHC class II molecule to present foreign antigens to helper T cells. While other cell types, e.g., mast cells, basophils, eosinophils, and group 3 innate lymphoid cells (ILC3s), that can express MHC class II molecules, may also serve as antigen-presenting cells (Kambayashi and Laufer, 2014, *Nature Reviews Immunology* 14, 719-730). Antigen-presenting cells may also include any cells, e.g., nucleated cells, that are capable of displaying endogenous peptides on the cell surface to cytotoxic T cells, typically using an MHC class I molecule. In addition to the MHC family of proteins, antigen presentation relies on other specialized signaling molecules on the surfaces of both APCs and T cells.

Antigen-presenting cells are very efficient at internalizing antigens, either by phagocytosis (macrophages and dendritic cells) or by receptor-mediated endocytosis (B cells), processing the antigen into peptide fragments and then displaying those peptides, bound to a class II MHC molecule, on their membrane. T cells recognize and interact with the antigen-class II MHC molecule complex on the membrane of the antigen-presenting cell. An additional co-stimulatory signal is then produced by the antigen-presenting cell, leading to activation of the T cell. The expression of co-stimulatory molecules and MHC class II are defining features of professional APCs.

Antigen-presenting cells (APCs) are vital for effective adaptive immune response because the functioning of both cytotoxic and helper T cells is dependent on APCs. Antigen presentation allows for specificity of adaptive immunity and can contribute to immune responses against both intracellular and extracellular pathogens.

The vaccine compositions of the present invention may further comprise a scaffold comprising a biomaterial and capable of recruiting and activating an immune cell in a subject. Thus, the present invention also provides vaccine compositions comprising a scaffold comprising a biomaterial and capable of recruiting and activating an immune cell in a subject; and an opsonin-bound or lectin-bound pathogen construct. The scaffold provides a physical structure upon which or into which the opsonin-bound or lectin-bound pathogen construct or the bioagent can associate or attach. The opsonin-bound or lectin-bound pathogen construct can be encapsulated within the scaffold for delivery or administration to a subject, therefore preventing any undesired leakage of pathogen from the vaccine composition. In some embodiments, the vaccine compositions further comprise one or more bioagents as described herein. The bioagent is capable of recruiting and/or activating an immune cell in a subject. In some embodiments, the vaccine compositions comprise granulocyte macrophage colony stimulating factor (GM-CSF). In other embodiments, the vaccine compositions comprise a cytosine-guanosine oligonucleotide (CpG-ODN) sequence. In yet another embodiment, the vaccine compositions comprise the combination of granulocyte macrophage colony stimulating factor (GM-CSF) and cytosine-guanosine oligonucleotide (CpG-ODN) sequence.

The scaffolds comprise a biocompatible material that is not toxic or immunogenic. As used herein, the term "biocompatible material" refers to any material that does not deteriorate appreciably and does not induce a significant immune response or deleterious tissue reaction, e.g., toxic reaction or significant irritation, over time when implanted into or placed adjacent to the biological tissue of a subject, or that does not induce blood clotting or coagulation when it comes in contact with blood.

The scaffolds can be biodegradable in the body. In some embodiments, the scaffold composition degrades at a predetermined rate based on a physical parameter selected from the group consisting of temperature, pH, hydration status, and porosity, the cross-link density, type, and chemistry or the susceptibility of main chain linkages to degradation or it degrades at a predetermined rate based on a ratio of chemical polymers. For example, a high molecular weight polymer comprised of solely lactide degrades over a period of years, e.g., 1-2 years, while a low molecular weight polymer comprised of a 50:50 mixture of lactide and glycolide degrades in a matter of weeks, e.g., 1, 2, 3, 4, 6, 10 weeks. A calcium cross-linked gels composed of high molecular weight, high guluronic acid alginate degrade over several months (1, 2, 4, 6, 8, 10, 12 months) to years (1, 2, 5 years) in vivo, while a gel comprised of low molecular weight alginate, and/or alginate that has been partially oxidized, will degrade in a matter of weeks.

Exemplary biomaterials suitable for use as scaffolds in the present invention include glycosaminoglycan, silk, fibrin, MATRIGEL®, poly-ethyleneglycol (PEG), polyhydroxy ethyl methacrylate, polyacrylamide, poly (N-vinyl pyrolidone), (PGA), poly lactic-co-glycolic acid (PLGA), poly e-carpolactone (PCL), polyethylene oxide, poly propylene fumarate (PPF), poly acrylic acid (PAA), polyhydroxybutyric acid, hydrolysed polyacrylonitrile, polymethacrylic acid, polyethylene amine, esters of alginic acid; pectinic acid; and alginate, fully or partially oxidized alginate, hyaluronic acid, carboxy methyl cellulose, heparin, heparin sulfate, chitosan, carboxymethyl chitosan, chitin, pullulan, gellan, xanthan, collagen, gelatin, carboxymethyl starch, carboxymethyl dextran, chondroitin sulfate, cationic guar, cationic starch, and combinations thereof. In certain embodiments, the biomaterial is selected from the group consisting of poly(L-lactide-co-glycolide) acid (PLGA), mesoporous silica, cryogel, and combinations thereof.

In some embodiments, the scaffold comprises a macroporous poly-lactide-co-glycolide (PLG). Vaccine compositions comprising PLG scaffolds are capable of releasing the encapsulated composition, e.g., an opsonin-bound or lectin-bound pathogen construct, or a bioagent, from the scaffolds, gradually over the period of time, for example, over the next days or weeks, after administration to the target site in or on the subject. The rate of releasing the encapsulated pathogen from the scaffolds can therefore by regulated in a temporal manner. As a result, the immune responses elicited by the pathogen in the vaccine compositions can also be controlled temporally.

In some embodiments, the scaffolds comprise mesoporous silica (MPS). In other embodiments, the scaffolds comprise cryogels. See, e.g., International Patent Publication No. WO 2012/149358A1. The entire contents of the foregoing patent application are incorporated herein by reference.

In some embodiments, the scaffolds comprise a non-biodegradable material or are resistant to breakdown in the body. Relatively permanent (degradation resistant) scaffold compositions include metals and some polymers such as silk and plastic.

In some embodiments, the scaffolds, e.g., hydrogels, comprise biomaterials that are modified, e.g., sites on the biomaterial are modified with a functional group, e.g., a methacrylic acid group (methacrylate (MA)) or an acrylic acid group (acrylate). The degree of methacrylation can be varied from 1% to 90%. Above 90%, the chemical modification may reduce solubility of the polymer water-solubility. Exemplary modified hydrogels are MA-alginate (methacrylated alginate) or MA-gelatin. In the case of MA-alginate or MA-gelatin, 50% corresponds to the degree of methacrylation of alginate or gelatin. This means that every other repeat unit contains a methacrylated group.

Biomaterials for use in the scaffolds of the present invention can also be modified with acrylated groups instead of methacrylated groups. The product would then be referred to as an acrylated-polymer. The degree of methacrylation (or acrylation) can be varied for most polymers. Further, alginate or gelatin may be modified with click moieties to produce click-alginate or click-gelatin cryogels (see, e.g., International Patent Application Publication No. WO2015154078, the entire contents of the foregoing patent application are incorporated herein by reference), In addition, click alginate may be oxidized and further proceeded using either ammonia borane or sodium chlorite to elimination aldehydes prior to click conjugation to produce a biodegradable click alginate cryogel (see, e.g., International Patent Application No. PCT/US16/058866, the entire contents of the foregoing patent application are incorporated herein by reference), The scaffolds of the present invention may comprise an external surface. Alternatively, or in addition, the scaffolds may comprise an internal surface. External or internal surfaces of the scaffolds of the present invention may be solid or porous. Pore size of the scaffolds can be less than about 10 nm, between about 100 nm-20 µm, or greater than about 20 µm, e.g., up to and including 1000 µm in diameter. For example, the pores may be nanoporous, microporous, or macroporous. For example, the diameter of nanopores are less than about 10 nm; micropore are in the range of about 100 µm-20 µm in diameter; and, macropores are greater than about 20 µm, e.g., greater than about 100 µm, e.g., greater than about 400 µm, e.g., greater than 600 µm or greater than 800 µm.

In some embodiments, the scaffolds of the present invention are organized in a variety of geometric shapes (e.g., discs, beads, pellets), niches, planar layers (e.g., thin sheets). For example, discs of about 0.1-200 millimeters in diameter, e.g., 5, 10, 20, 40, 50 millimeters may be implanted subcutaneously. The disc may have a thickness of 0.1 to 10 millimeters, e.g., 1, 2, 5 millimeters. The discs are readily compressed or lyophilized for administration to a patient. An exemplary disc for subcutaneous administration has the following dimensions: 8 millimeters in diameter and 1 millimeter in thickness. In some embodiments, the scaffolds may comprise multiple components. Multicomponent scaffolds are optionally constructed in concentric layers each of which is characterized by different physical qualities such as the percentage of polymer, the percentage of crosslinking of polymer, chemical composition of the hydrogel, pore size, porosity, and pore architecture, stiffness, toughness, ductility, viscoelasticity, and/or pharmaceutical composition.

In some embodiments, the scaffold further comprises one or more bioagents as described herein. In some embodiments, the bioagent is covalently linked to the scaffold or the solid structure, e.g., beads, within the scaffold, keeping the bioagent relatively immobilized in or on the scaffold or the solid structure, e.g., beads, within the scaffold. In other embodiments, the bioagent is non-covalently associated with the scaffold. Non-covalent bonds include electrostatic, hydrogen, vander Waals, and hydrophobic interaction. In some embodiments, the scaffold comprises granulocyte macrophage colony stimulating factor (GM-CSF). In other embodiments, the scaffold comprises cytosine-guanosine oligonucleotide (CpG-ODN) sequences. In certain embodiments, the scaffold comprises both GM-CSF and CpG-ODN.

The bioagents are added to the scaffold using known methods in the art including surface absorption, physical immobilization, e.g., using a phase change to entrap the substance in the scaffold material. For example, a bioagent, e.g., a growth factor, is mixed with the scaffold while it is in an aqueous or liquid phase, and after a change in environmental conditions (e.g., pH, temperature, ion concentration), the liquid gels or solidifies thereby entrapping the bioagent. Alternatively, covalent coupling, e.g., using alkylating or acylating agents, is used to provide a stable, long term presentation of a bioagent on the scaffold in a defined conformation. Exemplary reagents for covalent coupling of such substances are provided in the table below. Approaches to coupling of bioagents, e.g., proteins or peptides, to scaffold polymers are discussed in Hirano and Mooney, 2005, *Advanced Materials,* 16(1): 17-25. Other useful bonding chemistries also include those discussed in Hermanson, 1996, *Bioconjugate Techniques,* 152-185.

| Methods to covalently couple peptides/proteins to polymers | | |
|---|---|---|
| Functional Group of Polymer | Coupling reagents and cross-linker | Reacting groups on proteins/peptides |
| —OH | Cyanogen bromide (CNBr) Cyanuric chloride 4-(4,6-Dimethoxy-1,3,5-triazin-2-yl)-4-methyl-morpholinium chloride (DMT-MM) | —$NH_2$ |
| —$NH_2$ | Diisocyanate compounds Diisothoncyanate compounds Glutaraldehyde Succinic anhydride | —$NH_2$ —OH |
| —$NH_2$ | Nitrous Acid Hydrazine + nitrous acid | —$NH_2$ —SH —Ph—OH |
| —$NH_2$ | Carbodiimide compounds (e.g., EDC, DCC)[a] DMT-MM | —COOH |
| Azide | Copper catalyst | -alkyne |
| Azide | None | -DBCO or Cycooctyne |
| Tetrazine | None | -TCO |
| —$NH_2$ | Sortase enzyme | Peptide |
| —O—$NH_2$ | Pyridoxamine | N-terminus |
| —COOH | Thionyl chloride N-hydroxysuccinimide N-hydroxysulfosuccinimide + EDC | —$NH_2$ |
| —SH | Disulfide compound | —SH |
| Maleimide | None | —SH |
| iodoacetate | None | SH |

[a]EDC: 1-ethyl-3-(3-dimethylaminopropyl) carbodiimide hydrochloride; DCC: dicyclohexylcarbodiimide The scaffolds are assembled using methods known in the art, e.g., injection molding, lyophilization of preformed structures, printing, self-assembly, phase inversion, solvent casting, melt processing, gas foaming, fiber forming/processing, particulate leaching or a combination thereof. The assembled scaffolds are then used to prepare the vaccine compositions of the present invention.

In some embodiments, the scaffolds are suitable for implantation. For example, the scaffolds are prepared using poly-lactide-co-glycolide (PLG). The vaccine compositions comprising the PLG scaffolds, if implanted, can be easily removed from the subject after vaccination. For example, in the case where too much immune response or undesired side effects are initiated after vaccination, the implanted vaccine compositions can be removed from the subject. In some embodiments, the scaffolds are suitable for injection. For example, the scaffolds are created outside of the body as macroporous scaffolds. The scaffold can be injected into the body because the pores collapse and the gel becomes very small and can fit through a needle. See, e.g., WO 12/149358; and Bencherif et al. *Proc. Natl. Acad. Sci. USA* 109.48 (2012):19590-5. The entire contents of each of the foregoing references are incorporated herein by reference.

The vaccine compositions of the present invention may comprise one type of pathogen, or they may comprise multiple types of pathogens, e.g., at least 2, 3, 4, 5, 6, 7, 8, 9, 10, 11, 12, 13, 14, 15, 20, 25, 30, 35, 40, 45, 50 or more types of pathogens. The vaccine compositions may also contain one or more types of adjuvants that program the immune cells to recognize antigen and enhance antigen presentation as described herein.

The vaccine compositions of the present invention may be systemically administered, e.g., enterally administered (e.g., orally, buccally, sublingually, or rectally) or parenterally administered (e.g., intravenously, intra-arterially, intraosseously, intra-muscularly, intracerebrally, intracerebroventricularly, intrathecally, or subcutaneously). Other suitable modes of administration of the vaccine compositions of the invention include hypodermal, intraperitoneal, intraocular, intranasal, transdermal (e.g., via a skin patch), epidural, intracranial, percutaneous, intravaginal, intrauterineal, intravitreal, or transmucosal administration, or administration via injection, or via implantation.

As shown in the Examples, in accordance to the vaccine compositions described herein, subcutaneous implantation or injection of the vaccine compositions in mice successfully protected the mice from a lethal dose of bacterial infection. Specifically, mice immunized with the vaccine compositions of the present invention exhibited a significantly prolonged survival time and a significantly reduced titer of pathogen in various organs when compared with the control mice. Accordingly, in some embodiments, the vaccine composition is suitable for implantation, e.g., subcutaneous implantation. In some embodiments, the vaccine composition is suitable for injection in a subject. In certain embodiments, the vaccine composition is suitable for oral administration in a subject. For example, the vaccine composition can be in the form of a pill, a tablet, a capsule, a soft gel, a chewable, a powder, an emulsion, or an aqueous solution for oral administration.

The vaccine compositions of the present invention possess a distinct advantage over existing vaccines in that only one single administration is sufficient to elicit a sustained immune response, e.g., a antibody-mediated and/or cell-mediated immune response, against targeted pathogens. Indeed, as shown in Example 1, a single dose of the vaccine composition of the invention can protect the vaccinated mice from bacteria challenge over a period of at least 90 days.

In addition, the vaccine compostions confer another significant advantage over available vaccines in the art in that they can be easily removed from a subject after implantation. For example, if too much immune response or undesired side effects are initiated after the subject receives the vaccine compositions, the vaccine compositions, e.g., PLG scaffold vaccine compositoons, can be readily removed from the subject. In contract, current existing vaccines cannot be removed once they are injected in the subjects.

The vaccine compositions of the present invention are highly stable and capable of being portable and being stored at room temperature without the need for refrigeration. Upon lyophilization, the vaccine compositions may have a shelf life of about 1 day to about 1 year, e.g., about 10 days to about 1 year, about 30 days, to about 1 year, about 2 months to about 1 year, about 3 months to about 1 year, about 4 months to about 1 year, about 5 months to about 1 year, about 6 months to about 1 year, about 7 months to about 1 year, about 8 months to about 1 year, about 9 months to about 1 year, about 10 months to about 1 year. In some embodiments, the vaccine composition has a shelf life of at least 1 year, e.g., 1, 2, 3, 4, 5, 6, 7, 8, 9, or 10 years.

The vaccine compositions of the present invention allow the rapid and direct isolation of pathogens circulating in a blood sample from a patient with infectious disease including both known and unknown pathogens, pathogens present within other biological fluids, or pathogens present in an in vitro culture, and hence greatly increase the immune response as compared to conventional antibiotic therapies. The claimed vaccine compositions can also be used against pathogens that are difficult to isolate and purify. The vaccine compositions of the present invention also possess additional improvements over existing vaccines. For example, vaccination using the claimed vaccine compositions can occur in a more controlled, localized and safer manner, without compromising the efficacy of the vaccine compositions. The improved stability of the claimed vaccines allows them to be portable and to be used for long term storage at room temperature without the need of refrigeration. Furthermore, the vaccine compositions can be multivalent vaccines when more than one type of pathogens are included in the compositions, and can also be used to vaccinate against different species or strains of a given pathogen. These improvements circumvent the major limitations of current pathogen vaccines, and would be of great interest to the public, especially during the time of an epidemic, for example, for populations in developing countries, or of great value for military uses, where vaccines that are readily available are highly desired. For example, pathogens can be isolated directly and rapidly using an engineered lectin, e.g., the engineered MBL, from a subject, e.g., a human, having or at risk of having an infectious disease, neutralized by antibiotics treatment, incorporated into a scaffold composition, e.g., a PLG scaffold, and then administered back to the same human subject, or a different human subject, for treating infectious disease. Alternatively, the vaccine composition can be lyophilized and stored at room temperature for about 1 day to about 1 year, and then administered to a subject to induce an immune response against the pathogen or pathogen fragment within the vaccine compositions, thereby treating the infectious disease. This is extremely beneficial especially in the case where ring vaccination is highly desired to treat infectious diseases or prevent the spread of infectious pathogens. The vaccine compositions of the present invention can be made readily available and then administered to infected individuals or any other individuals that come in contact with the infected group or are at risk of being infected.

The present invention also provides stable scaffold compositions. The stable scaffold compositions comprise a biomaterial and capable of recruiting and activating an immune cell in a subject, wherein the scaffold is lyophilized, and wherein the scaffold has a shelf life of about 30 days to about 1 year.

In another aspect, the present invention provides stable opsonin-bound or lectin-bound pathogen constructs. The opsonin-bound or lectin-bound pathogen constructs comprise a pathogen or fragment thereof derived from a subject bound to an opsonin or a lectin, wherein the opsonin-bound or lectin-bound pathogen construct is lyophilized, and wherein the opsonin-bound or lectin-bound pathogen construct has a shelf life of about 30 days to about 1 year.

In yet another aspect, the prevent invention provides scaffold compositions. The scaffold compositions comprise a biomaterial and are capable of recruiting and activating an immune cell in a subject, wherein the scaffold comprises a solid substrate, e.g., beads, e.g., magnetic beads, and wherein the solid substrate is suitable for attachment of a pathogen. The scaffold compositions of the invention are stable and can be readily available, for example, during a war or during a pandemic. Any pathogen or pathogen fragment that is capable of inducing an infectious disease in a subject, as described herein, may be introduced in the scaffold compositions of the invention in order to generate vaccine compositions. Pathogens or pathogen fragments can be introduced into the scaffold compositions of the invention once they are isolated, for example, from a sample of a subject, e.g., a human, or from an in vitro culture, then incorporated into the scaffold composition, and then administered to a subject for treating infectious disease. These scaffold compositions are very useful and highly desirable, for example, during the time of an epidemic, or of great value for military uses, where vaccines that are readily available are highly desired.

III. Formulations

The vaccine compositions of the present invention can be used directly for purposes of treatment and prophylaxis of various diseases, e.g., infectious diseases. The vaccine compositions of the invention can be formulated using one or more physiologically acceptable carriers or excipients. For example, where a composition is formulated as a liquid, it may comprise sterile saline, a dextrose solution, or a buffered solution, or other pharmaceutically acceptable sterile fluid. In some embodiments, the formulations are for intradermal or subcutaneous administration. In some embodiments, the formulations are for inhalation or insufflation (either through the mouth or the nose). In some embodiments, the formulations are for oral, buccal, parenteral, vaginal, or rectal administration. The term parenteral as used herein includes subcutaneous, intracutaneous, intravenous, intramuscular, intra-articular, intraarterial, intrasynovial, intrasternal, intrathecal, intralesional and intracranial injection or infusion techniques. In some embodiments, the formulations are for implantation.

Preferably, the vaccine compositions are formulated to provide increased chemical stability of the opsonin-bound or lectin-bound pathogen construct or the bioagent during storage and transportation. For example, in one embodiment, the formulation prevents or reduces protein oligomerization or aggregation. In another example, the formulation prevents or reduces oxidation of the amino acid residues. The formulations may be lyophilized or liquid formulations. Lyophilized formulations have a shelf life of about 1 day to about 1 year, e.g., about 10 days to about 1 year, about 30 days, to about 1 year, about 2 months to about 1 year, about 3 months to about 1 year, about 4 months to about 1 year, about 5 months to about 1 year, about 6 months to about 1 year, about 7 months to about 1 year, about 8 months to about 1 year, about 9 months to about 1 year, about 10 months to about 1 year. In some embodiments, the formulation has a shelf life of at least 1 year, e.g., 1, 2, 3, 4, 5, 6, 7, 8, 9, or 10 years.

In some embodiments, the vaccine compositions are formulated for injection. In certain embodiments, the vaccine compositions are sterile lyophilized formulations, substantially free of contaminating cellular material, chemicals, virus, or toxins. In a particular embodiment, formulations for injection are provided in sterile single dosage containers. The formulations may or may not contain an added preservative. Liquid formulations may take such forms as suspensions, solutions or emulsions in oily or aqueous vehicles, and may contain formulatory agents such as suspending, stabilizing and/or dispersing agents.

In one embodiment, the formulation comprises liposomes. In one embodiment, a vaccine composition of the invention is formulated with one or more other therapeutic agents used for the treatment of infectious diseases.

The vaccine compositions of the invention may be formulated as pharmaceutical compositions and can include one or more pharmaceutically acceptable carriers, additives, or vehicles. In one embodiment, the one or more pharmaceutically acceptable carriers, additives, or vehicles is selected from the group consisting of ion exchangers, alumina, aluminum stearate, lecithin, self-emulsifying drug delivery systems (SEDDS) such as d-I-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins may also be advantageously used to enhance delivery of compounds of the formulae described herein. The vaccine compositions of the invention may also comprise a pharmaceutically acceptable acid, base or buffer to enhance the stability of the formulated compound or its delivery form.

In some embodiments, the vaccine compositions of the invention are in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives, are useful in the preparation of injectables. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

In some embodiments, the vaccine compositions of the invention are in the form of an orally acceptable dosage form including, but not limited to, solid drugs such as pills, tablets, granules, soft gels, chewable, powders, and capsules; liquid drugs such as emulsions and aqueous suspensions, dispersions and solutions; inhalants and lyophilized drugs. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added. These drugs can be prepared by conventional pharmaceutical practices.

IV. Methods of the Invention

The vaccine compositions of the present invention are useful for the prophylaxis and treatment of various diseases, e.g., infectious diseases. As shown in the Examples presented herein, immunization of mice with vaccine compositions of the present invention, e.g., a vaccine comprising a lectin-bound pathogen construct with CpG and GM-CSF adjuvants within a PLG or MPS scaffold, successfully protected mice from a lethal dose of bacteria, resulting in a significantly prolonged survival time and a reduced titer of pathogen in various organs in vaccinated mice when compared to controls.

Accordingly, the present invention, in one aspect, provides methods for treating a pathogen infection in a subject in need thereof. The methods comprise administering the vaccine composition as described herein, thereby treating the pathogen infection in the subject.

In another aspect, the present invention provides methods of vaccinating a subject against a pathogen infection. The methods comprise administering the vaccine composition as described herein, thereby vaccinating the subject against the pathogen infection.

The present invention also provides methods of treating an antibiotic-resistant bacterial infection in a subject in need thereof. The methods comprise administering the vaccine composition as described herein, thereby treating the antibiotic-resistant bacterial infection in the subject. In some embodiments, the vaccine composition is specific for the antibiotic-resistant bacterium in the subject.

The present invention further provides methods of decreasing the level of a pathogen in a subject having a pathogen infection. The methods comprise administering the vaccine composition as described herein, thereby decreasing the level of the pathogen in the subject. In some embodiments, the level of the pathogen is decreased in an organ of the subject. In some embodiments, the organ is selected from the group consisting of a lung, a liver, a kidney, and a spleen.

In another aspect, the present invention provides methods of increasing the survival rate of a subject having a pathogen infection. The methods comprise administering the vaccine composition as described herein, thereby increasing the survival rate of the subject.

In one aspect, the present invention provides methods of reducing the level of pain associated with a pathogen infection in a subject in need thereof. The methods comprise administering the vaccine composition as described herein, thereby reducing the level of pain associated with the pathogen infection in the subject.

In another aspect, the present invention provides methods of reducing the level of distress associated with a pathogen infection in a subject in need thereof. The methods comprise administering the vaccine composition as described herein, thereby reducing the level of distress associated with the pathogen infection in the subject.

In some embodiments, the subject suffers from an infectious disease or is at risk of having an infectious disease. Infectious diseases are caused by pathogenic microorganisms, such as bacteria, viruses, parasites or fungi. The diseases can be spread directly or indirectly, from one person to another. Infectious disease can also be transmitted from animals to humans.

Infectious diseases which can be treated prophylactically or therapeutically with the vaccine compositions of the present invention include, but are not limited to, tuberculosis, measles, meningococcal meningitis, *Pseudomonas aeruginosa*, chikungunya, malaria, plaque, HIV/AIDS, pneumonia, rhinoviral diseases, spring-summer meningoencephalitis (SSME), rubella, poliomyelitis, rabies, hepatitis A, hepatitis B, hepatitis C, hepatitis E, buruli ulcer, Ebola virus disease, yellow fever, Dengue's disease, trachoma, Chagas disease, influenza, smallpox, avian influenza, cholera, Mediterranean fever, undulant fever, Malta fever, contagious abortion, epizootic abortion. Bang's disease, Salmonella food poisoning, enteric paratyphosis, Bacillary dysentery, Pseudotuberculosis, plague, pestilential fever, Vibrios, Circling disease, Weil's disease, Hemorrhagic jaundice (*Leptospira icterohaemorrhagiae*), canicola fever (*L. canicola*), dairy worker fever (*L. hardjo*), Relapsing fever, tick-borne relapsing fever, spirochetal fever, vagabond fever, famine fever, Lyme arthritis, Bannworth's syndrome, tick-borne meningopolyneuritis, erythema chronicum migrans, Vibriosis, Colibacteriosis, colitoxe ia, white scours, gut edema of swine, enteric paratyphosis, Staphylococcal alimentary toxicosis, staphylococcal gastroenteritis, Canine Corona Virus (CCV) or canine parvovirus enteritis, feline infectious peritonitis virus, transmissible gastroenteritis (TGE) virus, Hagerman Redmouth Disease (ERMD), Infectious Hematopoietic necrosis (IHN), porcine Actinobacillus (*Haemophilus*) pleuropneumonia, Hansen's disease, Streptotrichosis, Mycotic Dermatitis of Sheep, Pseudoglanders, Whitmore's disease, Francis' disease, deer-fly fever, rabbit fever, O'Hara disease, Streptobacillary fever, Haverhill fever, epidemic arthritic erythema, sodoku, Shipping or transport fever, hemorrhagic septicemia, Ornithosis, Parrot Fever, Chlamydiosis, North American blastomycosis, Chicago disease, Gilchrist's disease, Cat Scratch Fever, Benign Lymphoreticulosis, Benign nonbacterial Lymphadenitis, Bacillary Angiomatosis, Bacillary Peliosis Hepatis, Query fever, Balkan influenza, Balkan grippe, abattoir fever, Tick-borne fever, pneumorickettsiosis, American Tick Typhus, Tick-borne Typhus Fever, Vesicular Rickettsiosis, Kew Gardens Spotted Fever, Flea-borne Typhus Fever, Endemic Typhus Fever, Urban Typhus, Ringworm, Dermatophytosis, Tinea, Trichophytosis, Microsporosis, Jock Itch, Athlete's Foot, Sporothrix schenckii, dimorphic fungus, Cryptococcosis and histoplasmosis, Benign Epidermal Monkeypox, BEMP, Herpesvirus simiae, Simian B Disease, Type C lethargic encephalitis, Yellow fever, Black Vomit, hantavirus pulmonary syndrome, Korean Hemorrhagic Fever, Nephropathia Epidemica, Epidemic Hemorrhagic Fever, Hemorrhagic Nephrosonephritis, lymphocytic choriomeningitis, California encephalitis/La cros se encephalitis, African Hemorrhagic Fever, Green or Vervet Monkey Disease, Hydrophobia, Lyssa, Infectious hepatitis, Epidemic hepatitis, Epidemic jaundice, Rubeola, Morbilli, Swine and Equine Influenza, Fowl Plague, Newcastle disease, Piroplasmosis, toxoplasmosis, African Sleeping Sickness, Gambian Trypanosomiasis, Rhodesian Trypanosomiasis, Chagas's Disease, Chagas-Mazza Disease, South American Trypanosomiasis, Entamoeba histolytica, Balantidial dysentery, cryptosporidiosis, giardiasis, Microsporidiosis, Anisakiasis, Trichinosis, Angiostrongylosis, eosinophilic meningitis or meningoencephalitis (*A. cantonensis*), abdominal angiostrongylosis (*A. costaricensis*), Uncinariasis, Necatoriasis, Hookworm Disease, Capillariasis, Brugiasis, Toxocariasis, Oesophagostomiasis, Strongyloidiasis, Trichostrongylosis, Ascaridiasis, Diphyllobothriasis, Sparganosis, Hydatidosis, Hydatid Disease, Echinococcus granulosis, Cystic hydatid disease, Tapeworm Infection, Schistosoma and the like.

Malignant diseases caused by infectious pathogens may also be treated using the vaccine compositions of the invention. Examples of such diseases include, but are not limited to, Burkitt lymphoma caused by EBV, Rous sarcoma caused by Rous retrovirus, Kaposi' sarcoma caused by herpes virus type 8, adult T-cell leukemia caused by HTLV-I retrovirus, or hairy cell leukemia caused by HTLV-JJ, and many other tumors and leukemias caused by infectious agents and viruses.

In addition, diseases which are caused by an unknown pathogen, especially malignant or immunological diseases may be treated or prevented using the vaccine compositions of the invention. Non-limiting examples of these diseases comprise leukemias like acute leukemia, acute lymphocytic leukemia, acute myelocytic leukemias like myeloblastic, promyelocytic, myelomonocytic, monocytic, erythroleukemia, chronic leukemia like chronic myelocytic or granulocytic leukemia, chronic lymphocytic leukemia, polycythemia vera, Sezary cell leukemia, lymphoma, Hodgkin's disease, non-Hodgkin's disease, multiple myeloma, Waldenstrom's macroglobulinemia, heavy chain disease, solid tumors like sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, Kaposi's sarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, mycosis fungoides, or pagetoid reticulosis.

In some embodiments, the infectious diseases treatable by the methods of the present invention are chronic infectious diseases. In some embodiments, the infectious diseases treatable by the methods of the present invention are acute infectious diseases.

The methods of the present invention may include administering the vaccine compositions separately or as part of a therapeutic regimen or combination therapy. The terms "administer," "administering," or "administration," as used herein refer to implanting, absorbing, ingesting, injecting, or inhaling, the vaccine composition of the present invention, regardless of form. In some embodiments, a single administration of the vaccine composition of the invention is sufficient for methods as described herein. A single dose of the vaccine composition of the invention can result in a sustained immune response, e.g., antibody-mediated and/or cell-mediated immune response, against the infected pathogen. In other embodiments, the vaccine compositions may be administered in multiple administration, for example, in a prime-boost strategy. In some embodiment, the same vaccines given in the earlier priming immunizations are used for subsequent boost immunizations. In other embodiments, prime-boost can be done with different types of vaccines containing the same antigens. In some embodiments, a vaccine composition of the invention is administered at time zero and a second vaccine composition of the invention is administered following a period of time, for example from 10 to 30 days, from 10 to 60 days, or from 10 to 100 days.

Currently developed vaccines usually require multiple immunizations for vaccines to be successful. For a pediatric population, up to five immunizations may be needed, as is the case for Diphtheria, Tetanus and Pertussis (DTP) vaccine, which is given three times during the first six months after birth, followed by a fourth dose in the second year of life, and a final boost between four and six years of age. Still, some of the vaccines need additional boosts even in adults who have already received the complete immunization series, for example, the Tetanus-diphtheria (Td) vaccine, for which a boost is recommended every 10 years throughout a person's lifespan. It is well accepted that multiple immunizations (i.e. "prime-boost") are critical for even the most successful vaccines. This principle applies to live attenuated vaccines (e.g., oral polio vaccine), inactivated vaccines (e.g., hepatitis A vaccine), recombinant protein subunit vaccines (e.g., hepatitis B vaccine) and polysaccharide vaccines (e.g., *Haemophilus* Influenzae type b vaccine). However, the vaccine compositions of the present invention possess a distinct advantage over existing vaccines in that only one single administration is sufficient for the methods described herein. Indeed, as shown in Example 1, a single dose of the vaccine composition of the invention successfully confers a long-term immune response and protect the vaccinated mice from bacteria challenge over a period of 90 days.

In some embodiments, one or a plurality of vaccine compositions of the invention is administered to the subject at one or multiple sites. Preferably, each site drains to a lymph node or group of lymph nodes. In some embodiments, the sites are selected from the group consisting of the right arm, the left arm, the right thigh, the left thigh, the right shoulder, the left shoulder, the right breast, the left breast, the abdomen, the right buttock, and the left buttock. In some embodiments, the site is or drains to a non-encapsulated cluster of lymphoid tissue selected from the group consisting of the tonsils, the adenoids, the appendix, and Peyer's patches. In some embodiments, a vaccine composition of the invention is administered to a site that drains to the spleen.

Any suitable route of administration is encompassed by the methods of the invention, e.g. intradermal, subcutaneous, intravenous, intramuscular, or mucosal. Mucosal routes of administration include, but are not limited to, oral, rectal, vaginal, and nasal administration. In some embodiments, the vaccine composition is administered transdermally, intradermally, subcutaneously, orally, rectally, vaginally or by inhalation. In other embodiments, the vaccine composition is implanted into a subject.

Where the vaccine composition is in the form of a scaffold, the method of vaccinating a subject comprises injecting or implanting the scaffold composition in the subject, preferably subcutaneous implantation. In certain embodiments, the method of vaccinating a subject may comprise implanting or injecting the scaffold vaccine composition in one or more areas of the subject's anatomy.

The methods disclosed herein can be applied to a wide range of subjects. In some embodiments, the subject is a mammal, e.g., a human, an embryo, a horse, a dog, a cat, a cow, a sheep, a pig, a fish, an amphibian, a reptile, a goat, a bird, a monkey, a mouse, a rabbit, and a rat. In other embodiments, the subject is a human. In certain embodiments, the subject is an embryo.

The terms "treat" or "treating," as used herein, refer to partially or completely alleviating, inhibiting, ameliorating, and/or relieving the infectious disease or condition from which the subject is suffering. In some instances, treatment can result in the continued absence of the infectious disease or condition from which the subject is suffering such as pain or distress.

In some instances, treatments methods can include a single administration, multiple administrations, and repeating administration as required for the prophylaxis or treatment of the infectious disease or condition from which the subject is suffering. In some instances treatment methods can include assessing a level of disease in the subject prior to treatment, during treatment, and/or after treatment. In some instances, treatment can continue until a decrease in the level of disease in the subject is detected.

The methods herein include administration of an effective amount of vaccine compositions to achieve the desired or stated effect, e.g., eliminating infectious pathogens from a subject, thereby treating infectious diseases. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Following administration, the subject can be evaluated to detect, assess, or determine the level of infectious disease. In some instances, treatment can continue until a change, e.g., reduction, in the level of infectious disease in the subject is detected.

Upon improvement of a patient's condition, e.g., a change, e.g., decrease, in the level of disease in the subject, a maintenance dose of a vaccine composition of the present invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

In some embodiments, an effective amount of a vaccine composition of the invention is the amount sufficient to reduce the severity of an infectious disease or condition in a subject having an infectious disease or condition, or the amount sufficient to reduce or ameliorate the severity of one or more symptoms thereof, or the amount sufficient to prevent the progression of the infectious disease or condition, or the amount sufficient to enhance or improve the therapeutic effect(s) of another therapy or therapeutic agent administered concurrently with, before, or after a vaccine composition of the invention.

Symptoms of infectious diseases are well-known to those of skill in the art. Exemplary signs and symptoms of infectious diseases include, but are not limited to, fever, diarrhea, fatigue, muscle aches, coughing, running nose, red and watery eyes, pain, distress, loss of appetite, nausea, abdominal discomfort, weakness, weight loss, and rash.

In some embodiments, the effective amount of a vaccine composition of the invention is the amount sufficient to produce an antibody secreting B cell or cytotoxic T cell mediated immune response directed against one or more of the pathogen or pathogen fragments of the vaccine compositions of the invention. The ability of the vaccine compositions of the invention to elicit an immune response can be determined using any routine method available to those of skill in the art. In some embodiments, the effective amount of each composition is the amount sufficient to produce a cytotoxic T cell response in the subject as measured, for example, by a mixed lymphocyte T cell assay.

In some embodiments, the effective amount of the vaccine composition administered to the subject, or at a particular site of the subject, is that amount which delivers 1 picogram to 1000 micrograms of the one or more pathogens or pathogen fragments of the composition. In some embodiments, the amount of pathogens or pathogen fragments is about 1 pg to about 1000 µg. In some embodiments, the amount of pathogens or pathogen fragments is 1 µg to 100 µg, 1 µg to 200 µg, 1 µg to 300 µg, 1 µg to 400 µg, 1 µg to 500 µg, 1 µg to 600 µg, 1 µg to 700 µg, 1 µg to 800 µg, or 1 µg to 900 µg. In some embodiments, the amount of pathogens or pathogen fragments is 1 µg to 10 µg, 1 µg to 20 µg, 1 µg to 30 µg, 1 µg to 40 µg, 1 µg to 50 µg, 1 µg to 60 µg, 1 µg to 70 µg, 1 µg to 80 µg, or 1 µg to 90 µg. In some embodiments, the amount of pathogens or pathogen fragments is 1 pg to 100 µg, 1 pg to 90 µg, 1 pg to 80 µg, 1 pg to 70 µg, 1 pg to 60 µg, 1 pg to 50 µg, 1 pg to 40 µg, 1 pg to 30 µg, 1 pg to 20 µg or 1 pg to 10 µg. In other embodiments, the amount of pathogens or pathogen fragments is 10 pg to 1 µg, 20 pg to 1 µg, 30 pg to 1 µg, 40 pg to 1 µg, 50 pg to 1 µg, 60 pg to 1 µg, 70 pg to 1 µg, 80 pg to 1 µg, 90 pg to 1 µg, 100 pg to 1 µg, 1000 pg to 1 µg.

The present invention also provides methods for treating a pathogen infection in a subject in need thereof. The methods comprise administering the scaffold composition and the opsonin-bound or lectin-bound pathogen construct as described herein, thereby treating the pathogen infection in the subject.

In another aspect, the present invention provides methods of vaccinating a subject against a pathogen infection. The methods comprise administering the scaffold composition and the opsonin-bound or lectin-bound pathogen construct as described herein, thereby vaccinating the subject against the pathogen infection.

In one aspect, the present invention provides methods of treating an antibiotic-resistant bacterial infection in a subject in need thereof. The methods comprise administering the scaffold composition and the opsonin-bound or lectin-bound pathogen construct as described herein, thereby treating the antibiotic-resistant bacterial infection in the subject. In some embodiments, the vaccine composition is specific for the antibiotic-resistant bacterium in the subject.

In another aspect, the present invention provides methods of decreasing the level of a pathogen in a subject having a pathogen infection. The methods comprise administering the scaffold composition and the opsonin-bound or lectin-bound pathogen construct as described herein, thereby decreasing the level of the pathogen in the subject. In some embodiments, the level of the pathogen is decreased in an organ of the subject. In some embodiments, the organ is selected from the group consisting of a lung, a liver, a kidney, and a spleen.

In one aspect, the present invention provides methods of increasing the survival rate of a subject having a pathogen infection. The methods comprise administering the scaffold composition and the opsonin-bound or lectin-bound pathogen construct as described herein, thereby increasing the survival rate of the subject.

In another aspect, the present invention provides methods of reducing the level of distress associated with a pathogen infection in a subject in need thereof. The methods comprise administering the scaffold composition and the opsonin-bound or lectin-bound pathogen construct as described herein, thereby reducing the level of distress associated with a pathogen infection in the subject.

In a further aspect, the present invention provides methods of reducing the level of pain associated with a pathogen infection in a subject in need thereof. The methods comprise administering the scaffold composition and the opsonin-bound or lectin-bound pathogen construct as described herein, thereby reducing the level of pain associated with a pathogen infection in the subject.

In some embodiments, the scaffold composition and the opsonin-bound or lectin-bound pathogen construct are administered simultaneously to the subject. In other embodiments, the scaffold composition is administered to the subject separately from, e.g., prior to or after, the opsonin-bound or lectin-bound pathogen construct.

The present invention also provides methods of producing a vaccine. The methods comprise contacting a sample comprising a pathogen or fragment thereof with an opsonin or lectin, wherein the opsonin or lectin is capable of binding to the pathogen or fragment thereof in the sample, thereby forming an opsonin-bound or lectin-bound pathogen construct; isolating the opsonin-bound or lectin-bound pathogen construct from the sample; and combining the opsonin-bound or lectin-bound pathogen construct with a bioagent capable of recruiting an immune cell in a subject, thereby producing the vaccine.

In another aspect, the present invention provides methods of producing a vaccine, comprising contacting a sample comprising a pathogen or fragment thereof with an opsonin or lectin, wherein the opsonin or lectin is capable of binding to a pathogen or fragment thereof in the sample, thereby forming an opsonin-bound or lectin-bound pathogen construct; isolating the opsonin-bound or lectin-bound pathogen construct from the sample; and combining the isolated opsonin-bound or lectin-bound pathogen construct with a scaffold, thereby producing the vaccine.

In yet another aspect, the present invention provides methods of producing a vaccine, comprising administering an opsonin or lectin to a subject, wherein the opsonin or lectin is capable of binding to a pathogen or fragment thereof, from the subject, thereby forming an opsonin-bound or lectin-bound pathogen construct; isolating the opsonin-bound or lectin-bound pathogen construct from the subject; and combining the isolated opsonin-bound or lectin-bound pathogen construct with a scaffold, thereby producing the vaccine.

In some embodiments, the pathogen is derived from a subject in vivo. In other embodiments, the pathogen is derived from an in vitro culture, a microorganism lysate, a crude lysate, or a purified lysate. In certain embodiments, the pathogen is a synthetic pathogen.

In some embodiments, the pathogen comprises a pathogen-associated molecule pattern (PAMP). In some embodiments, the PAMP is selected from the group consisting of a pathogen fragment, a pathogen debris, a pathogen nucleic acid, a pathogen lipoprotein, a pathogen surface glycoprotein, a pathogen membrane component, and a released component from the pathogen.

V. Kits

The invention also provides a kit for vaccinating a subject against a pathogen infection. Such kits can include a composition described herein. Such kits can also facilitate performance of the methods described herein.

In one aspect, the kit comprises the vaccine compositions of the invention and instructions for administering the vaccine compositions to a subject. In some embodiments, the vaccine composition is prepackaged in a sterile container.

In another aspect, the kit comprises a scaffold composition and an opsonin-bound or lectin-bound pathogen construct of the invention, and instructions for administering the scaffold composition and the opsonin-bound or lectin-bound pathogen construct to the subject. In some embodiments, the scaffold composition or the opsonin-bound or lectin-bound pathogen construct are prepackaged in a sterile container. The scaffold composition or the opsonin-bound or lectin-bound pathogen construct can be prepackaged in different sterile containers or in the same sterile container.

The composition in each container may be in the form of a pharmaceutically acceptable solution, e.g., in combination with sterile saline, dextrose solution, or buffered solution, or other pharmaceutically acceptable sterile fluid. Alternatively, the composition may be lyophilized or desiccated. The kit optionally further comprises in a separate container a pharmaceutically acceptable solution (e.g., saline, dextrose solution, etc.), preferably sterile, to reconstitute the composition to form a solution for injection purposes.

The kits of the invention may optionally comprise additional components useful for performing the methods of the invention. The kit may comprise one or more reusable or disposable device(s) for administration (e.g., syringes, needles, dispensing pens), preferably packaged in sterile form, and/or a packaged alcohol pad.

In certain embodiments, kits can be supplied with instructional materials which describe performance of the methods of the invention. Kits may include instructions for administration or delivery of a vaccine composition by a clinician or by the patient. In another embodiment, the kits may include instructions for proper storage and handling of the vaccine compositions.

The present invention is further illustrated by the following examples, which are not intended to be limiting in any way. The entire contents of all references, patents and published patent applications cited throughout this application, as well as the Figures, are hereby incorporated herein by reference.

EXAMPLES

Example 1

Infection Vaccine Study

Preparation of FcMBL Beads

Magnetic FcMBL beads were used to capture pathogens or pathogen fragments, e.g., pathogen associated molecular patterns (PAMPs). Briefly, 1 µM Streptavidin coated superparamagnetic beads (Dynal, Life Technologies) was coupled with FcMBL. FcMBL is an engineered lectin consisting of the carbohydrate recognition domain (CRD) of mannose binding lectin (MBL) fused to the Fc region of human IgG with an engineered amino-oxy biotin site. The FcMBL fusion protein was oriented on the beads using the amino-oxy biotin on the terminal of the Fc region of FcMBL. Other beads have been tested for coupling to FcMBL and used for capture of pathogens or pathogen fragments, for example, 500 nm Ademtech superparamagnetic beads. Direct coupling of FcMBL to the beads without Streptavidin were also tested and shown to work for pathogen capture. Final concentration of beads used for vaccine generation was 5 mg/mL.

Preparation of Pathogen Samples

Pathogen for vaccines can be isolated from any infection. For example, pathogen can be cultured for PAMPs preparation. Alternatively, PAMPs can be captured directly from blood sample. Experiments in the present study were performed using a MDR strain of pathogenic RS218 *E. coli*, isolated from infantile spinal meningitis. RS218 has the serotype O18ac:H7:K1.

RS218 *E. coli* were grown in RPMI media supplemented with 10% glucose to 0.5 McF (1e8 CFU/mL). RPMI media was used to avoid yeast extracts and other components that could interfere with FcMBL capture or compromise vaccine generation. Sufficient bacteria (a minimum of 1 mL of bacteria solution for each scaffold) were treated with 1 mg/mL Cefipime and 500 µg/mL Amikacin for 24 hours. Full killing of bacteria was confirmed by overnight plating where 0 CFU was detected The cell wall pathogen associated molecular patterns (PAMPs) of RS218 were captured using magnetic opsonins coated with FcMBL in combination with a biospleen dialysis-like therapeutic device. Captured RS218 were then included in a therapeutic vaccine using a PLGA scaffold in the presence or absence of CpG and GM-CSF adjuvants for in vivo mouse model studies.

Figure 2:
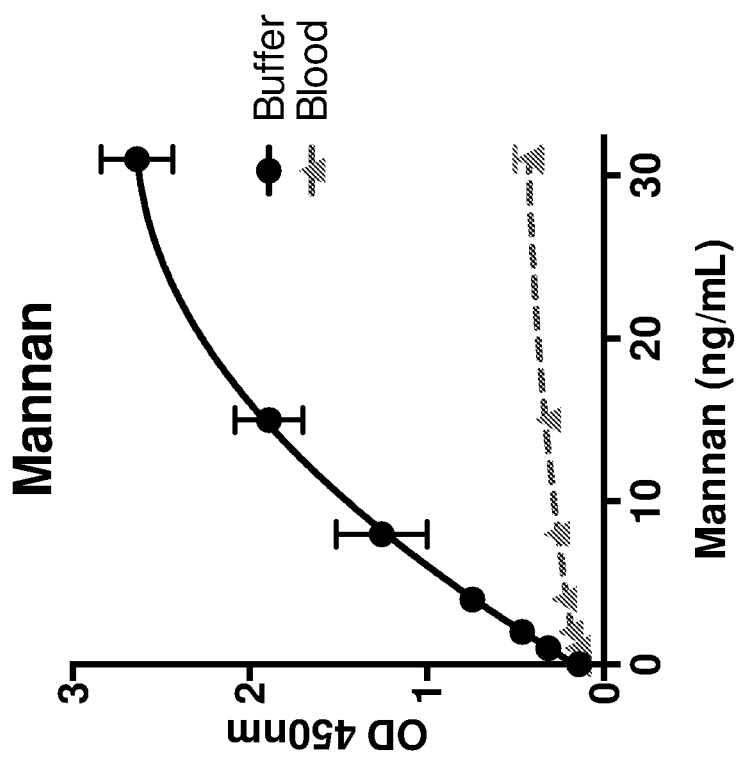
Figure 3:
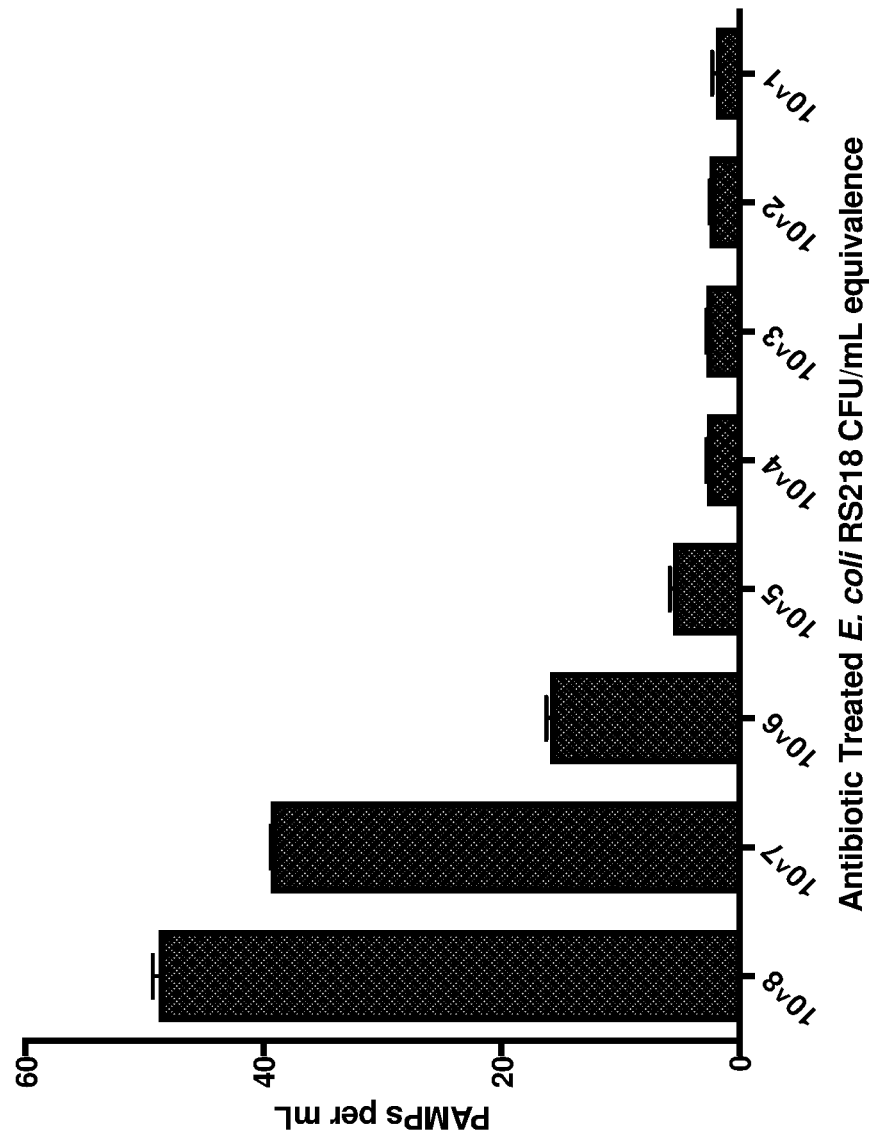
FIG. 3 depicts the quantification of captured RS218 fragments on FcMBL beads from titered antibiotics-treated RS218 solutions. The captured RS218 fragments were quantified as pathogen associated molecular patterns (PAMPs) using the standard curve generated by FcMBL ELISA.

The PAMPs captured by FcMBL were carbohydrate containing membrane components or fragments of RS218, for example, blebs, vesicles or LPS. To quantify PAMPs captured by FcMBL, a standard curve was generated using the fungal MBL target, mannan (FIG. 2). Briefly, 1 µM superparamagnetic beads coated with FcMBL were used to capture mannan in either buffer or whole donor blood. Serial dilutions of mannan were mixed with the FcMBL beads, and quantified by ELISA. RS218 cell wall fragments were quantified as MBL-bound pathogen associated molecular patterns (mPAMPs) by interpolation of the standard curve (FIG. 3). For RS218 bacteria, 15 ng/mL PAMPs on 25 µL/mL beads were chosen for subsequent vaccine generation.

Preparation of FcMBL-RS218 PAMPs Beads

Based on PAMPs quantification of antibiotics treated RS218 bacteria, 250 µl of beads (5 mg/mL) were added to 10 mL of diluted killed bacteria solution (equivalent to 15 ng/mL PAMPs) and incubated for 20 minutes. Beads were removed magnetically, washed 1× in TBST 5 mM $Ca^{++}$ and resuspended in 10 mL of TBST 5 mM $Ca^{++}$ for vaccine generation. Absence of live bacteria was reconfirmed by plating (0 CFUs). Samples were stored at −80° C.

Figure 4:
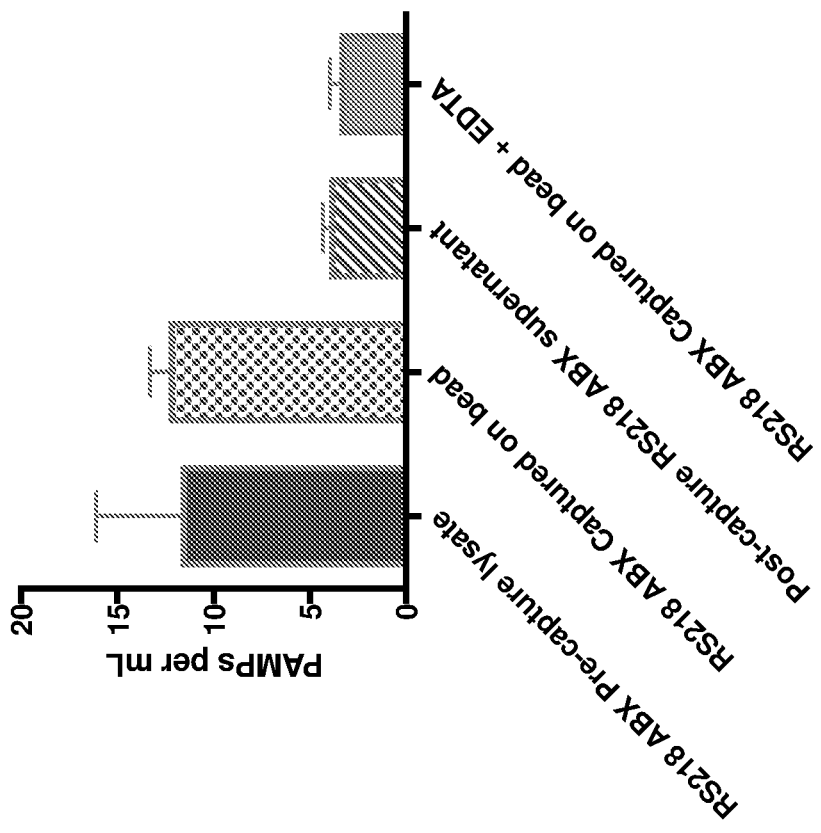
FIG. 4 depicts the quantification by FcMBL ELISA of RS218 PAMPs captured by FcMBL beads, and the specific calcium-dependent binding between FcMBL and RS218 PAMPs.

The amount of captured RS218 cell wall fragments was quantified as MBL-bound pathogen associated molecular patterns (mPAMPs) using the FcMBL ELISA (FIG. 4). Pre- and post-capture antibiotics treated RS218 solution was screened to determine if the amount of mPAMPs in RS218 was the same upon treatment with the FcMBL beads. 100 µL of RS218 samples were tested. As shown in FIG. 4, RS218 captured by FcMBL beads had a similar amount of mPAMPs when compared to the no bead control (RS218 pre-bead sample). EDTA control was included to demonstrate the calcium-dependence of mPAMP capture by FcMBL beads suggesting a specific binding between mPAMPs and FcMBL beads. Endotoxin capture was also quantified by comparison of the pre- and post-capture antibiotics treated RS218 solution (Table 1).

TABLE 1

Quantification of Endotoxin Captured by FcMBL Beads

|  | Endotoxin Units (EU/ml) |
|---|---|
| RS218 ABX Pre-Bead | 3290 |
| Post-bead Supernatant | 1300 |

Preparation of Vaccine Devices Using PLG Scaffolds and FcMBL Captured RS218

The vaccine devices used in the study were manufactured in accordance with the protocols developed for a standard PLG melanoma scaffold based on the WDVAX clinical trial. The FcMBL beads were incorporated into the scaffold similar to the incorporation of melanoma tumor lysate.

The PLG spheres used in this study were 30 µm poly (lactic-co-glycolic acid) (PLGA) spheres. For the control sham device, 180 mg blank PLG spheres were mixed with 1.3 g of sieved sucrose (250-400 µm). The resultant mixture was weighed and equal amounts were weighed out to enable the manufacture of 10 control sham devices.

For the beads/pathogen device (PLG scaffolds and FcMBL captured RS218), 180 mg blank PLG spheres were added to a 10 ml suspension of FcMBL captured RS218 cell wall fragments, mixed thoroughly, frozen and lyophilized for approximately 7 days. The lyophilized powder (304 mg) was mixed with 1.3 g of sieved sucrose (250-400 µm). The resultant mixture was weighed and equal amounts were weighed out to enable the manufacture of 10 bead/pathogen devices.

For full vaccine compositions, 180 mg PLG spheres with granulocyte macrophage colony-stimulating factor (GM-CSF) were added to a 10 ml suspension of FcMBL captured RS218 cell wall fragments, mixed thoroughly, frozen and lyophilized for approximately 7 days. The lyophilized powder (310 mg) was mixed with 1.3 g sieved sucrose (250-400 µm) and 300 mg CpG. The CpG was condensed using polyethylenimine (PEI). The resultant mixture was weighed and equal amounts were weighed out to enable the manufacture of 10 vaccine compositions.

To make the vaccine compositions, the appropriate quantity of lyophilized powders were placed into a 8 mm diameter die and formed under 1500 psi using a hydraulic press. Once formed, the compositions were foamed in a pressure chamber by means of exposure overnight to 800 psi $CO_2$ followed by a rapid pressure release. All compositions were stored at −20° C. until ready for animal implantation.

Preparation of Vaccine Devices Using PLG Scaffolds and FcMBL Captured E. cloacae Preparation of E. cloacae was done using the same method as listed above for E. coli RS218. In brief, E. cloacae is grown to 1e8 CFU/mL, treated with Cefepime (1 mg/mL) and Amikacin (500 µg/mL), and complete death of pathogen is confirmed by plating PAMPs are captured using 1 µM FcMBL Beads and quantified by FcMBL ELLecSA (Cartwright et al. EBioMedicine 9 (2016) 217-227). Beads containing PAMPs are then incorporated in PLG scaffold.

For manufacture of PLGA vaccine scaffolds, 18 mg PLG microspheres containing encapsulated GM-CSF (9 µg) were mixed until a homogenous powder was achieved with a solution containing 15 PAMPS, and then frozen using liquid $N_2$ and lyophilized below 100 militorr overnight. The resulting powder was thoroughly mixed with 30 mg CpG and 130 mg of sucrose prior to device pressing and high pressure $CO_2$ foaming. (7-900 PSI) The resulting devices were leached in WFI for 3 hours prior to implantation.

Preparation of Vaccine Devices Using MPS Scaffolds and FcMBL Captured RS218

Preparation of FcMBL captured RS218 beads is the same as described above. For manufacture of MPS vaccine scaffolds. 3 µg of GM-CSF, 10 mg of CpG and a solution containing 15 PAMPS were loaded onto 10 mg of MPSs and mixed vigorously overnight at room temperature using a rotary mixer. The MPSs were then lyophilized and reconstituted in water for injection (WFI) prior to injection.

PLG Scaffold Vaccination Protects Mice from Lethal R5218 Infection

To study the efficacy of the vaccine compositions, mice were first immunized with the vaccine compositions, and then challenged with a sub-lethal dose of RS218 bacteria. Specifically, RS218 captured using magnetic FcMBL beads were incorporated into a PLG scaffold with CpG and GM-CSF adjuvants to generate a full vaccine composition (FIG. 5A). FcMBL beads were clearly visible dispersed throughout the holes and cavities in the PLG scaffold (FIG. 5B). The vaccine compositions were then implanted into mice subcutaneously. Sham devices containing the scaffold alone were used as a negative control. Beads/pathogen devices where RS218 captured by FcMBL beads were incorporated into the PLG scaffold without any adjuvants were also included in the assay. 10 mice were included in each treatment group.

21 days after immunization, mice were challenged with a high, but sub-lethal dose of RS218 (5e6 CFU per mouse) by intraperitoneal injection for 48 hours. Mice were humanely sacrificed at 12 hours post infection or earlier if clinical conditions required. Humane endpoint occurred when clinical score dropped to ⅔ and when animals did not recover or experienced severe pain and distress unalleviated by nursing care.

Survival Curve Assay

Survival rate was monitored in RS218 infected mice. As demonstrated in FIG. 6, mice treated with full vaccine compositions (PLG scaffolds with FcMBL beads captured RS218 and GM-CSF/CpG) and beads/pathogen devices (PLG scaffold with FcMBL bead captured RS218 without GM-CSF/CpG) experienced a longer survival time than mice treated with sham devices (scaffold alone). 9 out of 10 mice survived after 48 hours when they were immunized with the full vaccine compositions. In comparison, 50% of mice receiving sham devices died about 10 hours after injection with the sub-lethal dose of RS218 bacteria, and half of the mice immunized with the beads/pathogen devices died after 20 hours. These results suggested that addition of adjuvants such as GM-CSF and CpG enhanced the efficacy of the vaccine compositions resulting in an increased survival time, and both the FcMBL captured pathogen and the adjuvants were needed for protective vaccination.

Organ Pathogen Counts

To quantify the pathogen load within selected organs in RS218 infected mice, organ cultures were collected in a sterile fashion, processed by mechanical disruption and plated. Briefly, organs harvested in a sterile fashion were added to bead mill tubes. 1 mL of sterile saline was added to each tube containing the beads and the organ. Each tube was weighted and each tube was bead milled for 5 minutes at a frequency of 30 per second. Liquefied organs were tittered 1:100 and 1:10,000. Undiluted, 1:100 and 1:10,000 organ samples were spiral plated on sheep blood agar, grown overnight at 37° C. and the pathogen load was determined. The organ pathogen counts in infected mice were described in Table 2. FIG. 7A demonstrates that the overall titer of pathogen was significantly reduced by 2.5-3.5 logs in mice receiving the full vaccine compositions (p=0.0021-0.0057), whereas no statistically significant difference was observed for mice receiving the beads/pathogen device and the sham control. Similar results were observed for pathogen load in individual organs. As demonstrated in FIG. 7B, the levels of RS218 in lung, liver, kidney and spleen were all significantly lower in mice receiving the full vaccine compositions (PLG scaffolds with FcMBL beads captured RS218 and GM-CSF/CpG), while mice receiving the beads/pathogen devices had a similar level of pathogens as the control mice, further suggesting that addition of adjuvants such as GM-CSF and CpG enhanced the efficacy of the vaccine compositions and were necessary for protective vaccination.

TABLE 2

Organ Pathogen Counts in Infected Mice

| Scaffold | Lung | Liver | Kidney | Spleen | Time (hours) |
|---|---|---|---|---|---|
| Mouse 4-1 | 1.32E+07 | 8.93E+08 | 3.11E+08 | 4.68E+08 | 8 |
| Mouse 4-4 | 1.00E+07 | 1.82E+08 | 3.54E+07 | 4.47E+08 | 8 |
| Mouse 6-3 | 3.07E+07 | 3.63E+07 | 1.68E+07 | 3.86E+07 | 11 |
| Mouse 2-2 | 3.86E+07 | 1.19E+09 | 1.53E+09 | 7.87E+08 | 24 |
| Mouse 2-5 | 2.61E+09 | 1.26E+09 | 6.24E+08 | 1.45E+09 | 24 |
| Mouse 3-3 | 1.59E+09 | 1.76E+09 | 1.24E+09 | 3.11E+09 | 12 |
| Mouse 1-4 | 2.27E+06 | 3.16E+08 | 1.86E+07 | 2.71E+07 | 22 |
| Mouse 1-1 | 3.27E+03 | 8.24E+08 | 8.27E+03 | 8.24E+03 | 48 |
| Mouse 5-2 | 2.23E+07 | 1.35E+08 | 3.96E+08 | 4.16E+07 | 36 |
| Mouse 5-5 | 7.25E+07 | 5.33E+04 | 2.38E+05 | 9.77E+04 | 48 |
| Scaffold & FcMBL/RS218 | | | | | |
| Mouse 4-2 | 2.36E+07 | 7.07E+08 | 9.52E+08 | 2.66E+08 | 9 |
| Mouse 3-1 | 2.83E+06 | 2.69E+07 | 1.35E+08 | 5.11E+08 | 11 |
| Mouse 5-3 | 2.41E+07 | 5.36E+08 | 1.36E+09 | 8.28E+08 | 11 |
| Mouse 6-4 | 3.18E+08 | 3.99E+06 | 3.59E+06 | 9.89E+06 | 11 |
| Mouse 2-3 | 2.22E+07 | 2.95E+08 | 2.58E+07 | 3.11E+07 | 22 |
| Mouse 3-4 | 6.04E+08 | 1.43E+09 | 4.55E+08 | 1.59E+09 | 22 |
| Mouse 1-5 | 8.22E+06 | 1.38E+07 | 3.34E+07 | 3.95E+07 | 11 |
| Mouse 1-2 | 1.72E+09 | 7.34E+08 | 1.19E+08 | 1.21E+09 | 12 |
| Mouse 4-5 | 8.40E+02 | 1.96E+04 | 1.88E+03 | 1.65E+03 | 48 |
| Scaffold & FcMBL/RS218 & GM-CpG | | | | | |
| Mouse 6-5 | 2.30E+06 | 2.24E+07 | 1.87E+07 | 9.59E+07 | 11 |
| Mouse 1-3 | 7.18E+04 | 3.57E+08 | 7.75E+03 | 3.97E+03 | 48 |
| Mouse 2-1 | 5.83E+06 | 5.43E+04 | 3.86E+03 | 7.08E+03 | 48 |
| Mouse 2-4 | 3.47E+04 | 9.00E+04 | 4.17E+03 | 5.91E+03 | 48 |
| Mouse 3-2 | 2.77E+04 | 1.62E+04 | 5.75E+03 | 4.02E+03 | 48 |
| Mouse 3-5 | 1.82E+03 | 5.92E+03 | 9.37E+03 | 2.10E+03 | 48 |
| Mouse 4-3 | 5.41E+02 | 7.98E+02 | 9.22E+02 | 2.62E+03 | 48 |
| Mouse 5-1 | 8.23E+05 | 1.80E+04 | 7.32E+03 | 4.89E+04 | 48 |
| Mouse 5-4 | 3.63E+04 | 1.59E+05 | 1.07E+04 | 6.56E+04 | 48 |
| Mouse 6-2 | 1.07E+03 | 1.06E+03 | 5.24E+02 | 1.57E+03 | 48 |

Comparison Between Vaccine with FcMBL Captured RS218 and Vaccine with RS218 Lysate To determine whether the observed protective effect of the full vaccine compositions can be reproduced with a lysate of RS218 without the FcMBL beads, PLG vaccine scaffolds with CpG/GM-CSF containing either FcMBL captured RS218 fragments or whole RS218 lysate alone were prepared.

Mice were divided into three treatment groups and PLG scaffolds were implanted subcutaneously for 21 days. Group 1 (n=10) received the sham device (scaffold and CpG/GM-CSF), Group 2 (n=10) received the scaffolds with CpG/GM-CSF containing FcMBL beads with captured RS218 fragments, and Group 3 (n=10) received the scaffolds with CpG/GM-CSF containing the whole RS218 lysate. Same amount of RS218 was used in Groups 2 and 3.

21 days after immunization, mice were challenged with a lethal dose of RS218 (with a 90% lethal dose (LD90) at 20 hours) by intraperitoneal injection and followed for 48 hours. As shown in FIG. 8, mice receiving both Group 2 and Group 3 vaccine compositions were protected against RS218 infection and had a prolonged survival time when compared to mice receiving the sham controls. 9 out of 10 mice receiving the Group 2 vaccine compositions and 10 out of 10 mice receiving the Group 3 vaccine compositions survived, whereas 9 out of 10 mice receiving the sham controls were euthanized at about 12 hours to avoid excessive pain and suffering.

Results from organ pathogen counts further suggested that vaccine compositions comprising either FcMBL beads with captured RS218 fragments (Group 2) or the whole RS218 lysate (Group 3) were effective in protecting mice from RS218 infection. FIG. 9 demonstrated that mice receiving both Groups 2 and 3 vaccine compositions had significantly less pathogen in the organs than mice in the sham vaccinated Group 1. For Group 2 mice, CFU/g titers dropped by 4-6 logs in lung, kidney, spleen, and by about 2 logs in liver. For Group 3 mice, CFU/g titers dropped by 3-4 logs in lung, liver, kidney and spleen. Accordingly, the levels of RS218 in the majority of organs, i.e., lung, kidney and spleen, were further reduced in vaccinated mice from Group 2 when compared to mice in Group 3, with the single exception of liver.

These results indicate that both the bacterial lysate and FcMBL bead captured bacterial fragments may be used in combination with PLG scaffolds to generate functional vaccine compositions and protect mice from a lethal challenge of infection. However, vaccine compositions with FcMBL bead captured pathogen fragments exhibited a significant advantage over the direct use of bacterial lysate because no side effect such as leaching lysate and formation of abscess was observed.

As shown in FIG. 10C, a significant endotoxin leakage was observed in mice implanted with the PLG vaccine scaffolds containing the whole RS218 lysate (Group 3), whereas the PLG vaccine scaffolds containing the FcMBL captured RS218 fragments demonstrated no such leakage (Group 2). In addition, at 48 hour sacrifice, formation of large abscesses was observed surrounding the scaffolds in Group 3 mice and the scaffold could not be separated from adhesions (FIG. 11C). In contrast, the vaccine compositions in Group 2 mice were largely intact and clean, with little signs of eroding (FIG. 11B) and Group 1 control mice had intact scaffold with no signs of immune reaction (FIG. 11A). 28 days after vaccination, the sham vaccine (Group 1) and vaccine compositions comprising FcMBL beads with captured RS218 fragments (Group 2) were still present, however, where the RS218 lysate was incorporated directly into the PLG scaffold (Group 3), there was a strong local inflammatory reaction and the scaffold was degraded away, and these mice had abscesses at the vaccine sites.

The levels of CpG and GM-CSF leakage from the PLG vaccine scaffolds were also quantified and compared between the three treatment groups. FIG. 10A and FIG. 10B demonstrated that no significant difference was observed for CpG and GM-CSF leakage.

Therefore, although vaccines compositions comprising both the bacterial lysate and FcMBL bead captured bacterial fragments were shown to protect mice from a lethal challenge of bacteria infection, the vaccine compositions with FcMBL bead captured pathogen fragments presented a safer, more controlled and localized option without compromising the efficacy of the vaccine compositions.

Cross-Reactivity of Vaccine Compositions with FcMBL Captured Pathogens

To determine whether the vaccine compositions of the invention can be used against different species of a pathogen, PLG vaccine scaffolds containing CpG/GM-CSF and FcMBL captured *E. cloacae* lysates were prepared using the same method as listed above. In brief, *E. cloacae* is grown to 1e8 CFU/mL, treated with Cefepime (1 mg/mL) and Amikacin (500 µg/mL), and complete death of pathogen is confirmed by plating. PAMPs are captured using FcMBL Beads and quantified by FcMBL ELLecSA. Beads containing PAMPs are then incorporated in PLG scaffold.

Mice were challenged with a lethal dose of RS218 (with a LD90 at 20 hours) by intraperitoneal injection. Both *E. cloacae* and *E. coli* are members of the order Enterobacteriaceae. As shown in FIG. 12A, a prophylactic vaccine of PLG-GMCSF/CpG with FcMBL beads coated with *E. cloacae* lysate protected 78% mice till the end of the study at 96 hours from the RS218 challenge, while PLG scaffold with only GM-CSF recruiting and CpG adjuvant (without FcMBL beads and bacteria lysate) protected only 20% of animals at 96 hours. The vaccine of PLG scaffold containing GM-CSF/CpG and FcMBL beads coated with RS218 lysate protected 100% mice till the end of the study at 96 hours from the RS218 challenge.

In addition, FIG. 12B showed that pathogen counts were reduced in mice receiving the vaccine of PLG-GMCSF/CpG with FcMBL beads coated with *E. cloacae* lysate.

There results demonstrate that the present vaccine compositions are capable of targeting against different species or strains of a given pathogen, thus conferring a significant advantage over existing vaccines.

Long-Term Effect of a Single Implanted Dose of Vaccine Compositions

To determine whether the vaccine compositions of the invention can confer a long-term protective effect against a pathogen, mice were first immunized with a PLG-GMCSF/CpG vaccine composition with FcMBL beads coated with *E. coli* RS218 lysate on Day 1, challenged with a sub-lethal dose of RS218 bacteria (LD90 at 20 hours) at Day 21, and rechallenged on Days 60 and 90. As shown in FIG. 15A, all mice receiving the vaccine compositions survived for more than 90 days, where the control mice died immediately after the RS218 challenge at Day 21. These results demonstrate that the vaccine compositions are capable of producing a long-term protective effect against the infected pathogen, and a single dose of vaccine compositions can protect the infected subjects for at least 90 days.

To confirm the sustained effect of the vaccine compositions, mice were vaccinated on Day 1 and then challenged with a higher RS218 dose with a 90% lethal dosage at 8 hours on Day 90. FIG. 15B showed that 75% of mice receiving the PLG vaccine compositions survived for more than 120 days after the RS218 challenge, whereas the control mice died immediately after the challenge.

MPS Scaffold Vaccination Protects Mice from Lethal R5218 Infection

Vaccine compostitions comprising mesoporous silica (MPS) scaffolds were generated. To study the efficacy of the MPS based vaccine compositions, mice were first immunized with the vaccine compositions, and then challenged with a sub-lethal dose of RS218 bacteria (LD100 at 36 hours). Specifically, FcMBL captured RS218 fragments were incorporated into a MPS scaffold with CpG and GM-CSF adjuvants to generate a full vaccine composition. Vaccine compositions were then injected into mice. Different doses of the captured pathogen (3 PAMP units and 15 PAMP units) were coated onto the FcMBL beads and then incorporated into the MPS-GMCSF/CpG scaffold. 15 PAMP units of RS218 were also incorproeated into a PLG scaffold as a control.

As shown in FIG. 13, MPS scaffolds containing GM-CSF/CpG and 15 PAMP units protected 90% of mice from 21-days challenge while MPS scaffolds containing 3 PAMP units only protected 70%. All the mice receiving PLG scaffolds containing GM-CSF/CpG and FcMBL beads coated with 15 PAMPs also survived the challenge.

Another set of MPS based vaccines was prepared with a different pathogen dosage (7.5 PAMP units). FIG. 14 shows that the MPS vaccine containing GM-CSF/CpG and 7.5 PAMP units protected 90% mice till the end of the study at 96 hours from the RS218 challenge (LD90 at 10 hrs) (n=12). However, only 50% of mice vaccinated with sham vaccine survived the bacteria challenge (n=6).

In conclusion, these results demonstrated that PLG or MPS scaffolds loaded with FcMBL captured pathogens and with adjuvants such as CpG/GM-CSF could function as an effective vaccine composition and protect mice from a lethal bacterial infection. Mice immunized with these vaccine compositions exhibited a significantly prolonged survival time and a lower organ pathogen count. The ability to combine the FcMBL bead captured pathogens or pathogen associated molecular patterns with the vaccine scaffolds, e.g., PLG or MPS scaffolds, allows the creation of high potency pathogen vaccines against all types of pathogens, which could be of great use in treatment of infectious diseases. In addition, the use of non-infectious vaccines and the ability to prevent leakage of the pathogen from the vaccine composition greatly reduced the severe side effects experienced with the leakage of pathogen toxins, thus resulting in a safer, and more controlled vaccine composition. Further more, the present vaccine compositions are capable of targeting against different species or strains of a given pathogen, and producing a long-term protective effect against the infected pathogen. Indeed, a single dose of the vaccine composition of the invention can protect the vaccinated mice from a bacteria challenge over a period of 90 days.

The results were clinically significant as the vaccine compositions and methods demonstrated the ability to target a specific pathogen in vivo for the generation of immunity, resulting in distinct and protective immune responses.

Example 2

Mechanistic Analysis of the Vaccine Compositions

Additional experiments were performed to determine the kind of immune response involved for the vaccine compositions (PLG or MPS scaffolds loaded with FcMBL captured pathogens and with adjuvants such as CpG/GM-CSF). Specifically, assays were performed to determine whether the vaccine compositions of the invention mediate a cell-mediated response, or an antibody-mediated response. Changes in the levels of selected cytokines and the levels of specific IgGs, e.g., IgG1 and IgG2a, were measured in response to RS218 infection in the vaccinated animals. A major change in the level of cytokines will be an indication that the vaccine compositions primarily act through the cell-mediated response, whereas a significant change in IgG levels will suggest an antibody-mediated response.

Histology studies were performed to determine whether the vaccine compositions of the invention were capable of eliciting a cell-mediated immune response against infected pathogens. Mice were implanted with PLG scaffolds with FcMBL beads captured RS218 and GM-CSF/CpG), or injected with MPS scaffolds with FcMBL beads captured RS218 and GM-CSF/CpG). The implant sites that contained the sham and complete vaccine were explanted, embedded, sectioned and stained with Haematoxylin Eosin to identify infiltrating immune cells. As shown in FIG. 16, no cell was accumulated in the control PLG sham device, whereas dense cellular infiltration were observed with both PLG and MPS scaffolds, suggesting that a cell-mediated response was initiated by the vaccine compostions.

To determine whether the vaccine compositons mediated an antibody-mediated immune response against infected pathogen, IgG levels were measured. The analysis was conducted using a Sera ELISA that detects anti-RS218 PAMP IgG and IgM antibodies. The 96 well microplates are coated with RS218 lysate, blocked, and the plates are washed. The samples are diluted between $10^3$-$10^6$, then incubated at room temperature. The plates is aspirated and washed, prior to incubation with with HRP goat anti mouse IgG secondary antibody conjugate. Finally, a TMB Substrate is added to create an enzymatic reaction and incubated. The samples are then analyzed using a spectrophotomter at a wavelength of 450 nm. The results of the serial dilutions can then be calculated to determine the optical density at 0.5 AU, which is used as a convention for establishing antibody titers. FIG. 17 shows that IgG titeres were significantly increased in mice receiving the vaccine compositions and the increase in IgG levels lasted for a period of about 90 day, further suggesting that a long-term antibody-mediated immune response was elicited by the vaccine compositions.

Example 3

Vaccination Protects Against Multiple Pathogen Infections

Vaccination Protects Mice from *Mycobacterium Tuberculosis* Infection

Tuberculosis (TB) is an infectious disease caused by the bacterium *Mycobacterium tuberculosis* (MTb). Tuberculosis generally affects the lungs, but can also affect other parts of the body. Most TB infections do not have symptoms; in which case it is known as latent tuberculosis. About 10% of latent infections progress to active disease which, if left untreated, kill about half of those infected. FcMBL can bind to mannosylated components of *Mycobacterium tuberculosis* (MTb) cell wall, for example, mannose-capped Lipoarabinomannan (ManLAM) and Phosphatidylinositol Mannoside (PIM) (FIG. 18).

To determine whether the vaccine compositions of the present invention may be used to protect against tuberculosis, mice were immunized with a single dose of MPS based vaccine compositions containing GM-CSF/CpG and FcMBL beads coated with mannose-capped Lipoarabinomannan (ManLAM) lysate. FIG. 19 shows that a single dose of the vaccine compositon increased the titers of LAM-specific IgG by about 2-3 logs over pre-vaccinated naïve animals (p=<0.001). In addition, a significant increase in the amount of macrophages, CD4+ T cells and dentritic cells were also observed within the MPS scaffolds (FIG. 20), demonstrating that a cell-mediated anti-LAM immune response was also produced in vaccinated mice. To prepare cells for FACS analysis, single-cell suspensions from infection vaccine scaffolds were prepared by digesting in collagenase IV (1 mg/ml), for 20 min at 37° C. followed by filtering through 70 µm mesh. Spleenic controls for cell gating were mashed through a 70 µm mesh and red blood cells were lysed with ACK buffer (150 mM $NH_4Cl$, 1 mM $KHCO_3$, $Na_2EDTA$ 0.1 mM). Cells were treated with Fc block (anti-mouse CD16/32) and stained with antibodies to CD3e (PE, BD Biosciences), CD4 (PECY7, BD Biosciences), CD8 (FITC, BD Biosciences), The flow cytometry data was analyzed using FlowJo (Tree Star). The numbers of $CD4^+$ and $CD8^+$ T cells in the scaffolds were determined by using a hemacytometer in combination with cell densities from flow analyses.

These data demonstrate that the vaccine compostions of the invention are capable of targeting *Mycobacterium tuberculosis* and, thus, have a great potential in treating tuberculosis.

Vaccination Protects Against Other Pathogens

Since FcMBL is capable of capturing multiple pathogen genera, vaccine compositions for additional pathogens, for example, gram negative bacteria (*E. coli* RS218), Gram positive (MRSA) LAM (*Mycobacterium tuberculosis*-cell wall component), fungi (*Candida albicans*), viruses (HIV gp120 antigen) and parasites (*Trichomonas vaginalis* antigen), were generated.

Each viable pathogen is treated with an appropriate antibiotic. MRSA is killed using Cefepime (1 mg/mL) and Vancomycin (500 µg/mL) and *Candida albicans* is killed using Amphotericin B (1 mg/mL). Preparation of FcMBL captured pathogens/antigens coated beads is the same as described above in sections: Preparation of Pathogen and FcMBL-RS218 PAMPs Beads.

FIG. 21A shows that FcMBL beads were coated with different amount of pathogen fragments for vaccine preparation. Mice were then vaccinated with a single dose of MPS based vaccine compositions containing GM-CSF/CpG and FcMBL beads coated with with samples from the infectious microorganisms. FIG. 21B shows that the titers of LAM-specific IgG was increased over pre-vaccinated naïve animals in all cases, demonstrating that the vaccine compositions were suitable for targeting and mediating immune responses against multiple pathogen species.

In addition to antibody-mediated immune response, the vaccine composition were able to elicit cell-medisted immune response against targeted pathogens. FACS anaklysis of infiltrating cells in splens of vaccinated animals demonstrated the cell-mediated anti-*Trichomonas* response against *Trichomonas* lysate incoporated into a vaccine (FIG. 22). Control spleens (Naive) showed fewer infiltrating CD4+T cells & CD11c cells than in the vaccinated animal groups.

Example 4

MPS Scaffold Vaccination with FcSPD Captured RS218

An alternative lectin was used to capture pathogen. Pulmonary surfactants, a complex mixture of lipids and proteins, are essential for lung function. Surfactant protein D (SPD) is another collectin (C-type lectin with collagen region) related to MBL. SPD has a primary role in host defense of the lung. An FcSPD fusion protein was generated, which has 77% protein sequence identity to FcMBL. Preparation of FcSPD captured RS218 beads are similar as described above.

As shown in FIG. 23, FcSPD was able to bind the RS218 *E. coli* and the FcSPD captured RS218, when incorcoporate in the MPS scaffold, also mounted an immune reaction in vaccinated mice. An increased antibody titer was observed in vaccinated mice, demonstrating that vaccine compositions comprising FcSPD-captured pathogens were also capable of mediating immune response against infected pathogens.

EQUIVALENTS

Those skilled in the art will recognize, or be able to ascertain using no more than routine experimentation, many equivalents to the specific embodiments of the invention described herein. such equivalents are intended to be encompassed by the following claims. The contents of all references, patents and published patent applications cited throughout this application are incorporated herein by reference.

We claim:

1. A vaccine composition, comprising
a scaffold comprising a biomaterial;
a lectin-bound pathogen construct encapsulated by the scaffold, wherein the lectin-bound pathogen construct comprises a solid substrate coupled to an immunoglobulin (IgG) Fc region fused to a lectin, or portion thereof; and a pathogen, or portion thereof, bound to the lectin, or portion thereof;
a bioagent which recruits an immune cell in a subject; and
an adjuvant which stimulates an immune response to the pathogen, or portion thereof, in the subject.

2. The vaccine composition of claim 1, wherein the biomaterial is selected from the group consisting of glycosaminoglycan, silk, fibrin, the gelatinous protein mixture secreted by Engelbreth-Holm-Swarm (EHS) mouse sarcoma cells, poly-ethyleneglycol (PEG), polyhydroxy ethyl methacrylate, polyvinyl alcohol, polyacrylamide, poly (N-vinyl pyrolidone), poly(lactic acid), poly glycolic acid (PGA), poly lactic-co-glycolic acid (PLGA), poly e-carpolactone (PCL), polyethylene oxide, poly propylene fumarate (PPF), poly acrylic acid (PAA), polyhydroxybutyric acid, hydrolysed polyacrylonitrile, polymethacrylic acid, polyethylene amine, esters of alginic acid; pectinic acid; and alginate, fully or partially oxidized alginate, hyaluronic acid, carboxy methyl cellulose, heparin, heparin sulfate, chitosan, carboxymethyl chitosan, chitin, pullulan, gellan, xanthan, collagen, gelatin, carboxymethyl starch, carboxymethyl dextran, chondroitin sulfate, cationic guar, cationic starch, and combinations thereof.

3. The vaccine composition of claim 1, wherein the biomaterial is selected from the group consisting of poly(L-lactide-co-glycolide) acid (PLGA), mesoporous silica, cryogel, and combinations thereof.

4. The vaccine composition of claim 1, wherein the bioagent is selected from the group consisting of interleukin (IL)-1, IL-2, IL-3, IL-4, IL-5, IL-6, IL-7, IL-8, IL-10, IL-12, IL-15, IL-17, IL-18, tumor necrosis factor (TNF)-alpha, interferon (IFN)-gamma, IFN-alpha, granulocyte macrophage colony stimulating factor (GM-CSF), granulocyte colony stimulating factor (G-CSF), Fms-related tyrosine kinase ligand (FTL)-3 ligand, CCL19, CCL21, M-SCF, MIF, CD40L, CD3, ICAM, transforming growth factor (TGF)-beta, cytosine-guanosine oligonucleotide (CpG-ODN), lipopolysaccharides (LPS), Fas ligand, Trail, lymphotactin, Mannan (M-FP), APG-2, Hsp70 and Hsp90.

5. The vaccine composition of claim 4, wherein the bioagent comprises granulocyte macrophage colony stimulating factor (GM-CSF).

6. The vaccine composition of claim 1, wherein the adjuvant is selected from the group consisting of cytosine-guanosine oligonucleotide (CpG-ODN) sequence, granulocyte macrophage colony stimulating factor (GM-CSF), ovalbumin (OVA), monophosphoryl lipid A (MPL), poly(I:C), MF59, alum, aluminum hydroxide, aluminum phosphate, calcium phosphate hydroxide, Quil A, N-acetyl muramyl-L-alanyl-D-isoglutamine (MDP), FIA, montanide, adjuvant 65, lipovant, poly (DL-lactide-coglycolide) microspheres, paraffin oil, squalene, virosome, AS03, ASO4, IL-1, IL-2, IL-3, IL-4, IL-5, IL-6, IL-7, IL-8, IL-10, IL-12, IL-15, IL-17, IL-18, STING, Toll-like receptor ligand, CD40L, pathogen-associated molecular patterns (PAMPs), damage-associated molecular pattern molecules (DAMPs), Freund's complete adjuvant, Freund's incomplete adjuvant, transforming growth factor (TGF)-beta antibody or antagonists, A2aR antagonists, lipopolysaccharides (LPS), Fas ligand, Trail, lymphotactin, Mannan (M-FP), APG-2, Hsp70 and Hsp90.

7. The vaccine composition of claim 6, wherein the adjuvant is granulocyte macrophage colony stimulating factor (GM-CSF).

8. The vaccine composition of claim 6, wherein the adjuvant comprises a CpG-ODN sequence.

9. The vaccine composition of claim 8, wherein the CpG-ODN sequence comprises a polyehylenimine (PEI)-CpG-ODN sequence.

10. The vaccine composition of claim 1, wherein the lectin, or portion thereof, is an engineered lectin, or portion thereof.

11. The vaccine composition of claim 1, wherein the lectin, or portion thereof, is selected from the group consisting of a collectin, a ficollin, and a mannose-binding lectin (MBL).

12. The vaccine composition of claim 11, wherein the lectin or portion thereof, comprises amino acid residues 81 to 228 of human MBL; or amino acid resides 111 to 228 of human MBL.

13. The vaccine composition of claim 1, wherein the lectin comprises Surfactant Protein D (SPD).

14. The vaccine composition of claim 1, wherein the solid substrate is selected from the group consisting of a magnetic bead, a microporous membrane, a hollow-fiber reactor, a blood filtration membrane and a blood flow device.

15. The vaccine composition of claim 14, wherein the solid substrate is a magnetic bead.

16. The vaccine composition of claim 1, wherein the pathogen, or portion thereof, is present in the vaccine composition at a quantity of about 1 pg to about 1000 µg.

17. The vaccine composition of claim 1, wherein the pathogen, or portion thereof, is an infectious microorganism selected from the group consisting of a bacterium, a fungus, a virus and a parasite, or a fragment thereof.

18. The vaccine composition of claim 17, wherein the bacterium is selected from the group consisting of *Acinetobacter baumanii, Burkholderia cepacia, Bacterioides fragilis, Chlamydia trachomatis, Citrobacter freundii, Campylobacter jejuni, Escherichia coli, Enterobacter aerogenes, Enterobacter cloacae, Haemophilus* inf b, *Helicobacter pylori, Klebsiella oxytoca, K. pneumonia* (MDR/CRE), *Legionella pneumophila, Neisseria meningitides, Neisseria gonorrhoeae, Pseudomonas aeruginosa, Salmonella typhi, paratyphi, typhimurium, Serratia marcescens, Shigella flexneri, Stenotrophomonas maltophilia, Yersinia pseudotuberculosis, Bacillus subtilis, Clostridium neoformans, C. difficile, C. perfringens, Corynebacterium* spp, *Enterococcus faecalis, Enterococcus faecium*, vancomycin-resistant *Enterococci* (VRE), *Listeria monocytogenes, Mycobactrium avium, M. tuberculosis, M. leprae, Nocardia farcinica, P. acnes, Staphylococcus aureus*, methicillin-susceptible *Staphylococcus aureus* (MSSA), methicillin-resistant *Staphylococcus aureus* (MRSA), *Staphylococcus epidermidis, Streptococcus pyogenes*, Strep Group A, Strep Group B (*agalactiae*) and Strep Group C.

19. The vaccine composition of claim 17, wherein the bacterium is an antibiotic-resistant bacterium or a multi-drug resistant bacterium.

20. The vaccine composition of claim 19, wherein the antibiotic-resistant bacterium or the multi-drug resistant bacterium is selected from the group consisting of *Acinetobacter baumanii, Escherichia coli, Klebsiella oxytoca, K. pneumonia* (MDR/CRE), *Pseudomonas aeruginosa, C. difficile*, vancomycin-resistant *Enterococci* (VRE) and methicillin-resistant *Staphylococcus aureus* (MRSA).

21. The vaccine composition of claim 17, wherein the fungus is selected from the group consisting of *Aspergillus* spp, *Blastomyces, Candida albicans, glabrata, guilliermondii, krusei, parapsilosis, tropicalis, Cryptococcus, Fusarium* spp., *Mucor* spp., *Saccharomyces*, and *Pneumocystis jirovecii* (*carinii*).

22. The vaccine composition of claim 17, wherein the virus is selected from the group consisting of Dengue virus, Ebola virus, EBV, Hepitis A virus, Hepitis B virus, Hepitis C virus, Hepitis D virus, HSV 1, HSV 2, HIV, Cytomegalovirus (CMV), Influenza A virus, Marburg virus, Human respiratory syncytial virus (RSV), SARS-CoV, West Nile virus, Human papillomavirus (HPV), Human rhinoviruses (HRVs), and Zica virus.

23. The vaccine composition of claim 17, wherein the parasite is selected from the group consisting of *Cryptosporidium, Leishmania, Malaria, Schistosoma, Trichomonas* and *Trypanosoma*.

24. The vaccine composition of claim 17, wherein the pathogen, or portion thereof, comprises a cell membrane component of the infectious microorganism.

25. The vaccine composition of claim 17, wherein the pathogen, or portion thereof, comprises a whole cell isolated from the infectious microorganism.

26. The vaccine composition of claim 1, wherein the pathogen, or portion thereof, is a *mycoplasma*.

27. The vaccine composition of claim 26, wherein the *mycoplasma* is selected from the group consisting of *M. pneumoniae, M. hominis* and *M. orale*.

28. The vaccine composition of claim 1, wherein the pathogen, or portion thereof, comprises a pathogen-associated molecule pattern (PAMP).

29. The vaccine composition of claim 28, wherein the PAMP is selected from the group consisting of a pathogen fragment, a pathogen debris, a pathogen nucleic acid, a pathogen lipoprotein, a pathogen surface glycoprotein, a pathogen membrane component, and a component released from the pathogen.

30. The vaccine composition of claim 29, wherein the component released from the pathogen, or portion thereof, comprises a toxin.

31. The vaccine composition of claim 30, wherein the toxin is selected from the group consisting of endotoxin, lipopolysaccharide (LPS), lipoteichoic acid (LTA), wall teichoic acid (WTA) and Ricin.

32. The vaccine composition of claim 1, wherein the pathogen, or portion thereof, is in a sample derived from a subject.

33. The vaccine composition of claim 32, wherein the sample is selected from the group consisting of a blood sample, a plasma sample, a serum sample, a blood culture sample, a cerebrospinal fluid sample, a joint fluid sample, a urine sample, a semen sample, a saliva sample, a sputum sample, a bronchial fluid sample, and a tear sample.

34. The vaccine composition of claim 1, wherein the pathogen, or portion thereof, is derived from an in vitro culture, a microorganism lysate, a crude lysate, or a purified lysate.

35. The vaccine composition of claim 1, wherein the pathogen, or portion thereof, is a synthetic pathogen.

36. The vaccine composition of claim 1, wherein the pathogen, or portion thereof, is neutralized.

37. The vaccine composition of claim 36, wherein the pathogen or portion thereof, is neutralized by treatment with antibiotics, ultraviolet light, sonication, microwave, bead mill, x-ray, autoclave, irradiation or mechanical disruption.

38. The vaccine composition of claim 37, wherein the pathogen, or portion thereof, is non-infectious after neutralization.

39. The vaccine composition of claim 1, wherein the immune cell is an antigen-presenting cell.

40. The vaccine composition of claim 39, wherein the immune cell is selected from the group consisting of a dendritic cell, a macrophage, a T cell and a B cell.

41. The vaccine composition of claim 1, wherein the vaccine composition comprises at least two different types of pathogens, or portions thereof.

42. The vaccine composition of claim 1, wherein the vaccine composition is capable of targeting against different species of a pathogen.

43. The vaccine composition of claim 1, wherein the vaccine composition is suitable for implantation in a subject; is suitable for injection in a subject; or is suitable for oral administration in a subject.

44. The vaccine composition of claim 43, wherein the vaccine composition is suitable for subcutaneous implantation.

45. The vaccine composition of claim 43, wherein the vaccine composition is in the form of a pill, a tablet, a capsule, a soft gel, a chewable, a powder, an emulsion, or an aqueous solution.

46. The vaccine composition of claim 1, wherein the vaccine composition is lyophilized.

47. The vaccine composition of claim 46, wherein the vaccine composition has a shelf life of about 30 days to about 1 year; or is capable of being stored at room temperature.

48. The vaccine composition of claim 1, wherein the vaccine composition is capable of immobilizing the lectin-bound pathogen construct and preventing leakage of the lectin-bound pathogen construct from the scaffold.

49. The vaccine composition of claim 1, wherein the immunoglobulin Fc region is directly coupled to the solid substrate.

50. The vaccine composition of claim 1, wherein the immunoglobulin Fc region is indirectly coupled to the solid substrate by an amino-oxy biotin.

51. A vaccine composition, comprising
a scaffold comprising a biomaterial selected from the group consisting of poly(L-lactide-co-glycolide) acid (PLGA), mesoporous silica, cryogel, and combinations thereof;
a lectin-bound pathogen construct encapsulated by the scaffold, wherein the lectin-bound pathogen construct comprises a bead coupled to an immunoglobulin (IgG) Fc region fused to a lectin, or portion thereof; and a pathogen, or portion thereof, bound to the lectin, or portion thereof;
a bioagent which recruits an immune cell in a subject; and
an adjuvant which stimulates an immune response to the pathogen, or portion thereof, in the subject.

52. A vaccine composition, comprising
a scaffold comprising mesoporous silica;
a lectin-bound pathogen construct encapsulated by the scaffold, wherein the lectin-bound pathogen construct comprises a magnetic bead coupled to an immunoglobulin (IgG) Fc region fused to a mannose-binding lectin (MBL), or portion thereof; and a pathogen, or portion thereof, bound to the lectin, or portion thereof;
a bioagent comprising granulocyte macrophage colony stimulating factor (GM-CSF); and
an adjuvant comprising granulocyte macrophage colony stimulating factor (GM-CSF) and/or a CpG-ODN sequence.

53. A vaccine composition, comprising
a scaffold comprising poly (L-lactide-co-glycolide) acid (PLGA);
a lectin-bound pathogen construct encapsulated by the scaffold, wherein the lectin-bound pathogen construct comprises a magnetic bead coupled to an immunoglobulin (IgG) Fc region fused to a mannose-binding lectin (MBL), or portion thereof; and a pathogen, or portion thereof, bound to the lectin, or portion thereof;
a bioagent comprising granulocyte macrophage colony stimulating factor (GM-CSF); and
an adjuvant comprising granulocyte macrophage colony stimulating factor (GM-CSF) and/or a CpG-ODN sequence.

54. The vaccine composition of claim 52 or 53, wherein the pathogen or portion thereof, comprises a pathogen-associated molecule pattern (PAMP).

55. The vaccine composition of claim 52 or 53, wherein the pathogen, or portion thereof, is a bacterium.

56. The vaccine composition of claim 55, wherein the bacterium is an antibiotic-resistant bacterium or a multi-drug resistant bacterium.

57. The vaccine composition of claim 56, wherein the antibiotic-resistant bacterium or the multi-drug resistant bacterium is selected from the group consisting of *Acinetobacter baumanii*, *Escherichia coli*, *Klebsiella oxytoca*, *K. pneumonia* (MDR/CRE), *Pseudomonas aeruginosa*, *C. difficile*, vancomycin-resistant *Enterococci* (VRE) and methicillin-resistant *Staphylococcus aureus* (MRSA).

58. The vaccine composition of claim 52 or 53, wherein the vaccine composition is capable of being stored at room temperature.

59. A kit for vaccinating a subject against a pathogen infection, comprising
a vaccine composition of claim 1; and
instructions for administering the vaccine to the subject.

60. A kit for vaccinating a subject against a pathogen infection, comprising
a vaccine composition of claim 52; and
instructions for administering the vaccine to the subject.

61. The kit of claim 60, wherein the vaccine composition is prepackaged in a sterile container.

62. A kit for vaccinating a subject against a pathogen infection, comprising
a vaccine composition of claim 53; and
instructions for administering the vaccine to the subject.

63. The kit of claim 62, wherein the vaccine composition is prepackaged in a sterile container.

64. A method of treating an antibiotic-resistant bacterial infection in a subject in need thereof, comprising administering the vaccine composition of claim 1 to the subject, thereby treating the antibiotic-resistant bacterial infection in the subject.

65. A method of increasing the survival rate of a subject having a pathogen infection, comprising administering the vaccine composition of claim 1 to the subject, thereby increasing the survival rate of the subject.

66. A method of treating a pathogen infection in a subject in need thereof, comprising administering the vaccine composition of claim 1 to the subject, thereby treating the pathogen infection in the subject.

67. A method of vaccinating a subject against a pathogen infection, comprising administering the vaccine composition of claim 1 to the subject, thereby vaccinating the subject against the pathogen infection.

68. A method of decreasing the level of a pathogen in a subject having a pathogen infection, comprising administering the vaccine composition of claim 1 to the subject, thereby decreasing the level of the pathogen in the subject.

69. The method of any one of claims 64, 65, 66, 67, and 68, wherein the subject is a mammal.

70. The method of claim 69, wherein the mammal is selected from the group consisting of a human, an embryo, a horse, a dog, a cat, a cow, a sheep, a pig, a fish, an amphibian, a reptile, a goat, a bird, a monkey, a mouse, a rabbit, and a rat.

71. The method of claim 69, wherein the mammal is a human.

72. The method of claim 64, wherein the lectin-bound pathogen construct is specific for the antibiotic-resistant bacterium in the subject.

73. The method of claim 68, wherein the level of the pathogen is decreased in an organ of the subject.

74. The method of claim 72, wherein the organ is selected from the group consisting of a lung, a liver, a kidney, and a spleen.

75. The method of any one of claims 64, 65, 66, 67, and 68, wherein the infection is an acute infection.

76. The method of any one of claims 64, 65, 66, 67, and 68, wherein the infection is a chronic infection.

77. The method of any one of claims 64, 65, 66, 67, and 68, wherein the infection causes an epidemic.

78. The method of any one of claims 64, 65, 66, 67, and 68, wherein the infection causes a pandemic.

79. The method of any one of claims 64, 65, 66, 67, and 68, wherein the infection occurs during a war.

* * * * *